US012595313B2

(12) United States Patent
Durrant et al.

(10) Patent No.: US 12,595,313 B2
(45) Date of Patent: Apr. 7, 2026

(54) MODIFIED FC-REGIONS TO ENHANCE FUNCTIONAL AFFINITY OF ANTIBODIES AND ANTIGEN BINDING FRAGMENTS THEREOF

(71) Applicant: Scancell Limited, Nottingham (GB)

(72) Inventors: Linda Gillian Durrant, Nottingham (GB); Mireille Vankemmelbeke, Nottingham (GB)

(73) Assignee: Scancell Limited, Oxford (GB)

( * ) Notice: Subject to any disclaimer, the term of this patent is extended or adjusted under 35 U.S.C. 154(b) by 1107 days.

(21) Appl. No.: 17/631,078

(22) PCT Filed: Jul. 31, 2020

(86) PCT No.: PCT/EP2020/071724
§ 371 (c)(1),
(2) Date: Jan. 28, 2022

(87) PCT Pub. No.: WO2021/019094
PCT Pub. Date: Feb. 4, 2021

(65) Prior Publication Data
US 2022/0298256 A1     Sep. 22, 2022

(30) Foreign Application Priority Data
Jul. 31, 2019     (GB) ..................................... 1910900

(51) Int. Cl.
| | |
|---|---|
| *C07K 16/32* | (2006.01) |
| *C07K 16/28* | (2006.01) |
| *C07K 16/30* | (2006.01) |
| *C07K 16/46* | (2006.01) |

(52) U.S. Cl.
CPC ...... *C07K 16/2896* (2013.01); *C07K 16/3015* (2013.01); *C07K 16/32* (2013.01); *C07K 16/461* (2013.01); *C07K 2317/24* (2013.01); *C07K 2317/524* (2013.01); *C07K 2317/526* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 2008/0089892 | A1 | 4/2008 | Allan et al. |
| 2010/0015133 | A1 | 1/2010 | Igawa et al. |
| 2011/0123440 | A1 | 5/2011 | Hansen et al. |
| 2016/0215061 | A1 | 7/2016 | Shaheen et al. |
| 2023/0310584 | A1 | 10/2023 | Durrant et al. |

FOREIGN PATENT DOCUMENTS

| | | | | | |
|---|---|---|---|---|---|
| CN | 111333704 | A | 6/2020 | | |
| EP | 0036676 | A1 | 9/1981 | | |
| EP | 0052522 | A2 | 5/1982 | | |
| EP | 0058481 | B1 | 10/1986 | | |
| JP | 2010-522550 | A | 7/2010 | | |
| JP | 2010-279389 | A | 12/2010 | | |
| JP | 2014-530891 | A | 11/2014 | | |
| JP | 2018-524355 | A | 8/2020 | | |
| WO | 8404642 | A1 | 11/1984 | | |
| WO | 9413804 | A1 | 6/1994 | | |
| WO | WO 2005/017148 | A1 | 2/2005 | | |
| WO | 2007005612 | A2 | 1/2007 | | |
| WO | WO 2008/116937 | A2 | 10/2008 | | |
| WO | 2010151792 | A1 | 12/2010 | | |
| WO | 2013004842 | A3 | 4/2013 | | |
| WO | WO 2013/060867 | A1 | 5/2013 | | |
| WO | 2014108198 | A1 | 7/2014 | | |
| WO | 2014145159 | A2 | 9/2014 | | |
| WO | 2014006217 | A9 | 2/2015 | | |
| WO | 2015063500 | A1 | 5/2015 | | |
| WO | WO 2017/006052 | A2 | 1/2017 | | |
| WO | 2017033020 | A1 | 3/2017 | | |
| WO | WO-2017093448 | A1 * | 6/2017 | ............ | C07K 16/30 |
| WO | WO 2017/205742 | A1 | 11/2017 | | |
| WO | WO 2017/218707 | A2 | 12/2017 | | |
| WO | 2018083126 | A1 | 5/2018 | | |
| WO | 2018146317 | A1 | 8/2018 | | |

OTHER PUBLICATIONS

Frontiers in Immunology, vol. 9, Article 1096, p. 1-4, published May 2018 (Year: 2018).*
Frontiers in Immunology, vol. 9, Article 1096, p. 1-4, published May 2018; supplementary material: https://www.frontiersin.org/articles/10.3389/fimmu.2018.01096/full#supplementary-material (Year: 2018).*
Glycobiology, 2018, vol. 28, No. 9, 640â647 (Year: 2018).*
Brentville et al., A novel bivalent DNA vaccine encoding both spike protein receptor-binding domain and nucleocapsid protein of SARS-CoV-2 to elicit T cell and neutralising antibody responses that cross react with variants. Retrieved from the internet: URL: https://www.biorxiv.org/content/10.1101/2021.06.18.448932v1, [retrieved on Nov. 24, 2021], Jun. 18, 2021, 39 pgs.
Piron et al., Boosting in planta production of antigens derived from the porcine reproductive and respiratory syndrome virus (PRRSV) and subsequent evaluation of their immunogenicity. PLoS One. Mar. 10, 2014;9(3):e91386. doi: 10.1371/journal.pone.0091386.

(Continued)

Primary Examiner — Janet L Andres
Assistant Examiner — Imma Barrera
(74) Attorney, Agent, or Firm — Wolf, Greenfield & Sacks, P.C.

(57) ABSTRACT

The present invention relates to the identification of key residues within mouse IgG3 antibodies (mAbs) that are responsible for intermolecular cooperativity and their transfer into IgG1 antibodies in order to enhance their functional affinity and direct a cell killing.

15 Claims, 40 Drawing Sheets
Specification includes a Sequence Listing.

(56) References Cited

OTHER PUBLICATIONS

Vankemmelbeke et al., Abstract A161: Targeting gastrointestinal tumors with constant region engineered anti-glycan antibodies. Cancer Immunology Research. Feb. 1, 2019;7(2_Supplement):A161.

Vankemmelbeke et al., Engineering the Human Fc Region Enables Direct Cell Killing by Cancer Glycan-Targeting Antibodies without the Need for Immune Effector Cells or Complement. Cancer Res. Aug. 15, 2020;80(16):3399-3412. doi: 10.1158/0008-5472.CAN-19-3599. Epub Jun. 12, 2020. Author Manuscript, 30 pages.

Dillon, M. J. et al., "Contribution of murine IgG Fc regions to antibody binding to the capsule of Burkholderia pseudomallei", Virulence, 7(6), DOI: 10.1080/21505594.2016.1176655 external link ISSN:2150-5594, Apr. 20, 2016, 691-701.

Harmer, N. J. et al., "Isotype switching: Mouse IgG3 constant region drives increased affinity for polysaccharide antigens", Virulence, 7(6), DOI: 10.1080/21505594.2016.1193278, May 25, 2016, 623-626.

Holliger, P. et al., ""Diabodies:" small bivalent and bispecific antibody fragments", PNAS USA, 90(14), doi: 10.1073/pnas.90.14.6444, Jul. 15, 1993, 6444-6448.

Huston, J. et al., "Protein Engineering of Antibody Binding Sites: Recovery of Specific Activity in an Anti-Digoxin Single-Chain Fv Analogue Produced in *Escherichia coli*", PNAS USA, 85(16), https://doi.org/10.1073/pnas.85.16.5879, Aug. 1998, 5879-5883.

Traunecker, A. et al., "Bispecific single chain molecules (Janusins) target cytotoxic lymphocytes on HIV infected cells", EMBO J., 10(12), 1991, 3655-3659.

* cited by examiner

Fig1A_comparative cell binding

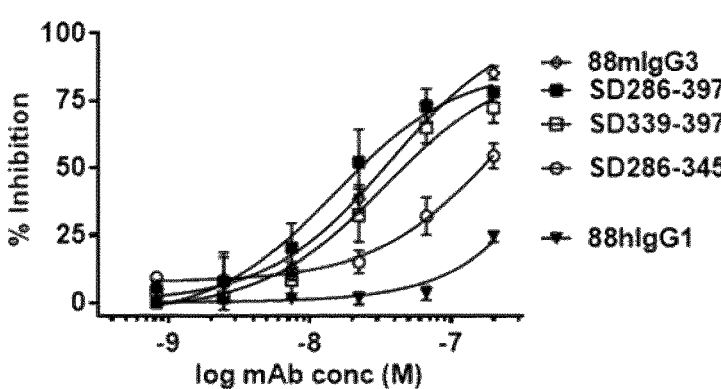
Figure 3D
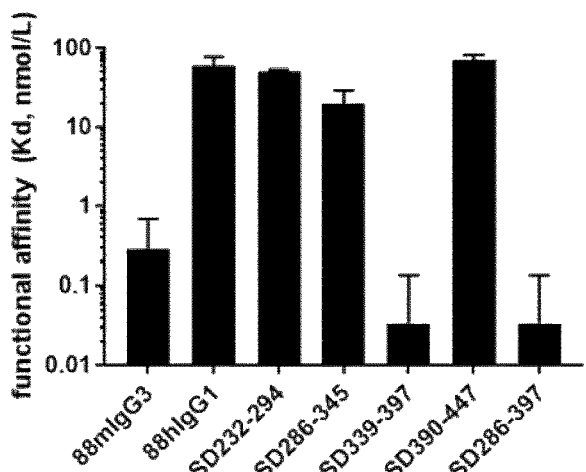
Figure 3E
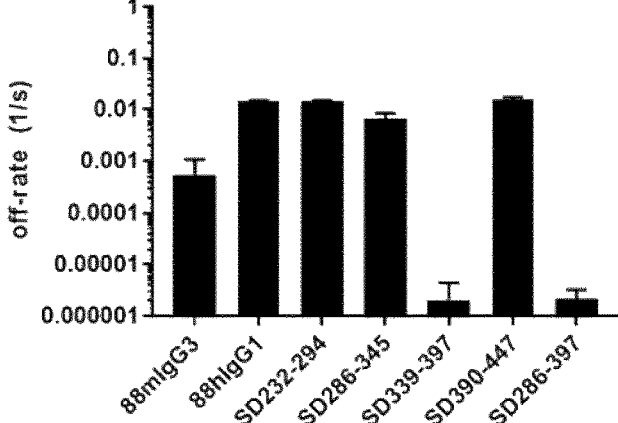
Figure 3F

Figure 5

Colo205

|  Negative control | Positive control | FG27.10 | FG27.18 | |

ST16

HUVECS

PBMCS

|      | fg27.10    | fg27.18    | ch27       | humanised 27 |
|------|------------|------------|------------|--------------|
| Bmax | 594.9      | 2064       | 5888       | 3750         |
| Kd   | 2.396e-008 | 5.934e-008 | 2.191e-007 | 1.62e-007    |

|      | fg27.10    | fg27.18    | ch27         | humanised 27 |
|------|------------|------------|--------------|--------------|
| Bmax | 1126       | 2619       | ~ 60410      | 3639         |
| Kd   | 5.262e-008 | 6.627e-008 | ~ 7.964e-006 | 1.145e-006   |

|      | fg27.10   | fg27.18    | ch27       | humanised 27 |
|------|-----------|------------|------------|--------------|
| Bmax | 497.4     | 492.6      | 3896       | 4747         |
| Kd   | 5.39e-008 | 1.295e-009 | 4.707e-008 | 7.533e-008   |

|      | fg27.10   | fg27.18    | ch27       | humanised 27 |
|------|-----------|------------|------------|--------------|
| Bmax | 663.8     | 1682       | 2442       | 1611         |
| Kd   | 3.17e-008 | 4.052e-008 | 1.777e-007 | 4.217e-007   |

|  | fg27.10 | fg27.18 | ch27 | humanised 27 |
|---|---|---|---|---|
| Bmax | 1126 | 2619 | ~ 60410 | 3639 |
| Kd | 5.262e-008 | 6.627e-008 | ~ 7.964e-006 | 1.145e-008 |

|  | fg27.10 | fg27.18 | ch27 | humanised 27 |
|---|---|---|---|---|
| Bmax | 663.8 | 1682 | 2442 | 1611 |
| Kd | 3.17e-008 | 4.052e-008 | 1.777e-007 | 4.217e-007 |

|  | fg27.10 | fg27.18 | ch27 | humanised 27 |
|---|---|---|---|---|
| Bmax | 1887 | 3662 | 17813 | 6080 |
| Kd | 1.568e-008 | 2.244e-008 | 1.435e-006 | 1.014e-007 |

88 Light chain DNA sequence (variable region + Kappa contant)

Atgagtgtgctcactcaggtcctggcgttgctgctgctgtggcttacaggtgccagatgtgacatccagatgactcagtctccaacctccctatctg
catctgtgggagaaactgtcaccatcacatgtcgaacaagtgagaatattcacaatttttaacatggtatcagcagaaacagggaaaatctcct
caggtcctggtctataatgcaaaaaaccttaccagatggtgtgccatcaaggttcagtggcagtggatcaggaacacaatattctctcaagatcaa
cagcctgcagcctgaagattttgggacttattactgtcaacatttttggagtagtccgtggacgttcggtggaggcaccaagctggaaatcaaa
cgtacggtagcgccatcgtcttcatcttcccgccatctgatgagcagttgaaatctggaa*gcctctgttgtgtgcctgctgaataacttctatcc
cagagaggccaaagtacagtggaaggtggataacgccctccaatcgggtaactcccaggagagtgtcacagagcaggacagcaaggacagc
acctacagcctcagcagcaccctgacgctgagcaaagcagactacgagaaacacaaagtctacgcctgcgaagtcacccatcagggcctgagc
tcgcccgtcacaaagagcttcaacaggggagagtgt (SEQ ID NO: 9)

88 Light chain protein sequence (variable region + Kappa contant)

MSVLTQVLALLLLWLTGARCDIQMTQSPTSLSASVGETVTITCRTSENIHNFLTWYQQKQ
GKSPQVLVYNAKTLPDGVPSRFSGSGSGTQYSLKINSLQ*EDFGTYYCQHFWSSPWTFGG
GTKLEIKRTVAPSVFIFPPSDEQLKSGTASVVCLLNNFYPREAKVQWKVDNALQSGNS*E
SVTEQDSKDSTYSLSSTLTLSKADYEKHKVYACEVTHQGLSSPVTKSFNRGEC (SEQ ID NO: 10)

Heavy chain DNA sequence of i88v1 (variable + 'improved' v1 constant region)

atgtacttgggactgaactgtgtattcatagttttttctcttaaatggtgtccagagtgaagtgaaactcgaggagtctggaggaggcttggtgcaa
cctggaggatccatgaaactctcttgtgctgcctctggattcactttagtgacgcctggatgaactgggtccgccagtctccagagaaggggctt
gagtgggttgctgaaattagaagcaaagttattaatcctgcaatatactatgctgagtctgtgaaagagaggttcaccatattaagagatgattc
caaaagtagtgtctacctgcaaatgaacagcttaagagctgaagacactggaatttattactgttccaggtctactatgattacgacaagggacc
cgtcccggtacttcgatgtctgggcgcagggaccacggtcaccgtctccagcgcttccaccaagggcccatcggtcttccccctggcaccctcc
tccaagagcacctctggggcacagcggccctgggctgcctggtcaaggactacttccccgaaccggtgacggtgtcgtggaactcaggcgccct
gaccagcggcgtgcacaccttcccggctgtcctacagtcctcaggactctactccctcagcagcgtggtgaccgtgccctccagcagcttgggca
cccagacctacatctgcaacgtgaatcacaagcccagcaacaccaaggtggacaagaaagttgagcccaaatcttgtgacaaaactcacacat
gcccaccgtgcccagcacctgaactcctggggggaccgtcagtcttcctcttccccccaaaacccaaggacaccctcatgatctcccggacccct
gaggtcacatgcgtggtggtggacgtgagccacgaagacccc*gaggtcaagttcaactggtacgtggacggcgtggaggtgcatacagcctgg
acacagccccgtgaagagcagtacaacagtacctaccgagtggtcagtgtcctcaccgtcctgcaccaggactggctgaatggcaaggagtac
aagtgcaaggtctccaacaaagccctcccagcccccatcgagaaaaccatctccaaaccaaaggaagagcccagacacctcaagtatacacc
atacccccacctcgtgaacaaatgtccaagaagaaggttagtctgacctgcctggtcaccaacttcttctctgaagccatcagtgtggagtggga
gagcaatgggcagccggagaacaactacaagaccacgcctcccgtgctggactccgacggctccttcttcctctacagcaagctcaccgtggac
aagagcaggtggcagcaggggaacgtcttctcatgctccgtgatgcatgaggctctgcacaaccactacacgcagaagagcctctccctgtctcc
gggtaaa (SEQ ID NO: 11)

Heavy chain Protein sequence of i88v1 (variable + 'improved' v1 constant region)

MYLGLNCVFIVFLLNGVQSEVKLEESGGGLVQPGGSMKLSCAASGFTFSDAWMNWVRQSP
EKGLEWVAEIRSKVINPAIYYAESVKERFTILRDDSKSSVYLQMNSLRAEDTGIYYCSRS
TMITTRDPSRYFDVWGAGTTVTVSSASTKGPSVFPLAPSSKSTSGGTAALGCLVKDYFPE
PVTVSWNSGALTSGVHTF*AVLQSSGLYSLSSVVTVPSSSLGTQTYICNVNHKPSNTKVD
KKVEPKSCDKTHTCPPCPAPELLGGPSVFLFPPKPKDTLMISRTPEVTCVVVDVSHEDPE
VKFNWYVDGVEVHTAWTQPREEQYNSTYRVVSVLTVLHQDWLNGKEYKCKVSNKALPAPI
EKTISKPKGRAQT*QVYTIPPPREQMSKKKVSLTCLVTNFFSEAISVEWESNGQPENNYK
TTPPVLDSDGSFFLYSKLTVDKSRWQQGNVFSCSVMHEALHNHYTQKSLSLSPGK (SEQ ID NO: 12)

Figure 15A

Heavy chain DNA sequence of i88v2 (variable + 'improved' v2 constant region)

Atgtacttgggactgaactgtgtattcatagtttttctcttaaatggtgtccagagtgaagtgaaactcgaggagtctggaggaggcttggtgcaa cctggaggatccatgaaactctcttgtgctgcctctggattcacttttagtgacgcctggatgaactgggtccgccagtctccagagaaggggctt gagtgggttgctgaaattagaagcaaagttattaatcctgcaatatactatgctgagtctgtgaaagagaggttcaccatattaagagatgattc caaaagtagtgtctacctgcaaatgaacagcttaagagctgaagacactggaatttattactgttccaggtctactatgattacgacaagggacc cgtcccggtacttcgatgtctggggcgcagggaccacggtcaccgtctccagcgcttccaccaagggcccatcggtcttccccctggcaccctcct ccaagagcacctctggggggcacagcggccctgggctgcctagtcaaggactacttccccgaaccggtgacggtgtcgtggaactcaggcgccct gaccagcggcgtgcacaccttcccggctgtcctacagtcctcaggactctactccctcagcagcgtggtgaccgtgccctccagcagcttgggca cccagacctacatctgcaacgtgaatcacaagcccagcaacaccaaggtggacaagaaagttgagcccaaatcttgtgacaaaactcacacat gcccaccgtgcccagcacctgaactcctggggggaccgtcagtcttcctcttcccccaaaacccaaggacaccctcatgatctcccggacccct gaggtcacatgcgtggtggtggacgtgagccacgaagaccctgaggtcaagttcaactggtacgtggacggcgtggaggtgcatacagcctgg acacagccccgtgaagagcagtacaacagtacctaccgagtggtcagtgtcctcaccgtcctgcaccaggactggctgaatggcaaggagtac aagtgcaaggtctccaacaaagccctcccagcccccatcgagaaaaccatctccaaagccaaaggaagagcccgaacacctcaagtatacac catcccccatcccgtgatgagctgtccaagaagaaggttagtctgacctgcctggtcaaaaacttctattctgaagccatcagtgtggagtggg agagcaatgggcagccggagaacaactacaagaccacgcctcccgtgctggactccgacggctccttcttcctctacagcaagctcaccgtgga caagagcaggtggcagcaggggaacgtcttctcatgctccgtgatgcatgaggctctgcacaaccactacacgcagaagagcctctccctgtctc cgggtaaa(SEQ ID NO: 13)

Heavy chain protein sequence of i88v2 (variable + 'improved' v2 constant region)

MYLGLNCVFIVFLLNGVQSEVKLEESGGGLVQPGGSMKLSCAASGFTFSDAWMNWVRQSP
EKGLEWVAEIRSKVINPAIYYAESVKERFTILRDDSKSSVYLQMNSLRAEDTGIYYCSRS
TMITTADPSRYFDVWGAGTTVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVD
KKVEPKSCDKTHTCPPCPAPELLGGPSVFLFPPKPKDTLMISRTPEVTCVVVDVSHEDPE
VKFNWYVDGVEVHTAWTQPREEQYNSTYRVVSVLTVLHQDWLNGKEYKCKVSNKALPAPI
EKTISKAKGRARTPQVYTIPPSRDELSKKKVSLTCLVKNFYSEAISVEWESNGQPENNYK
TTPPVLDSDGSFFLYSKLTVDKSRWQQGNVFSCSVMHEALHNHYTQKSLSLSPGK (SEQ ID NO: 14)

Heavy chain DNA sequence of i88v3 (variable + 'improved' v3 constant region)

atgtacttgggactgaactgtgtattcatagtttttctcttaaatggtgtccagagtgaagtgaaactcgaggagtctggaggaggcttggtgcaa cctggaggatccatgaaactctcttgtgctgcctctggattcacttttagtgacgcctggatgaactgggtccgccagtctccagagaaggggctt gagtgggttgctgaaattagaagcaaagttattaatcctgcaatatactatgctgagtctgtgaaagagaggttcaccatattaagagatgattc caaaagtagtgtctacctgcaaatgaacagcttaagagctgaagacactggaatttattactgttccaggtctactatgattacgacaagggacc cgtcccggtacttcgatgtctggggcgcagggaccacggtcaccgtctccagcgcttccaccaagggcccatcggtcttccccctggcaccctcct ccaagagcacctctggggggcacagcggccctgggctgcctggtcaaggactacttccccgaaccggtgacggtgtcgtggaactcaggcgccct gaccagcggcgtgcacaccttcccggctgtcctacagtcctcaggactctactccctcagcagcgtggtgaccgtgccctccagcagcttgggca cccagacctacatctgcaacgtgaatcacaagcccagcaacaccaaggtggacaagaaagttgagcccaaatcttgtgacaaaactcacacat gcccaccgtgcccagcacctgaactcctggggggaccgtcagtcttcctcttcccccaaaacccaaggacaccctcatgatctcccggacccct gaggtcacatgcgtggtggtggacgtgagccacgaagaccctgaggtcaagttcaactggtacgtggacggcgtggaggtgcataatgccaag acaaagccccgtgaagagcagtacaacagtacctaccgagtggtcagtgtcctcaccgtcctgcaccaggactggctgaatggcaaggagtac aagtgcaaggtctccaacaaagccctcccagcccccatcgagaaaaccatctccaaagccaaaggaagagcccgaacacctcaagtatacac cctgcccccatcccgtgatgagctgaccaagaagaaggttagtctgacctgcctggtcaaaggcttctattctagcgccatcgcgtggagtggg agagcaatgggcagccggagaacaactacaagaccacgcctcccgtgctggactccgacggctccttcttcctctacagcaagctcaccgtgga caagagcaggtggcagcaggggaacgtcttctcatgctccgtgatgcatgaggctctgcacaaccactacacgcagaagagcctctccctgtctc caagagcaggtggcagcaggggaacgtcttctcatgctccgtgatgcatgaggctctgcacaaccactacacgcagaagagcctctccctgtctc cgggtaaa (SEQ ID NO: 15)

Figure 15B

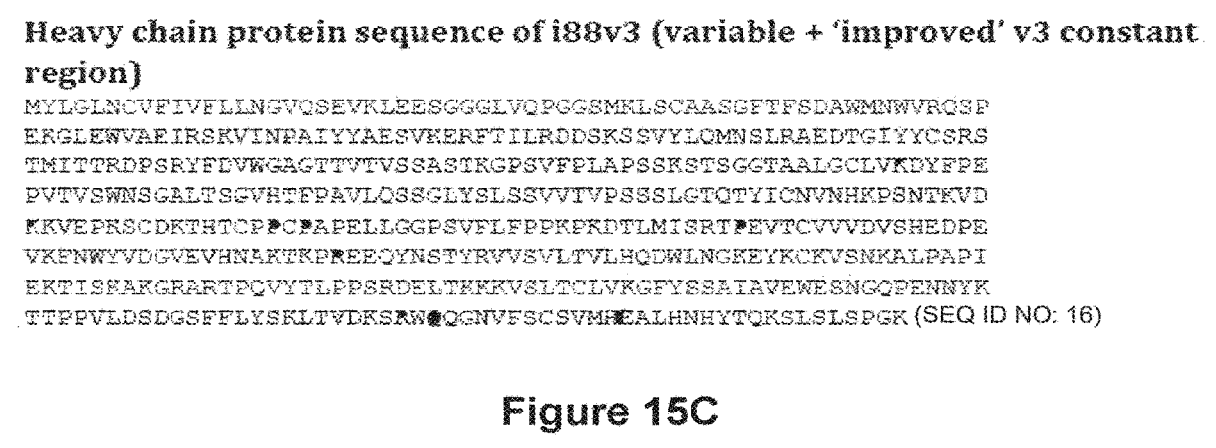

Heavy chain protein sequence of i88v3 (variable + 'improved' v3 constant region)

MYLGLNCVFIVFLLNGVQSEVKLEESGGGLVQPGGSMKLSCAASGFTFSDAWMNWVRQSP
ERGLEWVAEIRSKVINPAIYYAESVKERFTILRDDSKSSVYLQMNSLRAEDTGIYYCSRS
TMITTRDPSRYFDVWGAGTTVTVSSASTKGPSVFPLAPSSKSTSGGTAALGCLVKDYFPE
PVTVSWNSGALTSGVHTFPAVLQSSGLYSLSSVVTVPSSSLGTQTYICNVNHKPSNTKVD
KKVEPKSCDKTHTCPPCPAPELLGGPSVFLFPPKPKDTLMISRTPEVTCVVVDVSHEDPE
VKFNWYVDGVEVHNAKTKPREEQYNSTYRVVSVLTVLHQDWLNGKEYKCKVSNKALPAPI
EKTISKAKGRARTPQVYTLPPSRDELTKKKVSLTCLVKGFYSSAIAVEWESNGQPENNYK
TTPPVLDSDGSFFLYSKLTVDKSRWQQGNVFSCSVMHEALHNHYTQKSLSLSPGK (SEQ ID NO: 16)

Figure 15C

129 Light chain DNA sequence (variable region + Kappa contant)

atggaatcacagactcaggtcctaatgtccctgctgttctgggtatctacctgtggggacattgtgatgacacagtctccatcctccctgactgtga cagcaggagagaaggtcactatgagctgcaagtccagtcagagtctgttaaacagtggaaatcaaaagaactacttgacctggtaccagcaga aaccagggcagcctcctaaagtgttgatctactgggcatccactagggaatctggggtccctgatcgcttcacaggcagtggatctggaacagat ttcactctcaccatcagcagtgtgcaggctgaagacctggcagtttattactgtcagaatgattatagttctccatcacgttcggctcggggacaa agttggaaataaaacgtacggtagcggccccatctgtcttcatcttcccgccatctgatgagcagttgaaatctggaactgcctctgttgtgtgcct gctgaataacttctatcccagagaggccaaagtacagtggaaggtggataacgccctccaatcgggtaactcccaggagagtgtcacagagca ggacagcaaggacagcacctacagcctcagcagcaccctgacgctgagcaaagcagactacgagaaacacaaagtctacgcctgcgaagtca cccatcagggcctgagctcgcccgtcacaaagagcttcaacaggggagagtgt (SEQ ID NO: 17)

129 Light chain protein sequence (variable region + Kappa contant)

MESQTQVLMSLLFWVSICGDIVMTQSPSSLTVTAGEKVTMSCKSSQSLLNSGNQKNYLTW

YQQKPGQPPKVLIYWASTRESGVPDRFTGSGSGTDFTLTISSVQAEDLAVYYCQNDYSSP

FTFGSGIKLEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC (SEQ ID NO: 18)

Heavy chain DNA sequence of i129v1 (variable + 'improved' v1 constant region)

Atgctgttggggctgaagtgggtttttcttgttgttgttttttatcaaggtgtgcattgtgaggtgcagcttgttgagtctggtggaggattggtgcagcct aaagggtcattgaaactctcatgtgcagcctctggattcaccttcaatacctacgccatgaactgggtccgccaggctccaggaaagggttgga atgggttgctcgcataagaagtaaaagtaataattatgcaacatattatgccgattcagtgaaagacaggttcaccatatccagagatgattcac aaagcatgctctatctgcaaatgaacaacttgaaaaaggaggacacagccatgtattactgtgtaggggtacggtagtggggggaaactactggg gtcaaggaacctcagtcaccgtctccagcgcttccaccaagggcccatcggtcttccccctggcaccctcctccaagagcacctctgggggcaca gcggccctgggctgcctggtcaaggactacttccccgaaccggtgacggtgtcgtggaactcaggcgccctgaccagcggcgtgcacaccttccc ggctgtcctacagtcctcaggactctactccctcagcagcgtggtgaccgtgccctccagcagcttgggcacccagacctacatctgcaacgtga atcacaagcccagcaacaccaaggtggacaagaaagttgagcccaaatcttgtgacaaaactcacacatgcccaccgtgcccagcacctgaac tcctggggggaccgtcagtcttcctcttccccccaaaacccaaggacacccctcatgatctcccggacccctgaggtcacatgcgtggtggtggac gtgagccacgaagaccctgaggtcaagttcaactggtacgtggacggcgtggaggtgcatacagcctggacacagcccgtgaagagcagtac aacagtacctacgagtggtcagtgtcctcaccgtcctgcaccaggactggctgaaggcaaggagtacaagtgcaaggtctccaacaaagccc tcccagcccccatcgagaaaaccatctccaaacccaaaggaagagcccagacacctcaagtatacaccatacccccacctcgtgaacaaatgt ccaagaagaaggttagtctgacctgcctggtcaccaacttcttctcgaagccatcagtgtggagtgggagagcaatgggcagccggagaacaa ctacaagaccacgcctcccgtgctggactcgacggctcttcttcctctacagcaagctcaccgtggacaagagcaggtggcagcaggggaac gtcttctcatgctccgtgatgcatgaggctctgcacaaccactacacgcagaagagcctctccctgtctccgggtaaa (SEQ ID NO: 19)

Heavy chain Protein sequence of i129v1 (variable + 'improved' v1 constant region)

MLLGLKWVFFVVFYQGVHCEVQLVESGGGLVQPKGSLKLSCAASGFTFNTYAMNWVRQAP

GKGLEWVARIRSKSNNYATYYADSVKDRFTISRDDSQSMLYLQMNNLKKEDTAMYYCVGY

GSGGNYWGQGTSVTVSS

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHTAWTQPREEQYN

STYRVVSVLTVLHQDWLNGKEYKCKVSNKALPAPIEKTISKPKGPAQTPQVYTIPPPREQ

MSKKKVSLTCLVTNFFSEAISVEWESNGQPENNYKTTPPVLDSDGSFFLYSKLTVDKSRW

QQGNVFSCSVMHEALHNHYTQKSLSLSPGK (SEQ ID NO: 20)

Figure 16A

Heavy chain DNA sequence of i129v2 (variable + 'improved' v2 constant region)

Atgctgttggggctgaagtgggtttttctttgttgtttttatcaaggtgtgcattgtgaggtgcagcttgttgagtctggtggaggattggtgcagcct aaaggggtcattgaaactctcatgtgcagcctctggattcaccttcaatacctacgccatgaactgggtccgccaggctccaggaaagggtttgga atgggttgctcgcataagaagtaaaagtaataattatgcaacatattatgccgattcagtgaaagacaggttcaccatatccagagatgattcac aaagcatgctctatctgcaaatgaacaacttgaaaaaggaggacacagccatgtattactgtgtagggtacggtagtggggggaaactactggg gtcaaggaacctcagtcaccgtctccagcgcttccaccaagggcccatcggtcttccccctggcaccctcctccaagagcacctctggggggcaca gcggccctgggctgcctggtcaaggactacttccccgaaccggtgacggtgtcgtggaactcaggcgccctgaccagcggcgtgcacaccttccc ggctgtcctacagtcctcaggactctactccctcagcagcgtggtgaccgtgccctccagcagcttgggcacccagacctacatctgcaacgtga atcacaagcccagcaacaccaaggtggacaagaaagttgagcccaaatcttgtgacaaaactcacacatgcccaccgtgcccagcacctgaac tcctggggggaccgtcagtcttcctcttccccccaaaacccaaggacaccctcatgatctcccggacccctgaggtcacatgcgtggtggtggac gtgagccacgaagaccctgaggtcaagttcaactggtacgtggacggcgtggaggtgcatacagcctggacacagcccgtgaagagcagtac aacagtacctaccgagtggtcagtgtcctcaccgtcctgcaccaggactggctgaatggcaaggagtacaagtgcaaggtctccaacaaagccc tcccagcccccatcgagaaaaccatctccaaagccaaaggaagagcccgaacacctcaagtatacaccatacccccatccgtgatgagctgtc aagaagaaggttagtctgacctgcctggtcaaaaactttctattctgaagccatcagtgtggagtgggagagcaatgggcagccggagaacaa ctacaagaccacgcctcccgtgctggactccgacggctccttcttcctctacagcaagctcaccgtggaaagagcaggtggcagcaggggaac gtcttctcatgctccgtgatgcatgaggtctgcacaaccactacacgcagaagagcctctccctgtctccgggtaaa (SEQ ID NO: 21)

Heavy chain Protein sequence of i129v2 (variable + 'improved' v2 constant region)

MLLGLKWVFFVVFYQGVHCEVQLVESGGGLVQPKGSLKLSCAASGFTFNTYAMNWVRQAP
GKGLEWVARIRSKSNNYATYYADSVKDRFTISRDDSQSMLYLQMNNLKKEDTAMYYCVGY
GSGGNYWEQGTSVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHTAWTQPREEQYN
STYRVVSVLTVLHQDWLNGKEYKCKVSNKALPAPIEKTISKAKGRAPPQVYTIPPSRDE
LSKKKVSLTCLVKNFYSEAISVEWESNGQPENNYKTTPPVLDSDGSFFLYSKLTVDKSPW
QQGNVFSCSVMHEALHNHYTQKSLSLSPGK (SEQ ID NO: 22)

Heavy chain DNA sequence of i129v3 (variable + 'improved' v3 constant region)

Atgctgttggggctgaagtgggtttctttgttgtttttatcaaggtgtgcattgtgaggtgcagcttgttgagtctggtggaggattggtgcagcct aaagggtcattgaaactctatgtgcagcctctggattcaccttcaatacctacgccatgaactgggtcgccaggctccaggaaagggtttgga atgggttgctcgcataagaagtaaaagtaataattatgcaacatattatgccgattcagtgaaagacaggttcaccatatccagagatgattcac aaagatgctctatctgcaaatgaacaacttgaaaaaggaggacacagccatgtattactgtgtagggtacggtagtggggggaaactactggg gtcaaggaacctcagtcaccgtctccagcgcttccaccaagggcccatcggtcttccccctggcaccctcctccaagagcacctctggggggcaca gcggccctgggctgcctggtcaaggactacttccccgaacggtgacggtgtcgtggaactcaggcgccctgacagcggcgtgcacaccttccc ggctgtcctacagtcctcaggactctactccctcagcagcgtggtgaccgtgccctccagcagcttgggcacccagacctacatctgcaacgtga atcacaagcccagcaacaccaaggtggacaagaaagttgagcccaaatcttgtgacaaaactcacacatgcccaccgtgccagcacctgaac tcctggggggaccgtcagtcttcctcttccccccaaaacccaaggacaccctcatgatctcccggacccctgaggtcacatgcgtggtggtggac gtgagccacgaagaccctgaggtcaagttcaactggtacgtggacggcgtggaggtgcataatgccaagacaaagcccgtgaagagcagta caacagtacctaccgagtggtcagtgtcctcaccgtcctgcaccaggactggctgaatggcaaggagtacaagtgcaaggtctccaacaaagcc ctcccagcccccatcgagaaaaccatctccaaagccaaaggaagagcccgaacacctcaagtatacaccctgcccccatcccgtgatgagctg accaagaagaaggttagtctgacctgcctggtcaaaggcttctattctagcgccatcgccgtggagtgggagagcaatgggcagccggagaac aactacaagaccacgcctcccgtgctggactccgaaggctccttcttcctctacagcaagctcaccgtggacaagagcaggtggcagcaggggga acgtcttctcatgctccgtgatgcatgaggctctgcacaaccactacacgcagaagagcctctccctgtctccgggtaaa (SEQ ID NO: 23)

Figure 16B

Heavy chain Protein sequence of i129v3 (variable + 'improved' v3 constant region)

MLLGLKWVFFVVFYQGVHCEVQLVESGGGLVQPKGSLRLSCAASGFIFNYYAMNWVRQAP
GKGLEWVARIRSKSNNYATYYADSVKDRFTISRDDSQSMLYLQMNNLKREDTAMYYCVGY
GSGGNYWGQGTSVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQARTPQVYTLPPSRDE
LTKKKVSLTCLVKGFYSSAIAVEWESNGQPENNYKTIPPVLDSDGSFFLYSKLTVDKSRW
QQGNVFSCSVMHEALHNHYTQKSLSLSPGK (SEQ ID NO: 24)

Figure 16C

27 Light chain DNA sequence (variable region + Kappa contant)

atgaagttgcctgttaggctgttggtgctgatgttctggattcctgcttccatcagtgatgtttttgatgacccaaactccactctccctgcctgtcagt
cttggagatcaagcctccatctcttgcagatctagtcagatcattgtacatactaatggaaacacctatttagaatggtacctgcagaaaccaggc
cagtctcca aacctcctgatctacaaagtttccaaccgattttctggggtcccagacaggttcagtggcagtggatcagggacagatttcacactc
aagatcagcagagtggaggctgaggatctggagtttattactgctttcaaggttcacatgttccattcacgttcggctcggggacaaagttgga
aataaaacgtacggtagcggccccatctgtcttcatcttcccgccatctgatgagcagttgaaatctggaactgcctctgttgtgtgcctgctgaat
aacttctatcccagagaggccaaagtacagtggaaggtggataacgccctccaatcgggtaactcccaggagagtgtcacagagcaggacagc
aaggacagcacctacagcctcagcagcacccctgacgctgagcaaagcagactacgagaaacacaaagtctacgcctgcgaagtcacccatca
gggcctgagctcgcccgtcacaaagagcttcaacaggggagagtgt (SEQ ID NO: 25)

27 Light chain protein sequence (variable region + Kappa contant)

MKLPVRLLVLMFWIPASISDVLMTQTPLSLPVSLGDQASISCRSSQIIVHTNGNTYLEWYL
QKPGQSPNLLIYKVSNRFSGVPDRFSGSGSGTDFTLKISRVEAEDLGVYYCFQGSHVPFTF
GSGTKLEIKRTVAAPSVFIFPPSDEQLKSGTASVVCLLNNFYPREAKVQWKVDNALQSGNS
QESVTEQDSKDSTYSLSSTLTLSKADYEKHKVYACEVTHQGLSSPVTKSFNRGEC (SEQ ID NO: 26)

Heavy chain DNA sequence of i27v1 (variable + 'improved' v1 constant region)

atgaacttctggctcagcttgattttccttgtccttgttttaaaaggtgtccagtgtgaagtgaagctggtggagtctggggggaggcttagtgcagc
ctggagggtccctgaaactctcctgtgcaacctctggattcactttcagtcactattacatgtattgggttcgccagactccagagaagaggctgg
agtgggtcgcatacattagtaatgatggtgataacacctattatccagacactataaggggccgattcaccatctccagagacaatgccaggaa
caccctgtacctgcaaatgagccgtctgaagtctgaggacacagccatgtattactgtgcaagagggaagtacgacggggcctggtttgcttact
ggggccaagggactctggtcactgtctctagcgcttccaccaagggcccatcggtcttccccctggcaccctcctccaagagcacctctggggc
acagcggccctgggctgcctggtcaaggactacttcccccgaaccggtgacggtgtcgtggaactcaggcgccctgaccagcggcgtgcacacct
tcccggctgtcctacagtcctcaggactctactccctcagcagcgtggtgaccgtgccctccagcagcttgggcacccagacctacatctgcaacg
tgaatcacaagcccagcaacaccaaggtggacaagaaagttgagcccaaatcttgtgacaaaactcacacatgcccaccgtgcccagcacctg
aactcctggggggaccgtcagtcttcctcttccccccaaaacccaaggacaccctcatgatctccggacccctgaggtcacatgcgtggtggtg
gacgtgagccacgaagaccctgaggtcaagttcaactggtacgtggacggcgtggaggtgcatacagcctggacagcccgtgaagagca
gtacaacagtacctaccgagtggtcagtgtcctcaccgtcctgcaccaggactggctgaatggcaaggagtacaagtgcaaggtctccaacaaa
gccctcccagcccccatcgagaaaaccatctccaaacccaaaggaagagcccagacacctcaagtatacaccataccccaccctcgtgaacaa
atgtccaagaagaaggttagtctgacctgcctggtcaccaacttcttctctgaagccatcagtgtggagtgggagagcaatgggcagccggaga
acaactacaagaccacgcctcccgtgctggactccgacggctccttcttcctctacagcaagctcaccgtggacaagagcaggtggcagcaggg
gaacgtcttctcatgctccgtgatgcatgaggctctgcacaaccactacacgcagaagagcctctccctgtctccgggtaaa (SEQ ID NO: 27)

Heavy chain Protein sequence of i27v1 (variable + 'improved' v1 constant region)

MNFWLSLIFLVLVLKGVQCEVKLVESGGGLVQPGGSLKLSCATSGFTFSHYYMYWVRQTP
EKRLEWVAYISNDGDNTYYPDTIRGRFTISRDNARNTLYLQMSRLKSEDTAMYYCARGKY
DGAWFAYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHTAWTQPREEQYN
STYRVVSVLTVLHQDWLNGKEYKCKVSNKALPAPIEKTISKPKGRAQTPQVYTIPPPREQ
MSKKKVSLTCLVTNFFSEAISVEWESNGQPENNYKTTPPVLDSDGSFFLYSKLTVDKSRW
QQGNVFSCSVMHEALHNHYTQKSLSLSPGK (SEQ ID NO: 28)

Figure 17

MDA_MB231

BT474 PI uptake

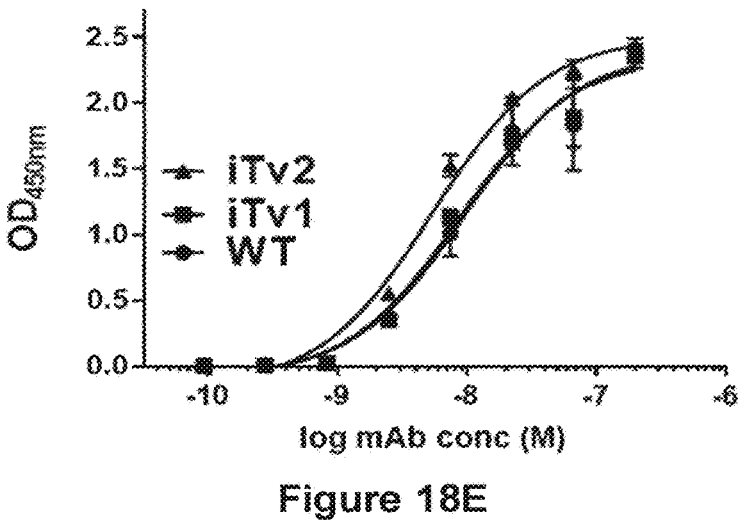

Figure 18E

Heavy chain protein sequence of 'i'trastuzumab v1 and v2 (variable and 'improved' v1 and v2 constant region)

Light chain protein sequence of iTrastuzumabv1 and
iTrastuzumabv2
DIQMTQSPSSLSASVGDRVTITCRASQDVNTAVAWYQQKPGKAPKLLIYSASFLYSGVPS
RFSGSRSGTDFTLTISSLQPEDFATYYCQQHYTTPPTFGQGTKVEIKRTVAAPSVFIFPP
SDEQLKSGTASVVCLLNNFYPREAKVQWKVDNALQSGNSQESVTEQDSKDSTYSLSSTLT
LSKADYEKHKVYACEVTHQGLSSPVTKSFNRGEC (SEQ ID NO: 29)

Heavy chain protein sequence of iTrastuzumabv1
EVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHTAWTQPREEQYN
STYRVVSVLTVLHQDWLNGKEYKCKVSNKALPAPIEKTISKPKGRAQTPQVYTIPPPREQ
MSKKKVSLTCLVTNFFSEAISVEWESNGQPENNYKTTPPVLDSDGSFFLYSKLTVDKSRW
QQGNVFSCSVMHEALHNHYTQKSLSLSPGK (SEQ ID NO: 30)

Heavy chain protein sequence of iTrastuzumabv2
EVQLVESGGGLVQPGGSLRLSCAASGFNIKDTYIHWVRQAPGKGLEWVARIYPTNGYTRY
ADSVKGRFTISADTSKNTAYLQMNSLRAEDTAVYYCSRWGGDGFYAMDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHTAWTQPREEQYN
STYRVVSVLTVLHQDWLNGKEYKCKVSNKALPAPIEKTISKAKGRARTPQVYTIPPSRDE
LSKKKVSLTCLVKNFYSEAISVEWESNGQPENNYKTTPPVLDSDGSFFLYSKLTVDKSRW
QQGNVFSCSVMHEALHNHYTQKSLSLSPGK (SEQ ID NO: 31)

Figure 19

(SEQ ID NO: 32)

|286-378|hIgg1   NAKTKPREEQYNSTYRVVSVLTVLHQDWLNGKEYKCKVSNKALPAPIEKTISKAKGQPREPQVYTLPPSRDELTKNQVSLTCLVKGFYPSDIA

|286-378|mIgG3   TAWTQPREEQINSTFRVVSALPIQHQDWMRGKEFKCKVNNKALPAPIERTISKPKGRAQTPQVYTLPPPREQMSKKKVSLTCLVTNFFSEAIS (SEQ ID NO: 33)

. :* . *: **: ** * . . ; . * :  ; * . * ; * * . *: *: ; *** ; *. .

cluster 1: 294-315 cluster 2: 365-378

| Subdomain | IEDB analysis: human sequence compared to mouse sequence   Score < 1: strong MHCII binder; score 1-10: weak MHCII binder | IEDB analysis after reversion of selected mIgG3 residues (individual boxes in alignment, underlined in table) back to human sequence |
|---|---|---|
| SD286-306 DII | FRVVSALTV - DR104 (0.96), DR0401 (1.5), DR0701 (0.03), DR0801 (1.4), DR1501 (3.5), DR1301 (5.9)(SEQ ID NO: 34) | YRVVSVLTV – now identical to human sequence, so any T cells will be tolerized to this epitope (SEQ ID NO: 38) |
| DII | TFRVVSALT - DR0701 (0.09)(SEQ ID NO: 35) | |
| | VVSALTVLH - DR0301 (3.3), DR0401 (4.22)(SEQ ID NO: 36) | |
| | LVLHQDWLN-DR0301 (1.81) (SEQ ID NO: 37) | |
| SD286-306 DII | AQYNSTFRV- Dr0701 (0.1) (SEQ ID NO: 39) | EQYNSTYRV– now identical to human sequence, so any T cells will be tolerized to this epitope (SEQ ID NO: 40) |
| SD339-378 DII | LTCLVTNFF-DR0401 (4.44) (SEQ ID NO: 41) | LTCLVTGFF – no DR0401 epitope (SEQ ID NO: 42) |
| SD339-378 DII | VYTLPPPRE-DR1101 (6.64) (SEQ ID NO: 43) | VYTLPPPRE- no DR1101 (SEQ ID NO: 44) |

Figure 20

MODIFIED FC-REGIONS TO ENHANCE FUNCTIONAL AFFINITY OF ANTIBODIES AND ANTIGEN BINDING FRAGMENTS THEREOF

RELATED APPLICATIONS

This application is a national stage filing under 35 U.S.C. § 371 of international patent application no. PCT/EP2020/071724, filed Jul. 31, 2020, which claims the benefit of priority under 35 U.S.C. § 119 or 365 of United Kingdom application number 1910900.8, filed Jul. 31, 2019. The contents of these applications are incorporated herein by reference in their entireties.

REFERENCE TO AN ELECTRONIC SEQUENCE LISTING

The contents of the electronic sequence listing (S223970003US00-SUBSEQ-ZJG.xml; Size: 79,231 bytes; and Date of Creation: Oct. 5, 2025) are herein incorporated by reference in their entirety.

SUMMARY

The present invention relates to the identification of key residues within mouse IgG3 antibodies (mAbs) that are responsible for intermolecular cooperativity and their transfer into IgG1 antibodies in order to enhance their functional affinity and direct cell killing.

BACKGROUND

Mouse (m) IgG3 is highly protective against bacterial infection and is the only isotype among the mIgGs that forms non-covalent oligomers, strongly influencing their biological activity (Abdelmoula et al. 1989), and increasing functional affinity to polyvalent antigens. The tendency of mIgG3 oligomerisation was initially identified by Grey et al. (Grey, Hirst, and Cohn 1971) who showed that binding to multivalent antigens promoted mIgG3 intermolecular interactions, which resulted in increased functional affinity to antigen (Greenspan, Monafo, and Davie 1987; Greenspan and Cooper 1993), a characteristic termed 'intermolecular cooperativity' (Greenspan and Cooper 1993; Greenspan, Dacek, and Cooper 1989; Greenspan and Cooper 1992). It was determined the phenomenon depended on Fc as IgG3 F(ab')2 fragments did not bind to the antigen cooperatively (Greenspan, Monafo, and Davie 1987). The mIgG3 isotype is associated with a propensity for intermolecular cooperativity on repetitive antigen, whereby the low monovalent affinity is rescued by avidity-mediated enhanced binding (Greenspan and Cooper 1993, 1992). Non-covalent interactions between adjacent mIgG3 Fc regions are thought to underpin this increased functional affinity, via prolonging target occupancy and reducing dissociation rates (Cooper et al. 1991; Greenspan, Dacek, and Cooper 1989).

The tumour glycome is a rich and under-explored source of cancer-specific targets for mAb development due to the alterations associated with the transformation process (Pinho and Reis 2015). Glycan structures are present on both protein and glycolipid backbones and can be massively over-expressed in cancer due to the altered expression of glycotransferases. Glycans have been shown to be key co-accessory molecules for cancer cell survival, proliferation, dissemination and immune evasion; crosslinking these antigens can lead to direct cell death without the need for immune effector cells or complement (Dalziel et al. 2014; Rodriguez, Schetters, and van Kooyk 2018; Rabu et al. 2012). Indeed, the inventors have generated a number of glycan-targeting mAbs with potential application for cancer therapeutics due to their strong differential tumour versus healthy tissue binding, high functional affinity and their ability to cure mice of metastatic colorectal cancer (Chua et al. 2015; Durrant et al. 2006; Noble et al. 2013), a number of other mAbs are in clinical development as passive or active immunotherapy, or reformatted for chimeric antigen receptor (CAR) T cells (Burris et al. 2010; Labrada et al. 2018; Hege et al. 2017) whilst Dinutuximab beta, an anti-GD2 mAb, is currently used for the treatment of neuroblastoma (Ladenstein et al. 2018). The inventors have previously described a panel of cancer glycan targeting mAbs with Lewis$^{a/c/x}$, Lewis$^{y}$, as well as sialyl-di-Lewis$^{a}$ reactivity (WO2017/033020A1; WO2015/063500A1; Chua et al. 2015; Noble et al. 2013). Intriguingly, if the glycan-binding mAbs were of the mIgG3 isotype they exhibit a direct cytotoxic effect on high-density target expressing cancer cells, independent of the presence of complement or immune effector cells, with the potential to initiate an adaptive anti-tumour immune response and long-term tumour control. This suggested that the intermolecular co-cooperativity enabled by the mIgG3 isotype was responsible for the direct cell killing. This direct cytotoxic ability has also been observed for other anti-glycan mAbs and typically involves mAb-induced homotypic cellular adhesion, cyto-skeletal rearrangement followed by cell swelling, membrane lesions and eventual cellular demise (Loo et al. 2007; Faraj et al. 2017; Roque-Navarro et al. 2008; Chua et al. 2015; Welt et al. 1987). In most cases the cell death is a form of non-classical apoptosis, potentially involving the generation of reactive oxygen species (ROS) generation, most closely resembling oncotic necrosis (Zheng et al. 2017; Hernandez et al. 2011). Importantly, akin to immunogenic or inflammatory cell death (ICD), the coinciding release of in inflammatory mediators—damage associated molecular patterns (DAMPs)—has the potential to recruit innate immune cells to the tumour site that may further increase mAb-mediated effector functions (Galluzzi et al. 2017). Thus, these anti-glycan mAbs can be important tools to remobilise the full potential of the immune system in an otherwise immuno-suppressive environment.

For human antibody therapeutics, the areas not responsible for target specificity are typically replaced with their human equivalent, to generate a humanised version of the antibody which is clinically useful. When we chimerised our mouse mAbs to IgG1 (e.g. human IgG1, hIgG1) they lost direct cell killing and had reduced functional affinity as intermolecular cooperativity is not present in human IgGs. It has previously been suggested that mouse IgG3 antibodies might combine together once bound to their target, in a way other antibody subclasses do not, to stabilise binding and amplify the clinical potency of the antibody.

US2011/0123440 describes altered antibody Fc-regions and the uses thereof. The altered Fc-regions have one or more amino acid substitutions. This patent claims any substitution at many sites but the exact examples are all different substitutions to our invention exemplifying these substitutions are not responsible for direct cell killing.

US2008/0089892 describes polypeptide Fc-region variants and compositions comprising these Fc-region variants with amino acid substitutions in positions 251, 256, 268, 280, 332, 378 and 440 to improve ADCC. The only similarity with the modifications outlined in this patent was position 378 but we substitute it with a serine rather than an aspartic acid and we show decreased ADCC.

US2010/0184959 describes methods of providing an Fc polypeptide variant with 2 or more amino acid substitutions and altered recognition of an Fc ligand (e.g. FcγR or C1q) and/or effector function (e.g. ADCC). In contrast our substitutions are only related to increased cell killing. The presently disclosed 26 and 23 amino acid motifs do include V305A, Q342R R344Q substitutions whereas the 15 amino acid motif only contains Q342R.

US2010/015133 describes methods of producing polypeptides by regulating polypeptide association. They claim changing the charge of paired amino acids from negative to positive charge or the reverse in the CH3 constant region of an antibody at position 356/439, 357/370 and 399/409. In contrast this patent described changing amino acid 356 from aspartic acid (D) to glutamic acid (E) which does not change charge and amino acid 357 from Glutamic acid (E) to Glutamine (Q) which changes a negative charge to neutral and amino acid 370 from lysine (K) to threonine which changes a negative charge to neutral.

WO2018/146317 describes polypeptides and antibodies having an Fc region and an antigen-binding region where the Fc region has an Fc-Fc enhancing mutation and a C1q binding-enhancing mutation providing for polypeptide or antibodies with increased CDC activity and/or agonistic activity. The Fc region is said to comprise (a) a substitution at a position selected from the group consisting of: E430, E345 or a S440Y or S440W substitution, and (b) a substitution at one or more position(s) selected from the group consisting of: G236, S239, S267, H268, S324, K326, I332, E333 and P396 wherein the positions correspond to human IgG1. The polypeptide comprises at least one substitution from the group consisting of: E430G, E345K, E430S, E430F, E430T, E3450, E345R, E345Y, S440Y and S440W. The present invention does not include any of these substitutions.

WO2018/083126 describes polypeptides and antibodies comprising a variant Fc region. The Fc region provides for stabilised Fc:Fc interactions when the polypeptide(s), antibody or antibodies are bound to its target, antigen or antigens on the surface of a cell, while at the same time also having decreased complement-dependent cytotoxicity (CDC) and may also have decreased activation of other effector functions resulting from one or more amino acid modifications in the Fc region. The Fc region is said to comprise a (i) first mutation at E430, E345 or S440, with the proviso that the mutation in S440 is S440Y or S440W; and a (ii) second mutation at K322 or P329. The first mutation is selected from the group consisting of: E430G, E345K, E430S, E430F, E430T, E345Q, E345R, E345Y, S440W and S440Y. The present invention does not include any of these substitutions.

WO2014/108198 discloses polypeptides such as antibodies comprising variant Fc regions having one or more amino acid modifications resulting in increased complement-dependent cytotoxicity (CDC). The present invention does not include any of these substitutions.

WO2013/004842 describes polypeptides and related antibodies comprising a variant Fc domain for stabilising Fc:Fc interactions when the polypeptide(s), antibody or antibodies are bound to its target on the cell surface for improved effector functions, such as CDC responses. The present invention does not include any of these substitutions.

SUMMARY OF THE INVENTION

The present invention provides polypeptides, antibodies, variants and antigen-binding fragments thereof having enhanced functional affinity compared to its parent polypeptide, antibody, variant and antigen-binding fragment thereof. The present invention also provides polypeptides, antibodies, variants and antigen-binding fragments thereof having enhanced cell killing compared to its parent polypeptide, antibody, variant and antigen-binding fragment thereof. Without being limited to theory, it is believed that such modified polypeptides, antibodies, variants and antigen-binding fragments thereof are capable of more stable binding interactions between the Fc regions of two antibodies, thereby providing increased functional affinity of antibody-antigen-binding. Further, the inventors disclose a discontinuous region within the mIgG3 CH2 and CH3 domains that endows this isotype with increased functional affinity, on binding repeating glycan antigen, as well as direct cytotoxicity on high-binding cancer cell lines. Transfer of the involved residues into the IgG1 isotype, creates an improved 'i'IgG1 with increased in vitro and in vivo anti-tumour activity.

By crosslinking chimeric mAbs with anti-human Ig antiserum or by changing one key amino acid residue we demonstrated that direct cell killing is directly related to functional affinity. Further, we recapitulated the functional affinity of our novel, mouse mAbs by introducing intermolecular cooperativity in the chimeric constructs. No one has mapped the mIgG3 cooperativity and the key amino acids that differ between IgG1 and mIgG3 have not been described previously. Thus, the inventors not only instigated the development of our series of anti-glycolipid mAbs but developed a technology which has utility to improve the therapeutic index of any mAb.

Chimerisation of the mIgG3 mAbs onto a human IgG1 backbone coincided with a dramatic reduction in direct cytotoxicity, leading the inventors to hypothesize that this was the result of diminished intermolecular cooperativity. Consequently, the inventors looked to identify the key residues within mIgG3 that are responsible for intermolecular cooperativity and transfer them into IgG1 in order to recapitulate the mIgG3-observed direct cytotoxic activity, thereby creating a chimeric IgG1 with superior clinical utility.

The creation of IgG1 anti-glycan mAbs with increased functional affinity and direct cytotoxic activity through the transfer of selected mIgG3 constant region residues was undertaken by the inventors, utilising our panel or previously generated glycan targeting mAbs. mIgG3 contributing regions were identified through the creation of hybrid IgG1 constructs, containing mIgG3 CH1, CH2 or CH3 domains. Candidate residues were identified through screens based on increased direct cytotoxicity and functional affinity, when introduced into IgG1 (gain-of-function), and/or decreased direct cytotoxicity and functional affinity when replaced by the respective IgG1 residues in mIgG3 (loss-of-function). Preliminary analyses ascertained that mIgG3 CH1 had a negligible contribution to the direct cytotoxicity ability as introducing mIgG3 CH1 into IgG1 did not lead to a significant increase in cytotoxicity. Conversely, introducing human IgG1 (hIgG1) CH1 into mIgG3, equally, did not instigate a significant reduction in killing activity. Next, in a gain-of-function approach, the mIgG3 CH2 and CH3 domains, separately, were introduced in IgG1. IgG1 containing murine CH3 exhibited a significant increase in cytotoxicity. Introducing murine CH2 into IgG1 led to small, but not significant, increase in killing activity. As a confirmation of the contributions made by both domains, the reverse strategy was followed whereby a loss of cytotoxicity activity was evaluated due to the introduction IgG1 CH2 or CH3 domains into mIgG3. This scenario led to a significant decrease in cytotoxicity for mIgG3 containing IgG1 CH3, corroborating the previous gain-of-function results. Importantly, this strategy also identified a small contribution by the murine CH2, as mIgG3 containing human CH2 exhibited a significant decrease in cytotoxicity activity.

According an aspect of the invention there is provided a modified IgG1 antibody or antigen-binding fragment thereof comprising one or more residues of an Fc-region of an immunoglobulin and a binding region, wherein one or more residues of the Fc-region are modified to the corresponding residue from a mouse IgG3 antibody and wherein the modified IgG1 antibody or antigen-binding fragment thereof has enhanced functional affinity when compared to a corresponding IgG1 antibody or antigen binding fragment thereof comprising wildtype Fc-region residues.

In some aspects of the invention there is provided a modified IgG1 antibody or antigen-binding fragment thereof wherein the functional affinity of the modified IgG1 antibody or antigen-binding fragment thereof is enhanced by at least about 10% when compared to a corresponding IgG1 antibody or antigen binding fragment thereof comprising wildtype Fc-region residues.

In some aspects of the invention the functional affinity of the modified IgG1 antibody or antigen-binding fragment thereof is enhanced by at least about 20%, at least about 30%, at least about 40%, at least about 50%, at least about 60%, at least about 70%, at least about 80%, at least about 90% or at least about 100% when compared to a corresponding IgG1 antibody or antigen binding fragment thereof comprising wildtype Fc-region residues.

In some aspects of the invention the modified IgG1 antibody or antigen-binding fragment thereof has enhanced direct cell-killing when compared to a corresponding IgG1 antibody or antigen binding fragment thereof comprising wildtype Fc-region residues.

In some aspects of the invention the direct cell-killing of the modified IgG1 antibody or antigen-binding fragment thereof is enhanced by at least about 10% when compared to a corresponding IgG1 antibody or antigen binding fragment thereof comprising wildtype Fc-region residues.

In some aspects of the invention the direct cell-killing of the modified IgG1 antibody or antigen-binding fragment thereof is enhanced by at least about 20%, at least about 30%, at least about 40%, at least about 50%, at least about 60%, at least about 70%, at least about 80%, at least about 90% or at least about 100% when compared to a corresponding IgG1 antibody or antigen binding fragment thereof comprising wildtype Fc-region residues.

According to a first aspect of the invention, there is provided a modified IgG1 antibody or antigen-binding fragment thereof wherein one or more residues of the CH2 and/or the CH3 domain are replaced with the corresponding residues from the mouse IgG3 CH2 and/or CH3 domain.

According to a second aspect of the invention, there is provided a modified IgG1 antibody or antigen-binding fragment thereof wherein the CH2 and/or the CH3 domain is replaced with a mouse IgG3 CH2 and/or CH3 domain.

Further dissection of the combined CH2-CH3 region through subdomain analysis revealed full regain of mIgG3 direct cytotoxicity to IgG1 by transferring a discontinuous section comprising residues 286-306 and 339-378, containing elements of CH2 and CH3, 26 mIgG3 residues in total. The 26 residues are N286T, K288W, K290Q, E294A, Y300F, V305A, A339P, Q342R, P343A, R344Q, E345T, L351I, S354P, D356E, E357Q, L358M, T359S, N361K, Q362K, K370T, G371N, Y373F, P374S, S375E, D376A, A378S. These residues are required for increased functional affinity through intermolecular cooperativity due to the combined effect of directly interacting as well as conformational residues, the latter potentially creating a permissive framework. A role for charge distribution patterns, notably in CH2, can also not be ruled out, as it has been shown to enhance mIgG3 binding to negatively charged multivalent antigen and is distinct from IgG1 (Klaus and Bereta 2018; Hovenden et al. 2013). Some of the residues involved in our approach lay within a larger consensus binding site for a number of natural binding partners such as protein A, protein G, rheumatoid factor and the neonatal FcRn (DeLano et al. 2000). However, none of our residues are directly involved in FcRn binding (Oganesyan et al. 2014).

According to the third aspect of the invention, there is provided a modified IgG1 antibody or antigen-binding fragment thereof with modifications to one or more of the following residues of the Fc region N286, K288, K290, E294, Y300, V305, A339, Q342, P343, R344, E345, L351, S354, D356, E357, L358, T359, N361, Q362, K370, G371, Y373, P374, S375, D376, A378.

According to the fourth aspect of the invention, there is provided a modified IgG1 antibody or antigen-binding fragment thereof with one or more of the following modifications to the Fc region N286T, K288W, K290Q, E294A, Y300F, V305A, A339P, Q342R, P343A, R344Q, E345T, L351I, S354P, D356E, E357Q, L358M, T359S, N361K, Q362K, K370T, G371N, Y373F, P374S, S375E, D376A, A378S.

In some aspects of the invention, the modified IgG1 antibody or antigen-binding fragment thereof comprises modifications at 1, 2, 3, 4, 5, 6, 7, 8, 9, 10, 11, 12, 13, 14, 15, 16, 17, 18, 19, 20, 21, 22, 23, 24, 25 or 26 residues selected from positions N286, K288, K290, E294, Y300, V305, A339, Q342, P343, R344, E345, L351, S354, D356, E357, L358, T359, N361, Q362, K370, G371, Y373, P374, S375, D376, A378. In a preferred aspect of the invention the modified IgG1 antibody or antigen-binding fragment thereof comprises modifications at all 26 residues.

In some aspects of the invention, the modified IgG1 antibody or antigen-binding fragment thereof comprises 1, 2, 3, 4, 5, 6, 7, 8, 9, 10, 11, 12, 13, 14, 15, 16, 17, 18, 19, 20, 21, 22, 23, 24, 25 or 26 modifications selected from N286T, K288W, K290Q, E294A, Y300F, V305A, A339P, Q342R, P343A, R344Q, E345T, L351 I, S354P, D356E, E357Q, L358M, T359S, N361K, Q362K, K370T, G371N, Y373F, P374S, S375E, D376A and A378S. In a preferred aspect of the invention the modified IgG1 antibody or antigen-binding fragment thereof comprises all 26 modifications.

A plethora of Fc engineering strategies, mostly to impact on mAb effector functions (ADCC and CDC), through modifying FcγR or C1q binding, as well as mAb half-live, via FcRn engagement, have been described in the literature (Wang, Mathieu, and Brezski 2018; Carter 2006). None of these describe the amino acids changes that form part of this patent. Additionally, crystal packing-induced mAb oligomerization through Fc:Fc interactions in a number of human mAb isotypes (Saphire et al. 2001) formed the basis of a recently described hexameric mAb platform for improved complement activation (WO2014/006217 A9; WO2018/083126 A1; WO2018/146317 A1, Ugurlar et al. 2018; de Jong et al. 2016; Diebolder et al. 2014). Efficient hexameric arrangement and C1q binding depended on the individual mutations (E345K or E430G) which are distinct from the amino acid changes which form the basis of this patent. Indeed, the ability to induce programmed cell death (i.e. direct cytotoxicity) by the type II CD20 mAb 11B8, through these mutations that induced a strong CDC ability, was not enhanced, suggesting this position was not responsible for direct cell killing.

Most approved therapeutic mAbs are either humanised or fully human IgG antibodies with murine or chimeric antibodies carrying an increased risk of adverse anti-murine antibody (HAMA) reactions in patients, (Schroff et al. 1985; Azinovic et al. 2006; Miotti et al. 1999; D'Arcy and Mannik 2001). The introduction of only 26 mIgG3 in IgG1 is unlikely to induce HAMA responses. However, they may create MHCII binding epitopes that have the potential to drive HAMA responses in certain patients. Immune Epitope Database (IEDB) analysis of the 26 residue-containing hybrid 88IgG1, revealed a cluster (cluster 1, residues 294-315) containing several potential high-scoring epitopes.

Reverting of three mIgG3 back to IgG1 residues in cluster 1, at positions 294, 300 and 305, maintained the functional affinity and direct cytotoxicity. Importantly, modification of this 23 aa motif (N286, K288, K290, A339, Q342, P343, R344, E345, L351, S354, D356, E357, L358, T359, N361, Q362, K370, G371, Y373, P374, S375, D376, A378), which when modified to the corresponding mouse IgG3 residues are (N286T, K288W, K290Q, A339P, Q342R, P343A, R344Q, E345T, L351 I, S354P, D356E, E357Q, L358M, T359S, N361K, Q362K, K370T, G371N, Y373F, P374S, S375E, D376A, A378S) induced direct cytotoxicity, cellular aggregation, pore formation and eventual cell lysis. The pore formation and eventual cell lysis share similar cellular disintegration features with necroptosis but cannot be distinguished from necrosis or secondary necrosis (Vanden Berghe et al. 2010). The eventual outcome from the released DAMPs—constitutive or induced as a result of activated stress pathways—depends on the cellular environment as well as the underlying signalling cascades, but collectively have the potential to create an inflammatory environment that may further enhance immune effector functions and/or instigate an adaptive immune response through cross-presentation of released tumour antigens (Yatim, Cullen, and Albert 2017; Galluzzi et al. 2017).

According to the fifth aspect of the invention, there is provided a modified IgG1 antibody or antigen-binding fragment thereof with modifications to one or more of the following residues of the Fc region N286, K288, K290, A339, Q342, P343, R344, E345, L351, S354, D356, E357, L358, T359, N361, Q362, K370, G371, Y373, P374, S375, D376, A378.

According to the sixth aspect of the invention, there is provided a modified IgG1 antibody or antigen-binding fragment thereof with one or more of the following modifications to the Fc region N286T, K288W, K290Q, A339P, Q342R, P343A, R344Q, E345T, L351I, S354P, D356E, E357Q, L358M, T359S, N361K, Q362K, K370T, G371N, Y373F, P374S, S375E, D376A, A378S.

In some aspects of the invention, the modified IgG1 antibody or antigen-binding fragment thereof comprises modifications at 1, 2, 3, 4, 5, 6, 7, 8, 9, 10, 11, 12, 13, 14, 15, 16, 17, 18, 19, 20, 21, 22 or 23 residues selected from positions N286, K288, K290, A339, Q342, P343, R344, E345, L351, S354, D356, E357, L358, T359, N361, Q362, K370, G371, Y373, P374, S375, D376, A378. In a preferred aspect of the invention the modified IgG1 antibody or antigen-binding fragment thereof comprises modifications at all 23 residues.

In some aspects of the invention, the modified IgG1 antibody or antigen-binding fragment thereof comprises 1, 2, 3, 4, 5, 6, 7, 8, 9, 10, 11, 12, 13, 14, 15, 16, 17, 18, 19, 20, 21, 22 or 23 modifications selected from N286T, K288W, K290Q, A339P, Q342R, P343A, R344Q, E345T, L351I, S354P, D356E, E357Q, L358M, T359S, N361K, Q362K, K370T, G371N, Y373F, P374S, S375E, D376A, A378S. In a preferred aspect of the invention the modified IgG1 antibody or antigen-binding fragment thereof comprises all 23 modifications.

This set of 23 modifications is exemplified for the 88 antibody in FIGS. 9A and 9B.

Further validation has been demonstrated by the introduction of the selected 23 mIgG3 residues into the sialyl-di-Lewis[a] targeting 129 mAb, that has a more favourable normal tissue distribution whilst targeting a wide range of tumour tissue, notably over 70% of pancreatic, and over 30% of gastric and colorectal tumours, as well as over 20% of ovarian and non-small cell lung cancer tumours. Interestingly, the hybridoma-produced parental 129 mAb is a mIgG1 that lacks direct cytotoxic ability. Thus, the creation of an i129G1 mAb with significantly improved functional affinity, through a slower dissociation rate, compared to 129IgG1, coinciding with nanomolar direct cell killing ability on COLO205 suggests that our approach may have broader applicability, as well as being relevant for immunomodulatory mAbs that rely on avidity effects (Wang, Mathieu, and Brezski 2018). The direct cell killing exerted by i129G1 manifested itself in a similar manner as for i88G1: mAb-induced cellular aggregation followed by pore formation and eventual cell lysis. The introduction of the 23 mIgG3 residues into i129G1 mAb had a mixed effect on effector functions: whilst ADCC was significantly reduced, but maintaining nanomolar $EC_{50}$, the CDC activity of i129G1 was significantly increased. This mirrored the results obtained with i88G1, albeit with a stronger reduction in ADCC for i129G1, suggesting that the nature of the glyco-target also affects ADCC potency: whereas the 88 mAb targets glycoproteins as well as glycolipids, the 129 mAb only targets glycoproteins. Remarkably, i129G1 displayed effective tumour control 1129G1 exhibited significant tumour volume reduction in that was significantly better than 129IgG1, the latter exhibiting no significant tumour reduction. This indicates that the combined effector functions of 129IgG1 were unable to control tumour growth in this model, further emphasizing the value of having direct cytotoxic ability.

In order to evaluate the individual contribution of each of the 23 selected mG3 residues, a single revertant strategy based on i88G1 (example 4) was performed. Each of the 23 mG3 residues in i88G1, singly, were reverted to the hG1 residue and the resulting construct was analysed for direct cell killing this confirmed that the 23 aforementioned residues could be further reduced to 15 residues without significant loss of direct cell killing ability. Notably, six mIgG3 residues in i88G1 could be reverted to IgG1 residues without significant loss of direct cell killing. This was further exemplified using the 129 mAb where the introduction of 15 mIgG3 residues maintained nanomolar direct cell killing on COLO205.

Immunogenicity can be a major obstacle to successful therapy. Anti-drug antibodies may neutralise therapeutic function, influence pharmacokinetics and potentially lead to severe adverse effects. T cell epitopes, which contributes to immunogenicity risk, can be relatively accurately assessed using in silico tools. Immunoinformatic algorithms for identifying T-cell epitopes can be applied to assess and analyse whether an immunotherapy will cause unwanted immunogenicity. In order to assess the potential immunogenicity of our hybrid SD286 306+339 378 construct, created by the presence of 26 mIgG3 residues, we performed an in silico screen of the SD286 306+339 378 sequence for MHCII binding epitopes (Immune Epitope Database, IEDB). Class II restricted T helper cells are more relevant to the humoral immune response and predicted binding clusters have been shown to be strong indicators of T cell responses (Jawa et al. 2013). Two MHCII binding clusters, containing several high scoring binding epitopes, were identified: cluster 1 (residues 294 315) and cluster 2 (residues 365 393) (FIG. 5/FIG. 20). Reversion of three murine residues, 294 (A to E), 300 (F to Y) and 305 (A to V) back to human residues, within the cluster 1, produced a human sequence section to which individuals would have been tolerized. Similarly, reversal of two residues 351 (I to L) and 371 (N to G), within the 339 378 region, removed two MHCII binding cores.

Reversal of one in silico identified immunogenic cluster generates the lead candidate, improved 'i' 88G1, with robust cell killing, pore forming ability and sound immune effector functions.

To demonstrate the effect of introducing the selected residues was not restricted to anti-glycan antibodies, Trastuzumab (sold under the brand name Herceptin® among others) which targets the growth factor receptor, HER2 was subjected to the transfer of the involved residues. The resultant iTrastuzumab had improved stead-state cell binding to moderate HER2-expressing cell lines, coinciding with increased PI uptake. Additionally it had improved affinity, through a slower dissociation rate, compared to wildtype.

According to the seventh aspect of the invention, there is provided a modified IgG1 antibody or antigen-binding fragment thereof with modifications to one or more of the following residues of the Fc region N286, K288, K290, Q342, P343, E345, L351, T359, N361, Q362, G371, P374, S375, D376, A378.

According to the eighth aspect of the invention, there is provided a modified IgG1 antibody or antigen-binding fragment thereof with one or more of the following modifications to the Fc region N286T, K288W, K290Q, Q342R, P343A, E345T, L351I, T359S, N361K, Q362K, G371N, P374S, S375E, D376A, A378S.

This set of 15 modifications is exemplified for antibodies 129 and 88 in FIGS. 9C and 9D.

In some aspects of the invention, the modified IgG1 antibody or antigen-binding fragment thereof comprises modifications at 1, 2, 3, 4, 5, 6, 7, 8, 9, 10, 11, 12, 13, 14 or 15 residues selected from positions N286, K288, K290, Q342, P343, E345, L351, T359, N361, Q362, G371, P374, S375, D376, A378. In a preferred aspect of the invention the modified IgG1 antibody or antigen-binding fragment thereof comprises modifications at all 15 residues.

In some aspects of the invention, the modified IgG1 antibody or antigen-binding fragment thereof comprises 1, 2, 3, 4, 5, 6, 7, 8, 9, 10, 11, 12, 13, 14 or 15 modifications selected from N286T, K288W, K290Q, Q342R, P343A, E345T, L351I, T359S, N361K, Q362K, G371N, P374S, S375E, D376A, A378S. In a preferred aspect of the invention the modified IgG1 antibody or antigen-binding fragment thereof comprises all 15 modifications.

According to the ninth aspect of the invention, there is provided a modified IgG1 antibody or antigen-binding fragment thereof with modifications to one or more of the following residues of the Fc region Q342, P343, E345, N361, Q362, P374, D376.

According to the tenth aspect of the invention, there is provided a modified IgG1 antibody or antigen-binding fragment thereof with one or more of the following modifications to the Fc region Q342R, P343A, E345T, N361K, Q362K, P374S, D376A.

This set of 7 modifications is exemplified for antibody 88 in FIG. 9F.

In some aspects of the invention, the modified IgG1 antibody or antigen-binding fragment thereof comprises modifications at 1, 2, 3, 4, 5, 6 or 7 residues selected from positions Q342, P343, E345, N361, Q362, P374, D376. In a preferred aspect of the invention the modified IgG1 antibody or antigen-binding fragment thereof comprises modifications at all 7 residues.

In some aspects of the invention, the modified IgG1 antibody or antigen-binding fragment thereof comprises 1, 2, 3, 4, 5, 6 or 7 modifications selected from Q342R, P343A, E345T, N361K, Q362K, P374S, D376A. In a preferred aspect of the invention the modified IgG1 antibody or antigen-binding fragment thereof comprises all 7 modifications.

In one aspect of the invention, the modified IgG1 antibody or antigen-binding fragment thereof comprises one or more of the sequences disclosed in FIG. 15. In one aspect of the invention, there is provided a modified IgG1 antibody or antigen-binding fragment thereof comprising a heavy chain and a light chain sequence as disclosed in FIG. 15.

In one aspect of the invention, the modified IgG1 antibody or antigen-binding fragment thereof comprises one or more of the sequences disclosed in FIG. 16. In one aspect of the invention, there is provided a modified IgG1 antibody or antigen-binding fragment thereof comprising a heavy chain and a light chain sequence as disclosed in FIG. 16.

In one aspect of the invention, the modified IgG1 antibody or antigen-binding fragment thereof comprises one or more of the sequences disclosed in FIG. 17. In one aspect of the invention, there is provided a modified IgG1 antibody or antigen-binding fragment thereof comprising a heavy chain and a light chain sequence as disclosed in FIG. 17.

In one aspect of the invention, the modified IgG1 antibody or antigen binding fragment thereof comprises one or more of the sequences disclosed in FIG. 19. In one aspect of the invention, there is provided a modified IgG1 antibody or antigen binding fragment thereof comprising a heavy chain and a light chain sequence as disclosed in FIG. 19.

In some aspects of the invention, the "corresponding IgG1 antibody or antigen-binding fragment thereof" refers to the unmodified (i.e. wildtype) antibody or antigen-binding fragment thereof which comprises the native residues without any changes to the corresponding mouse IgG3 residues. In some aspects of the invention, the corresponding IgG1 antibody or antigen-binding fragment thereof binds to the same target or targets (e.g. the same epitope) as the modified IgG1 antibody or antigen-binding fragment thereof. In some aspects of the invention the modified and corresponding unmodified IgG1 antibody or antigen-binding fragment thereof comprise at least 1, at least 2, at least 3, at least 4, at least 5 or at least 6 of the same CDR sequences (i.e. VHCDR1, VHCDR2, VHCDR3, VLCDR1, VLCDR2, VLCDR3). In some aspects of the invention the modified and corresponding unmodified IgG1 antibody or antigen-binding fragment thereof comprise the same binding region sequences. In some aspects of the invention the modified and corresponding unmodified IgG1 antibody or antigen-binding fragment thereof comprise the same variable region sequences (e.g. the same variable heavy chain sequence and/or the same variable light chain sequence).

In some aspects of the invention the "binding region" refers to the portion of the antibody or antigen-binding fragment thereof which is responsible for binding to the target antigen. For example it may comprise one constant and one variable domain of each of the heavy and the light chain. In some aspects of the invention, the binding region can refer to complementarity determining regions (CDR) sequences (i.e. VHCDR1, VHCDR2, VHCDR3, VLCDR1, VLCDR2, VLCDR3).

The structure of the IgG1 antibody or antigen-binding fragment thereof will generally be of an antibody heavy or light chain sequence or substantial portion thereof. The structures and locations of immunoglobulin domains may be determined by reference to http://www.imqt.org/.

Throughout the specification the residue numbering refers to the standardised IMGT system for the numbering of antibody sequences, as disclosed in Lefranc M P, Giudicelli V, Ginestoux C, Jabado-Michaloud J, Folch G, Bellahcene F, et al. IMGT, the international ImMunoGeneTics information system. Nucleic acids research. 2009; 37:D1006-12. Other suitable numbering systems are known to the skilled person. Other suitable numbering systems may be used to identify corresponding residues between the modified IgG1 antibodies and antigen-binding fragments thereof or antigen-binding fragments thereof. Any numbering system which allows identification of corresponding residues is suitable for use with the present invention. The numbering system used herein is not limiting on the scope of the invention, but is used simply to identify the relevant residues which may be modified. The term "corresponding residue" is intended to mean the residue in the equivalent position, structurally or functionally, in the two or more antibodies or antigen-binding fragments thereof that are being compared. In some cases, corresponding residues may be identified by sequence alignment. In some cases, corresponding residues may be identified by structural comparison.

In some aspects of the invention the IgG1 antibody or antigen-binding fragment thereof comprising one or more residues of an Fc-region of an immunoglobulin comprises at least 10 amino acid residues of an Fc-region, at least 20 amino acid residues of an Fc-region, at least 30 amino acid residues of an Fc-region, at least 40 amino acid residues of an Fc-region, at least 50 amino acid residues of an Fc-region, at least 75 amino acid residues of an Fc-region, at least 100 amino acid residues of an Fc-region, at least 200 amino acid residues of an Fc-region, at least 300 amino acid residues of an Fc-region, at least 400 amino acid residues of an Fc-region or at least 500 amino acid residues of an Fc-region. Preferably the IgG1 antibody or antigen-binding fragment thereof comprises the entire Fc-region of an immunoglobulin.

In some aspects of the invention, the one or more residues of the Fc region are selected from the CH2 and/or the CH3 domains. In some aspects the one or more residues are selected from the CH2 domain. In some aspects the one or more residues are selected from the CH3 domain.

In some aspects of the invention the functional affinity of a modified IgG1 antibody or antigen-binding fragment thereof and the corresponding wildtype IgG1 antibody or antigen-binding fragment thereof may be determined by Surface Plasmon Resonance (e.g. Biacore® 3000/T200, GE Healthcare), for example by injecting increasing concentrations (0.3 nmol/L-200 nmol/L) of an IgG1 antibody or antigen-binding fragment thereof across a CM5 chip comprising an appropriate ligand and fitting the data to an appropriate binding model using appropriate software (e.g. BIAevaluation 4.1).

Corresponding experiments using the same conditions can be conducted for the modified IgG1 antibody or antigen-binding fragment thereof. In some aspects of the invention, the modified IgG1 antibody or antigen-binding fragment thereof shows greater functional affinity to the corresponding wildtype IgG1 antibody or antigen-binding fragment thereof when the Surface Plasmon Resonance data indicates that the modified IgG1 antibody or antigen-binding fragment thereof binds more tightly to the ligand-coated CM5 chip. Ligands comprise glycan-HSA and control conjugates for anti-glycan antibodies.

The Biacore® CM5 chip, coated with an anti-his antibody, comprises carboxymethylated dextran covalently attached to a gold surface. Molecules are covalently coupled to the sensor surface via amine, thiol, aldehyde or carboxyl groups. Interactions involving small organic molecules, such as drug candidates, through to large molecular assemblies or whole viruses can be studied. A high binding capacity gives a high response, advantageous for capture assays and for interactions involving small molecules. High surface stability provides accuracy and precision and allows repeated analysis on the same surface. Other suitable chips are known to the skilled person and the Surface Plasmon Resonance protocols can be adapted by standard techniques known in the art.

In some aspects of the invention the direct cell killing of a modified IgG1 antibody or antigen-binding fragment thereof and the corresponding wildtype IgG1 antibody or antigen-binding fragment thereof may be determined by propidium iodide (PI) uptake, for example by incubating the IgG1 antibody or antigen-binding fragment thereof with COLO205 or HCT-15 cells ($5 \times 10^4$) for 2 hours at 37° C. followed by adding 1 μg of P1 for 30 minutes, resuspending the cells in PBS and processing the cells on a flow cytometer (e.g. Beckman Coulter® FC-500 or MACSQuant® 10) and analysing the results with appropriate software (e.g. WinMDI 2.9 or FlowJo v10). Corresponding experiments using the same conditions can be conducted for the modified IgG1 antibody or antigen-binding fragment thereof. In some aspects of the invention, the modified IgG1 antibody or antigen-binding fragment thereof provides greater direct cell killing than the corresponding wildtype IgG1 antibody or antigen-binding fragment thereof when the PI uptake is greater when the cells are incubated with the modified IgG1 antibody or antigen-binding fragment thereof.

The improved functional properties of the modified IgG1 antibody or antigen-binding fragment thereof are measured relative to the corresponding functional properties of the wild type IgG1 antibody or antigen-binding fragment thereof that does not comprise the modified residues in the Fc-region. Since the improved functional properties are a relative measure, the precise method used to determine the functional affinity and/or direct cell killing, or any other functional property of the claimed IgG1 antibodies or antigen-binding fragments thereof, does not affect the relative change in that functional property. Many suitable methods of measuring the functional properties of antibodies and antigen-binding fragments thereof are known to the skilled person. Any suitable method of measuring these functional properties may be used to measure the functional properties of the claimed modified IgG1 antibodies and antigen-binding fragments thereof or antigen-binding fragments thereof, provided the same method is applied to the corresponding wildtype IgG1 antibody or antigen-binding fragment thereof for the purposes of a fair comparison.

The creation of improved cancer glycan targeting mAbs, with enhanced functional affinity as well as direct cytotoxicity, through establishing intermolecular cooperativity binding, may lead to superior clinical utility. This approach may also have value for other mAbs targeting repeating or high-density antigen. Additionally, reinstating the unusual, proinflammatory cell killing mode observed for many gly-can-targeting mIgG3 mAbs, into the IgG1 framework, has the potential to be used in combination with other immu-notherapies.

The modified IgG1 antibody of the present invention can be used in methods of diagnosis and treatment of tumours in human or animal subjects. When used in diagnosis, the modified IgG1 antibodies and antigen-binding fragments thereof of the invention may be labelled with a detectable label, for example a radiolabel such as I or Tc, which may be attached to the modified IgG1 antibody of the invention using conventional chemistry known in the art of antibody imaging. Labels also include enzyme labels such as horse-radish peroxidase. Labels further include chemical moieties such as biotin which may be detected via binding to a specific cognate detectable moiety, e.g., labelled avidin. Although the modified IgG1 antibodies and antigen-binding fragments thereof of the invention have in themselves been shown to be effective in killing cancer cells, they may additionally be labelled with a functional label. Functional labels include substances which are designed to be targeted to the site of cancer to cause destruction thereof. Such functional labels include toxins such as ricin and enzymes such as bacterial carboxypeptidase or nitroreductase, which are capable of converting prodrugs into active drugs. In addition, the modified IgG1 antibodies and antigen-binding fragments thereof may be attached or otherwise associated with chemotherapeutic or cytotoxic agents, such as may-tansines (DMI and DM4), onides, auristatins, calicheamicin, duocamycin, doxorubicin 90 131 or radiolabels, such as Y or I. Furthermore, the modified IgG1 antibodies and antigen-binding fragments thereof of the present invention may be administered alone or in combination with other treatments, either simultaneously or sequentially, dependent upon the condition to be treated. Thus, the present invention further provides products containing the modified IgG1 antibodies and antigen-binding fragments thereof of the present invention and an active agent as a combined preparation for simultaneous, separate or sequential use in the treatment of a tumour.

Active agents may include chemotherapeutic or cytotoxic agents including, 5-Fluorouracil, cisplatin, Mitomycin C, oxaliplatin and tamoxifen, which may operate synergisti-cally with the modified IgG1 antibodies and antigen-binding fragments thereof of the present invention. Other active agents may include suitable doses of pain relief drugs such as non-steroidal anti-inflammatory drugs (e.g., aspirin, par-acetamol, ibuprofen or ketoprofen) or opiates such as mor-phine, or anti-emetics.

Whilst not wishing to be bound by theory, the ability of the modified IgG1 antibodies and antigen-binding fragments thereof of the invention to synergise with an active agent to enhance tumour killing may not be due to immune effector mechanisms but rather may be a direct consequence of the modified IgG1 antibodies and antigen-binding fragments thereof binding to cell surface receptor. The modified IgG1 antibodies and antigen-binding fragments thereof of the present invention will usually be administered in the form of a pharmaceutical composition, which may comprise at least one component in addition to the modified IgG1 antibodies and antigen-binding fragments thereof.

The pharmaceutical composition may comprise, in addi-tion to active ingredient, pharmaceutically acceptable excipient, diluent, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g., intravenous. Preferably the route of administration is intravenous.

It is envisaged that injections will be the primary route for therapeutic administration of the compositions although delivery through a catheter or other surgical tubing is also used. Some suitable routes of administration include intra-venous, subcutaneous, intraperitoneal and intramuscular administration. Liquid formulations may be utilised after reconstitution from powder formulations.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, anti-oxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solu-tion, dextrose or other saccharide solution or glycols such as ethylene glycol, propylene glycol or polyethylene glycol may be included. Where the formulation is a liquid it may be for example, a physiologic salt solution containing non-phosphate buffer at pH 6.8-7.6, or a lyophilised powder.

The composition may also be administered via micro-spheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Implantable or microcapsular sustained release matrices include polylactides (U.S. Pat. No. 3,773,919; EP-A-0058481) copolymers of L-glutamic acid and gamma ethyl-L-glutamate [43], poly (2-hydroxyethyl-methacrylate). Liposomes containing the polypeptides are prepared by well-known methods: (Eppstein et al. 1985; Hwang, Luk, and Beaumier 1980); EP-A-0052522; EP-A-0036676; EP-A-0088046; EP-A-0143949; EP-A-0142541; JP-A-83-11808; U.S. Pat. Nos. 4,485,045 and 4,544,545. Ordinarily, the liposomes are of the small (about 200-800 Angstroms) unilamellar type in which the lipid content is greater than about 30 mol. % cholesterol, the selected proportion being adjusted for the optimal rate of the polypeptide leakage. The composition may be administered in a localised manner to a tumour site or other desired site or may be delivered in a manner in which it targets tumour or other cells.

The compositions are preferably administered to an indi-vidual in a "therapeutically effective amount", this being sufficient to show benefit to the individual. The actual amount administered, and rate and time-course of adminis-tration, will depend on the nature and severity of what is being treated. Prescription of treatment, e.g., decisions on dosage etc, is within the responsibility of general practitio-ners and other medical doctors, and typically takes account of the disorder to be treated, the condition of the individual patient, the site of delivery, the method of administration and other factors known to practitioners. The compositions of the invention are particularly relevant to the treatment of existing tumours, especially cancer, and in the prevention of the recurrence of such conditions after initial treatment or surgery. Examples of the techniques and protocols mentioned above can be found in Remington's Pharmaceutical Sciences 16 edition Oslo,A (ed) 1980.

The optimal dose can be determined by physicians based on a number of parameters including, for example, age, sex, weight, severity of the condition being treated, the active ingredient being administered and the route of administration. In general, a serum concentration of polypeptides and antibodies that permits saturation of receptors is desirable. A concentration in excess of approximately InM is normally sufficient. For example, a dose of 100 mg/m² of antibody provides a serum concentration of approximately 20 nM for approximately eight days. As a rough guideline, doses of antibodies may be given weekly in amounts of 10-300 mg/m². Equivalent doses of antibody fragments should be used at more frequent intervals in order to maintain a serum level in excess of the concentration that permits saturation of the glycan.

The dose of the composition will be dependent upon the properties of the modified IgG1 antibodies and antigen-binding fragments thereof, e.g., its binding activity and in vivo plasma half-life, the concentration of the polypeptide in the formulation, the administration route, the site and rate of dosage, the clinical tolerance of the patient involved, the pathological condition afflicting the patient and the like, as is well within the skill of the physician. For example, doses of 3000 g of antibody per patient per administration are preferred, although dosages may range from about 10 μg to 6 mg per dose. Different dosages are utilised during a series of sequential inoculations; the practitioner may administer an initial inoculation and then boost with relatively smaller doses of antibody.

The modified IgG1 antibodies and antigen-binding fragments thereof of the present invention may be generated wholly or partly by chemical synthesis. The modified IgG1 antibodies and antigen-binding fragments thereof can be readily prepared according to well-established, standard liquid or, preferably, solid-phase peptide synthesis methods, general descriptions of which are broadly available (see, for example, in J. M. Stewart and J. D. Young, (1984) [46], in M. Bodanzsky and A. Bodanzsky, (1984); or they may be prepared in solution, by the liquid phase method or by any combination of solid-phase, liquid phase and solution chemistry, e.g., by first completing the respective peptide portion and then, if desired and appropriate, after removal of any protecting groups being present, by introduction of the residue X by reaction of the respective carbonic or sulfonic acid or a reactive derivative thereof.

Another convenient way of producing the modified IgG1 antibodies and antigen-binding fragments thereof according to the present invention is to express the nucleic acid encoding them, by use of nucleic acid in an expression system. The present invention further provides an isolated nucleic acid encoding the modified IgG1 antibodies and antigen-binding fragments thereof of the present invention. Nucleic acid includes DNA and RNA. The skilled person will be able to determine substitutions, deletions and/or additions to such nucleic acids which will still provide the modified IgG1 antibodies and antigen-binding fragments thereof of the present invention.

The present invention also provides constructs in the form of plasmids, vectors, transcription or expression cassettes which comprise at least one nucleic acid as described above. The present invention also provides a recombinant host cell which comprises one or more constructs as above. As mentioned, a nucleic acid encoding the modified IgG1 antibodies and antigen-binding fragments thereof of the invention forms an aspect of the present invention, as does a method of production of the modified IgG1 antibodies and antigen-binding fragments thereof which method comprises expression from encoding nucleic acid therefor. Expression may conveniently be achieved by culturing under appropriate conditions recombinant host cells containing the nucleic acid. Following production by expression the modified IgG1 antibodies and antigen-binding fragments thereof may be isolated and/or purified using any suitable technique, then used as appropriate. Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The expression of antibodies and antibody fragments in prokaryotic cells such as E. coli is well established in the art. For a review see for example (Pluckthun 1991). Expression in eukaryotic cells in culture is also available to those skilled in the art as an option for production of the modified IgG1 antibodies and antigen-binding fragments thereof, see for recent review, for example (Reff 1993; Trill, Shatzman, and Ganguly 1995).

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g., 'phage, or phagemid, as appropriate. For further details see, for example, (Sambrook, Fritsch, and Maniatis 1989). Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al; 1992 (Ausubel et al. 1992).

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g., by culturing host cells under conditions for expression of the gene. In one embodiment, the nucleic acid of the invention is integrated into the genome (e.g., chromosome) of the host cell. Integration may be promoted by inclusion of sequences which promote recombination with the genome, in accordance with standard techniques. The present invention also provides a method which comprises using a construct as stated above in an expression system in order to express the modified IgG1 antibodies and antigen-binding fragments thereof as above.

The fragment crystallizable region (Fc region) is the tail region of an antibody that interacts with cell surface receptors called Fc receptors and some proteins of the complement system. This property allows antibodies to activate the immune system. In IgG antibody isotypes, the Fc region is composed of two identical protein fragments, derived from the second and third constant domains of the antibody's two heavy chains. The Fc regions of IgGs comprise a highly conserved N-glycosylation site.

The Fc (Fragment, crystallizable) of an IgG consists of a paired set of antibody HC domains, each of which has a CH2 fused to a CH3, which form a structure of about 50 kDa. The name "Fragment, crystallizable" (Fc) comes from the fact that after cleavage of serum-derived myeloma IgG fractions with papain, the only fragment that could be crystallized was the paired CH2-CH3 fragment.

Within the Fc, the two CH3 domains bind each other tightly, whereas the two CH2 domains have no direct protein-protein contact with one another. An oligosaccharide is bound to asparagine-297 (N297) within each of the two CH2 domains, filling part of the space between the two CH2s. In some crystal structures, hydrogen bonding has been observed between the two carbohydrate chains, directly and through bridging water molecules. While the antibody appears to be a highly segmented molecule, it has been demonstrated that the structure of the Fc can impact the binding of the FAbs to the targeted antigens and, similarly, that the content of the variable chain in the FAbs can impact binding of the Fc to various receptors. Recently circular dichroism studies have confirmed significant structural coupling between the FAb arms and the Fc of the IgG. Thus the IgG molecule is a highly complex molecule in which the different domains significantly interact, even at long distances.

While bi-/multivalent antibodies comprise binding domains that interact with epitopes, synthetic bi-/multivalent ligands comprise pharmacophores that interact with target sites. The term 'functional affinity' can also be used to designate a bi-/multivalency-related increase in apparent affinity. This term is synonymous with 'avidity'.

Avidity refers to the accumulated strength of multiple affinities of individual non-covalent binding interactions, such as between a protein receptor and its ligand, and can also be referred to as 'functional affinity'. As such, avidity is distinct from intrinsic affinity, which describes the strength of a single interaction. However, because individual binding events increase the likelihood of other interactions to occur (i.e. increase the local concentration of each binding partner in proximity to the binding site), avidity should not be thought of as the mere sum of constituent affinities but as the combined effect of all affinities participating in the biomolecular interaction. The utility of the distinction between "intrinsic affinity" and "functional affinity" arises from the different emphasis involved in each term. The former is most useful when the structural relationship between the antibody combining site and the complementary region of the ligand is under scrutiny or when kinetic mechanisms of the specific interaction are under investigation. On the other hand, the latter is particularly significant when the quantitative measurement of the enhancement of affinity is being examined, as in the present invention.

Both 'functional affinity' and 'intrinsic affinity' refer to formally identical reversible processes as follows:

$$F_1 + L_1 \rightleftharpoons 1{:}1 \text{ complex(monovalent)}$$

$$Ab_n + L_m \rightleftharpoons 1{:}1 \text{ complex(multivalent)}$$

where $F_1$ is a monovalent antibody fragment, $L_1$ a monovalent ligand, $Ab_n$ is a multivalent antibody, and $L_m$ is a multivalent ligand with m groups. In each instance, two kinetic units combine reversibly to form one unit and each process can, in principle, be characterized by an association constant. Since the association constant is a measure of the thermodynamic affinity both processes can therefore be assigned quantitative values of the affinity.

Fragments of Antibodies and Antigen-Binding Molecules

The antigen-binding molecule of the invention can be a fragment of an antibody, specifically an antigen-binding fragment of an antibody. The antigen-binding fragments comprise one or more antigen-binding regions. It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341:544-546 (1989)) which consists of a VH domain; (v) isolated CDR regions; (vi) F(ab')2 fragments, a bivalent fragment comprising two linked Fab fragments; (vii) single chain Fv molecules (scFv), wherein a VH domain and a VL domain are linked by a peptide linker which allows the two domains to associate to form an antigen-binding site (Bird et al., Science 242:423-426 (1988); Huston et al., PNAS USA 85:5879-5883 (1988)); (viii) bispecific single chain Fv dimers (PCT/US92/09965) and (ix) "diabodies", multivalent or multispecific fragments constructed by gene fusion (WO94/13804; P. Hollinger et al., Proc. Natl. Acad. Sci. USA 90: 6444-6448 (1993)). Typically, the fragment is a Fab, F(ab')2 or Fv fragment or an scFv molecule.

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associated with each other to form an antigen-binding site: antigen-binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Hollinger & Winter, Current Opinion Biotechnol. 4:446-449 (1993)), e.g. prepared chemically or from hybrid hybridomas, or may be any of the bispecific antibody fragments mentioned below. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al., EMBO Journal 10:3655-3659 (1991).

A bispecific antibody is one which can bind to two target molecules simultaneously, such as two antigens or two epitopes. Bispecific antibodies may also be referred to as dual binding antibodies. Examples of bispecific antibody formats include, but are not limited to; (mAb)2, Fcab, F(mAb')2, quadromas, scFv (single chain variable fragments), bsDb (bispecific diabodies), scBsDb (single chain bispecific diabodies), BiTE (bispecific T cell engagers), DART (dual affinity re-targeting antibodies), charge pairs, tandem antibodies, tandem scFv-Fc, Fab-scFv-Fc, Fab-scFv, minibodies, zybodies, DNL-F(ab)3 (dock-and-lock trivalent Fabs), bssdAb (bispecific single domain antibodies) and knobs-in-holes.

Bispecific diabodies, as opposed to bispecific whole antibodies, may also be useful because they can be readily constructed and expressed in E. coli. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

In some aspects of the invention, it may be desirable to generate multispecific (e.g. bispecific) anti-target antibody having binding specificities for at least two different epitopes of the same or different molecules. Exemplary bispecific antibodies may bind to two different epitopes of the target molecule. Alternatively, a target-specific antibody arm may be combined with an arm which binds to a cell surface molecule, such as a T-cell receptor molecule (e.g., CD3). Exemplary bispecific antibodies of the invention can bind an antigen from a T-cell receptor molecule (e.g. CD3) and any other target.

The modified IgG1 antibodies and antigen-binding fragments thereof of the present invention may be an antibody or an antibody fragment, Fab, (Fab')2, scFv, Fv, dAb, Fd or a diabody. The antibody may be a polyclonal antibody. The antibody may be a monoclonal antibody (mAb). Modified IgG1 antibodies and antigen-binding fragments thereof of the present invention of the invention may be humanised, chimeric or veneered antibodies, or may be non-human antibodies of any species. In a preferred embodiment the modified IgG1 antibodies and antigen-binding fragments thereof of the present invention are human or humanized.

Murine or chimeric antibodies carry an increased risk of adverse anti-murine antibody (HAMA) reactions in patients (Schroff et al. 1985; Azinovic et al. 2006; Miotti et al. 1999; D'Arcy and Mannik 2001). Accordingly, most approved therapeutic mAbs are either humanised or fully human IgG antibodies.

Variants

The present invention also extends to variants of any peptide sequences disclosed herein. As used herein the term "variant" relates to proteins that have a similar amino acid sequence and/or that retain the same function. For instance, the term "variant" encompasses proteins or polypeptides which include one or more amino acid additions, deletions, substitutions or the like. An example of a variant of the present invention is a protein comprising a peptide as defined below, apart from the substitution of one or more amino acids with one or more other amino acids. Amino acid substitutions may be made to, for example, reduce or eliminate liabilities in the amino acid sequences. Alternatively, amino acid substitutions may be made to improve antigen affinity or to humanise or deimmunise the antibodies, if required. Affinity matured variants, humanised variants and deimmunised variants of the specified antibodies are provided herein, as well as variants comprising amino acid substitutions to reduce or eliminate any liabilities in the sequences of the antibodies.

As noted above, in some embodiments, any substitutions may occur only in the framework regions. In such embodiments, the original CDR sequences are retained, but variation may occur in one or more framework regions.

Variant antigen-binding molecules having the one or more amino acid substitutions may retain the functional activity (for example EC50, IC50, IC90, Kd, functional affinity and/or direct cell killing) of the antigen-binding molecule from which the variant antigen-binding molecule is derived. Variant antigen-binding molecules of the invention can be used and formulated in the same ways as described for the antigen-binding molecules from which they are derived.

Substitutions

The skilled person is aware that various amino acids have similar properties. One or more such amino acids of a substance can often be substituted by one or more other such amino acids without eliminating a desired activity of that substance.

Thus, the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions.

Using the three letter and one letter codes the naturally occurring amino acids may be referred to as follows: glycine (G or Gly), alanine (A or Ala), valine (V or Val), leucine (L or Leu), isoleucine (I or lie), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and glutamic acid include glutamate, unless the context specifies otherwise.

Amino acid deletions or insertions can also be made relative to the amino acid sequence for the fusion protein referred to below. Thus, for example, amino acids which do not have a substantial effect on the activity of the polypeptide, or at least which do not eliminate such activity, can be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

In some embodiments, the following amino acids can be exchange for each other for conservative amino acid substitutions:

| Class | Exchangeable amino acids |
| --- | --- |
| Aliphatic | Glycine, Alanine, Valine, Leucine, Isoleucine |
| Hydroxyl or Sulfur/Selenium-containing | Serine, Cysteine, Threonine, Methionine |
| Aromatic | Phenylalanine, Tyrosine, Tryptophan |
| Basic | Histidine, Lysine, Arginine |
| Acidic and their Amide | Aspartate, Glutamate, Asparagine, Glutamine |

Therefore, references to "conservative" amino acid substitutions refer to amino acid substitutions in which one or more of the amino acids in the sequence of the antibody (e.g.

in the CDRs or in the VH or VL sequences) is substituted with another amino acid in the same class as indicated above. Conservative amino acid substitutions may be preferred in the CDR regions to minimise adverse effects on the function of the antibody. However, conservative amino acid substitutions may also occur in the framework regions.

Amino acid changes relative to the sequence given below can be made using any suitable technique e.g. by using site-directed mutagenesis or solid-state synthesis.

It should be appreciated that amino acid substitutions or insertions within the scope of the present invention can be made using naturally occurring or non-naturally occurring amino acids, although naturally occurring amino acids may be preferred. Whether or not natural or synthetic amino acids are used, it may be preferred that only L-amino acids are present.

Manufacturing Liabilities

Therapeutic proteins such as antibodies are heterogenous and complex by nature due to chemical modifications and post-translational modifications (PTMs). Modifications can be caused by a number of factors such as the host cell system, processes used in manufacture or conditions during storage or manufacture. Modifications can relate to the chemical stability of the molecule itself or the aggregation potential and the effect this has on intrinsic physical stability of the antibody. Amino acid motifs or residues in a given antibody sequence that may undergo spontaneous modification during manufacture or storage are referred to as liabilities. Accordingly, mutations may be made to the antibody sequence to address the liabilities to reduce the susceptibility of the antibody to modification and degradation.

Such modifications as a result of liabilities in the antibody sequences may include glycosylation, deamidation, oxidation and variations of C- and N-termini. Such modifications may arise during manufacture. Certain residues and structural or sequence motifs are more liable to certain modifications. Examples of such liabilities to modification include Asn N-linked glycosylation, Ser/Thr O-linked glycosylation, Asn deamidation, Asp isomerisation/fragmentation, Lys glycation, Met/Trp oxidation, free thiol groups, pyroglutamates, C-terminal Lys.

A skilled person is aware that computational tools can be used to predict and identify structural and sequence liabilities which could potentially result in modifications. To minimise the occurrence of modifications alterations to the manufacturing process can be made. Protein engineering may also be considered to reduce the risk. For example, selective mutation of these liabilities can help to identify and reduce the risk of a modification endangering the stability of an antibody.

Aspartic acid residues (Asp) may undergo spontaneous modification. Asp containing motifs, such as Asp-Gly sequences may undergo spontaneous isomerization to form isoaspartic acid. Formation of isoaspartate may debilitate or completely abrogate the binding of the antibody. This is of additional importance if the Asp residue appears in the CDR of an antibody.

Aspartic acid residues (Asp) can therefore be substituted with any naturally occurring amino acid to reduce this liability to modification. Optionally, aspartic acid residues (Asp) can be substituted with alanine (Ala), glutamine (Gln) or glutamic acid (Glu) to reduce this liability to modification. Optimization of production/formulation can also be investigated to reduce isomerization. Alternatively, Asp-Gly motifs may be modified by substituting the glycine residue with another naturally occurring amino acid to inhibit deamidation, rather than by substitution of the Asp residue.

Methionine residues (Met) may undergo spontaneous modification. The presence of methionine (Met) in a CDR, especially if exposed to solvent, can create a problem if the methionine is oxidized and this interferes with binding. Methionine residues can therefore be substituted with any other naturally occurring amino acid to reduce this liability to modification. Methionine residues may preferably be substituted with Ala or Leu. Optimization of production/formulation can also be investigated to reduce oxidation.

Preferred features of each aspect of the invention are as for each of the other aspects mutatis mutandis. The prior art documents mentioned herein are incorporated to the fullest extent permitted by law.

BRIEF DESCRIPTION OF THE DRAWINGS

The following detailed description, given by way of example, but not intended to limit the invention solely to the specific embodiments described, may best be understood in conjunction with the accompanying drawings.

Figure 5:
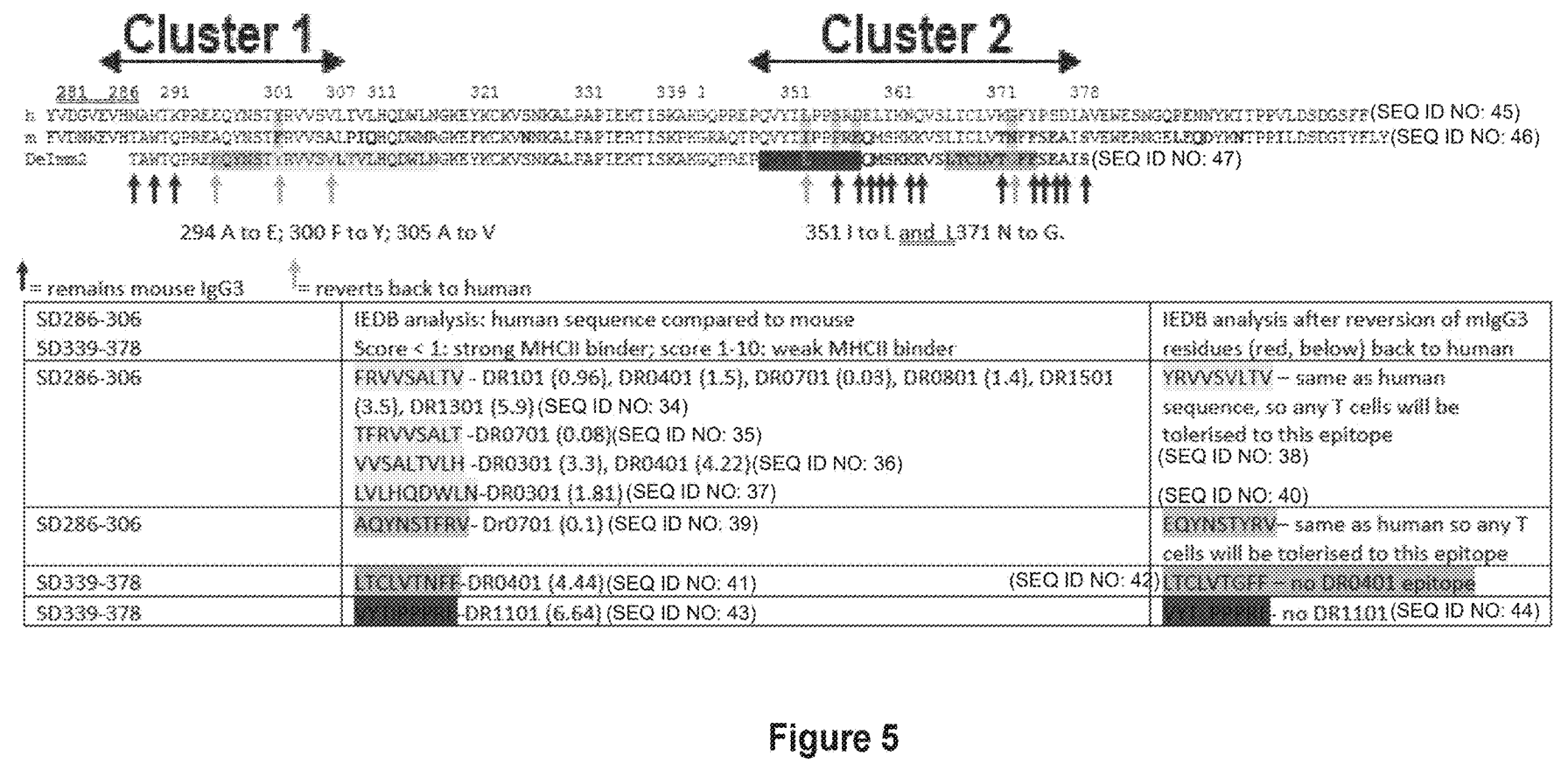

FIG. 5. MHCII binding clusters containing several high-scoring binding epitopes. Cluster 1 consists of residues 294-315 and cluster 2, residues 365-393.

FIG. 15. DNA and protein antibody 88 antibody sequences including "improved" versions 1-3.

FIG. 16. DNA and protein antibody 129 antibody sequences including "improved" versions 1-3.

FIG. 17. DNA and protein antibody 27 antibody sequences including "improved" version 1.

FIG. 19. Protein antibody Trastuzumab antibody sequences including "improved" versions 1 & 2.

FIG. 20. IEDB screen for MHC class II binding epitopes. Top, sequence alignment (ClustalW) of hIgG1 and mIgG3 sequences encompassing SD286-306+339-378. The combined subdomains, 286-306 and 339-378 are boxed; clusters 1 and 2, identified by IEDB analysis are represented by arrows. Below, IEDB analysis table with MHCII binding epitopes, DR alleles and scores in the middle column. The right hand column lists residues changes (mIgG3→hIgG1, underlined) that would resolve immunogenicity. DI, de-immunized construct.

DETAILED DESCRIPTION OF THE INVENTION

Figure 1A:
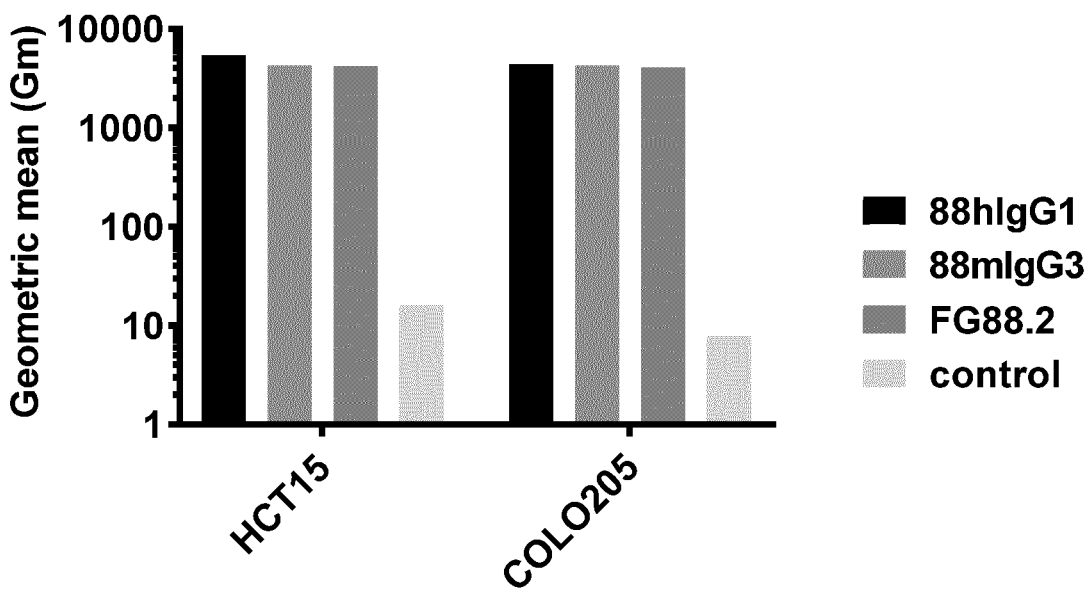
FIG. 1. Maintenance of cancer cell binding, but significantly decreased direct cytotoxicity of 881gG1 compared to 88mIgG3 and parental hybridoma mAb. A. Comparable HCT15 and COLO205 cell binding analysis by 881gG1, 88mIgG3 and FG88 (hybridoma mAb); B. significantly reduced direct cytotoxicity (PI uptake) on HCT15 by 88IgG1 compared to parental 88mIgG3 and FG88; significantly reduced proliferation inhibition by 881gG1 compared to parental 88mIgG3 and FG88 on COLO205 (C) and HCT15 (D). Significance was deduced from two-way ANOVA with Dunnett's corrections for multiple comparisons.

In describing the embodiments of the invention, the terminology is not intended to be limited to the specific terms so selected, and it is understood that each specific term includes all technical equivalents which operate in a similar manner to accomplish a similar purpose.

The term 'immunoglobulin' or Ig, refers to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterised. See for instance Fundamental Immunology Ch. 7 (Paul, W., ed., $2^{nd}$ ed. Raven Press, N.Y. (1989)).

Methods

Materials, Cells and Antibodies

All cancer cell lines: COLO205, HCT15 (C170, C170HM2), AGS, COLO201, ST16, MCF7, OVCAR3, H322, OVCA4, LoVo, MKN45, 791T, BT474, MDA-MB231, SKBR3, SKOV3, and 791T, as well as the murine myeloma NSO cell line were purchased from ATCC (Virginia, USA). All cell lines were authenticated using short tandem repeat profiling. Human serum albumin (HSA)-APD-sialyl-Lewis$^a$ and HSA-APD-Lewis$^a$ were from IsoSepAB (Sweden). Erb2-His was sourced from Abcam as well as Stratech. Cell lines were maintained in RPMI medium 1640 (Sigma), or DMEM high glucose supplemented with 10% fetal calf serum, L-glutamine (2 mM) and sodium bicarbonate-buffered. Parental murine FG88 and FG129 mAbs were generated as previously described (Chua et al. 2015).

Cloning of Modified mAb Constructs

In order to create chimeric IgG1 variants of our hybridoma-produced mAbs (FG88.2 and FG129), the heavy chain and light chain variable regions encoding the respective mAbs were introduced into the pDCOrig vector using the restriction enzymes BamHI/BsiWI (light chain locus) or HindIII/AfeI (heavy chain locus) (Metheringham et al. 2009). The synthetic heavy chain constant regions, including full mIgG3 constant regions as well as interchanged mIgG3-IgG1 domains and single residue changes, were designed and ordered from Eurofins MWG (Ebersberg, Germany). Typically, this involved a 1054 bp cassette, stretching from the AfeI restriction site at the JH/CH junction to an XbaI site 3' to the CH stop codon. Synthetic genes were supplied in proprietary Eurofins vectors. After maxiprep (plasmid maxi kit, Qiagen), 15 μg of plasmid DNA was digested with AfeI and XbaI (both NEB) and the insert gel purified (QIAquick gel extraction kit, Qiagen). This insert was introduced into AfeI/XbaI digested vector pOrigHiB (Metheringham et al. 2009) by ligation (T4 DNA ligase, NEB, following manufacturer's recommendations). Following sequence confirmation and maxiprep, 15 μg of plasmid DNA was digested with AfeI and AvrII (both NEB) and the insert gel purified. This insert was then introduced into AfeI/AvrII digested vector pDCOrig by ligation.

HEK293 Transfection and mAb Purification mAb constructs were obtained following transient transfections of Expi293F™ cells using the ExpiFectamine™ 293 Transfection kit (Gibco, LifeTechnologies). Briefly, HEK293 cells in suspension (100 ml, $2 \times 10^6$/ml) were transfected with 100 μg DNA and conditioned medium harvested at day seven post-transfection. Conditioned transfection supernatant was filtered through 0.22 μm bottle top filters (Merck Millipore) and sodium azide added to a final concentration of 0.2% (w/v). Antibody was purified on protein G columns (HiTrap ProteinG HP, GE Healthcare) using an AKTA FPLC (GE Healthcare). Columns were washed with PBS/Tris buffer (PBS with 50 mM Tris/HCl, pH7.0) before antibody elution with a rapid (2 ml) gradient into 100 mM glycine, pH12 (supplemented with 0.05% v/v Tween 20), collecting 2 ml fractions. Fractions containing mAb were pooled and neutralized (using 1M HCl) and the concentration determined. All transiently expressed mAb constructs were then analysed for cell binding, compared to the parental mAbs, using flow cytometry as a read-out for correct folding of the mAb constructs (data not shown).

Indirect Immunofluorescence and Flow Cytometry

Cancer cells ($1 \times 10^5$) were incubated with primary mAbs (at 33.3 nmol/L or titrated) for 1 h at 4° C., as previously described (Chua et al. 2015) followed by 1 h incubation at 4° C. with anti-mouse/anti-human FITC labelled secondary antibody, and fixing in 0.4% formaldehyde. Stained samples were analysed on a MACSQuant® 10 flow cytometer and analysed using FlowJo v10.

Functional Affinity Determination

The kinetic parameters of the 88 and 129 mAbs binding to Lewis$^a$—or sialyl-Lewis$^a$-APD-HSA were determined by Surface Plasmon Resonance (SPR, Biacore® 3000, GE Healthcare). Increasing concentrations (0.3 nmol/L-200 nmol/L) of mAb were injected across a CM5 chip and data were fitted to a heterogeneous ligand binding model using BIAevaluation 4.1. The chip contained four cells, two of which, HSA-coated (in-line reference cells), the other two were coated with low (30-80 response units (RU)) and high amounts (360-390 RU) of the respective glycan-APD-HSA.

The kinetic parameters of Trastuzumab antibody versus Trastuzumab engineered antibody variants binding to its ligand, HER2 was determined by SPR (Biacore® T200, Cytiva, formerly GE Healthcare). Increasing concentrations (90.0 nM to 0.37 nM of antibody were injected across a CM5 chip coated with anti-His antibody and captured His-tagged HER2

In Vitro Cytotoxicity

PI uptake as well as proliferation inhibition was performed to analyse the direct cytotoxic effect of the mAbs. COLO205, HCT-15 or BT474 cells ($5\times10^4$) were incubated with mAbs for 2 hours at 37° C. followed by the addition of 1 µg of PI for 30 minutes. Cells were resuspended in PBS and run on a Beckman Coulter FC-500 or on a MACSQuant® 10 flow cytometer and analysed with WinMDI 2.9 or FlowJo v10 software, respectively.

Proliferation inhibition by the constructs was assessed by using the water-soluble tetrazolium salt WST-8 (CCK8 kit, Sigma-Aldrich) to measure the activity of cellular hydrogenases which is directly proportional to the number of viable cells. Briefly, after overnight plating of cancer cells (1000-2000 cells/90 µl/well), constructs were added at different concentrations in a final volume of 10 µl/well and the plates were incubated at 37° C., (5% $CO_2$) for 72-96 h. WST-8 reagent was then added (10 µl/well) and after a further 3 h incubation, the plates were read at 450 nm (Tecan Infinite F50) and percentage inhibition calculated. $EC_{50}$ values were determined using nonlinear regression (curve fit) with GraphPad Prism v 8.0 (GraphPad Inc, La Jolla, CA).

Scanning Electron Microscopy

HCT-15 or COLO205 cells ($1\times10^5$) were grown on sterile coverslips for 24 hours prior to mAb (0.2 µmol/L) addition for 18 hours at 37° C. Controls included medium alone and 0.5% (v/v) hydrogen peroxide ($H_2O_2$) (Sigma). Cells were washed with pre-warmed 0.1 M sodium cacodylate buffer pH7.4 (SDB) and fixed with 12.5% (v/v) glutaraldehyde for 24 hours. Fixed cells were washed twice with SDB and post-fixed with 1% (v/v) osmium tetroxide (pH 7.4) for 45 minutes. After a final wash with $H_2O$, the cells were dehydrated in increasing concentrations of ethanol and exposed to critical point drying, before sputtering with gold, prior to SEM analysis (JSM-840 SEM, JEOL).

In Vivo Model

The study was conducted by CrownBio UK under a UK Home Office Licence in accordance with NCRI, LASA and FELAS guidelines. Subcutaneous tumours of a human colorectal adenocarcinoma model of COLO 205 were established in age-matched female BALB/c nude (Charles River, UK) mice via injection of $5\times10^6$ viable cells in 0.1 ml serum free RPMI:Matrigel (1:1) into the left flank of each mouse. Mice (n=10) were randomly allocated to treatment groups based on their mean tumour volume (~103 mm³±13 mm³) on study day 6 and dosed intravenously (i.v.), biweekly, with mAbs (0.1 mg) or vehicle (PBS, 100 µl) up until week 5. Body weight and tumour volume were assessed three times weekly and reduction in tumour volume analysed statistically using a two-way ANOVA test with Bonferroni's post-test (interaction factors; GraphPad Prism v 7.4 (GraphPad Inc, La Jolla, CA)).

EXAMPLES

The present invention will now be described further with reference to the following examples and the accompanying drawings.

Example 1. M88G3 Exhibits Avid Glycan Binding as Well as Direct Cytotoxicity in the Absence Of Complement and Immune Effector Cells, Both of which are Reduced Upon Chimerisation to 88IgG1

Figure 1B:
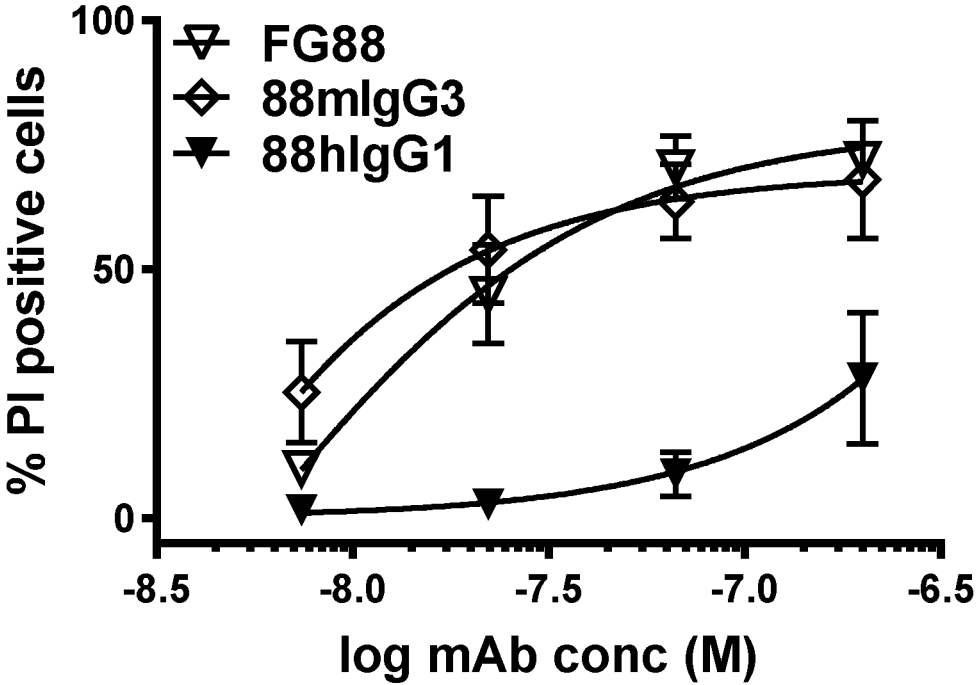
Figure 1C:
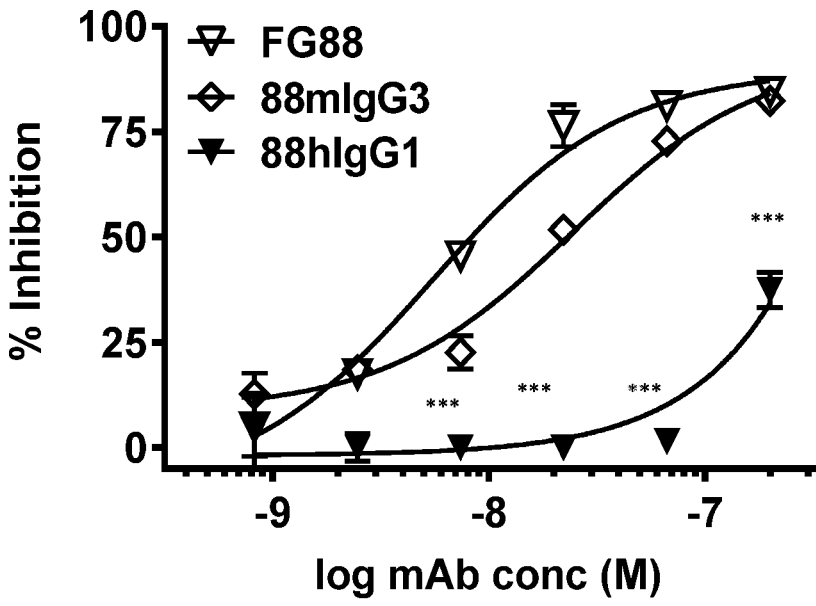
Figure 1D:
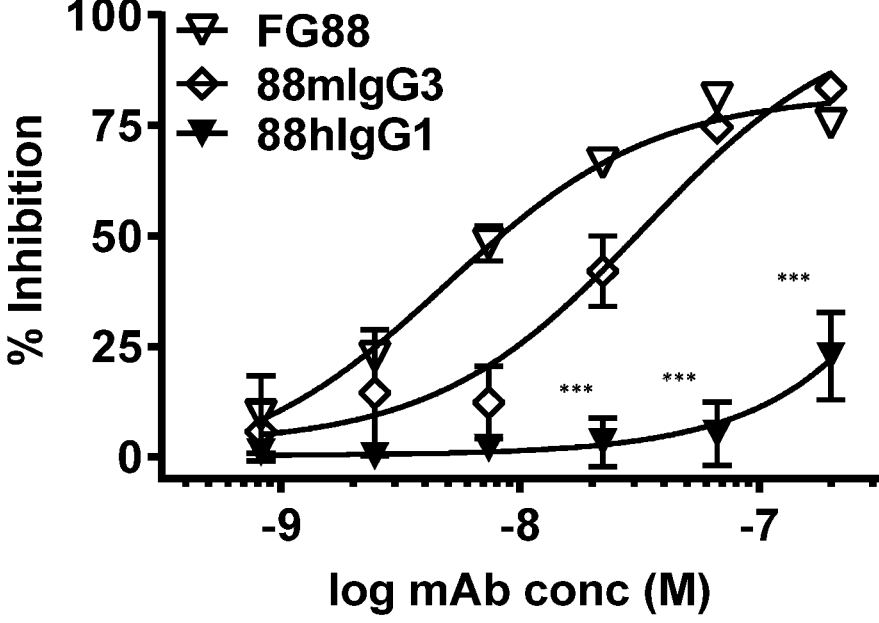

It has previously shown that the hybridoma-produced mIgG3 mAb FG88.2 exerts a direct cytotoxic effect on high-binding cancer cell lines, such as COLO205 and HCT15, in the absence of complement or effector cells (Chua et al. 2015). This direct cytotoxicity involved mAb-induced cellular aggregation, proliferation inhibition as well as irregular pore formation through an oncolytic mechanism. We subsequently created a chimeric, HEK293-expresssed, IgG1 mAb, 88IgG1, for clinical exploitation. 88IgG1 maintained equivalent HCT15 and COLO205 cancer cell binding levels (FIG. 1A), compared to the hybridoma-produced FG88.2, as well as the HEK293-expressed 88mIgG3. The latter mAb was generated to rule out expression system related-effects such as differential Fc glycosylation, due to the use of murine hybridoma cells versus HEK293 cells. Surprisingly, 88IgG1, exhibited significantly reduced direct cytotoxicity on COLO205 and HCT15, across two functional assays, PI uptake and proliferation inhibition, compared to 88mIgG3 (FIG. 1B-D). 88mIgG3 also displayed a modest reduction in direct cytotoxicity compared to the hybridoma-produced FG88.2, suggesting that differential glycosylation of the Fc region by the two expression settings (mouse hybridoma versus HEK293 cells) may contribute to the effect. This suggests the direct cell killing was related to the kinetic binding of the different isotypes. Consequently, the kinetic binding of our isotype-switched mAbs was analysed on a Lewis$^a$-APD-HSA coated chip using SPR (Table 1). FG88.2 displayed avid Lewis$^a$-APD-HSA binding with fast apparent on-rates ($k_{on}$~$10^4$ 1/smol/L) and very slow off rates ($k_{on}$~$10^{-6}$ 1/s) on the high-density flow cell. The HEK293-produced 88mIgG3 exhibited an apparent faster on-rate ($k_{on}$~$10^5$ 1/smol/L) and a somewhat faster off-rate ($k_{off}$-$10^{-4}$ 1/s) compared to FG88.2, that could explain the slightly reduced cytotoxicity compared to FG88.2. In comparison, 88IgG1 bound its target with an apparent fast on-rate ($k_{on}$~$10^5$ 1/smol/L), but in contrast to the mIgG3 isotypes displayed a much faster dissociation phase (apparent $k_{off}$~$10^{-2}$ 1/smol/L), that is likely to underly its reduced cytotoxic activity upon cancer cell binding. The mAb binding behaviour on the low-density flow cell was largely comparable between the three mAbs with equilibrium dissociation constants ($K_d$) of the order of $10^{-8}$ mol/L for all three mAbs.

Example 2. Domain Analysis of the mIgG3 Constant Region Suggests a Major Contribution by the mIgG3 CH3 Domain with a Minor Involvement of the CH2

Figure 2A:
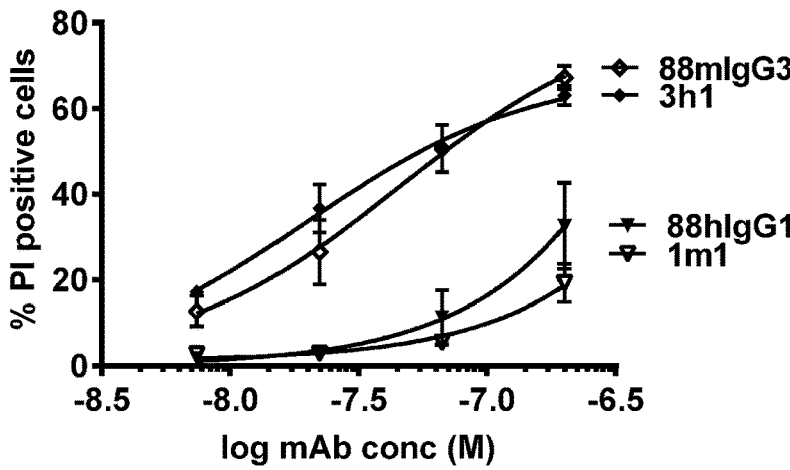
FIG. 2. mIgG3 CH3 and to a lesser extent CH2 contribute to the direct cytotoxicity and improved functional affinity. Constant domain shuffling suggests no significant contribution by CH1 to direct cytotoxicity (PI uptake, HCT15, Panel A; proliferation inhibition on COLO205, panel B). In contrast, CH3 (1m3 and 3h3) contributes significantly to direct cytotoxicity, with a minor contribution by mCH2 only evident in a loss-of-function approach (3h2) (PI uptake, HCT15, Panel C; proliferation inhibition, COLO205, panel D). Significantly increased functional affinity and decreased off-rate by 1 m3; with significantly decreased functional affinity and increased off-rate by 3h2 and more pronounced by 3h3, confirming the major CH3 and minor CH2 contributions (Panel E, F). Significance versus respective parental constructs was deduced from two-way ANOVA (direct cytotoxicity) or one-way ANOVA (functional affinity, off-rate), with Dunnett's corrections for multiple comparisons.
Figure 2B:
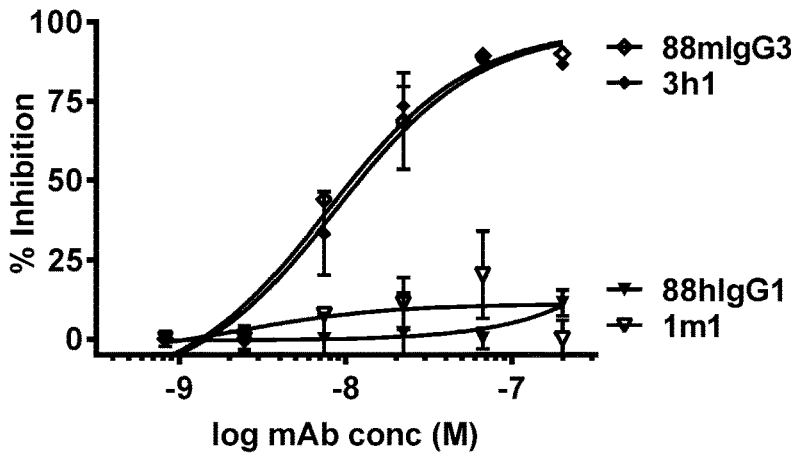
Figure 2C:
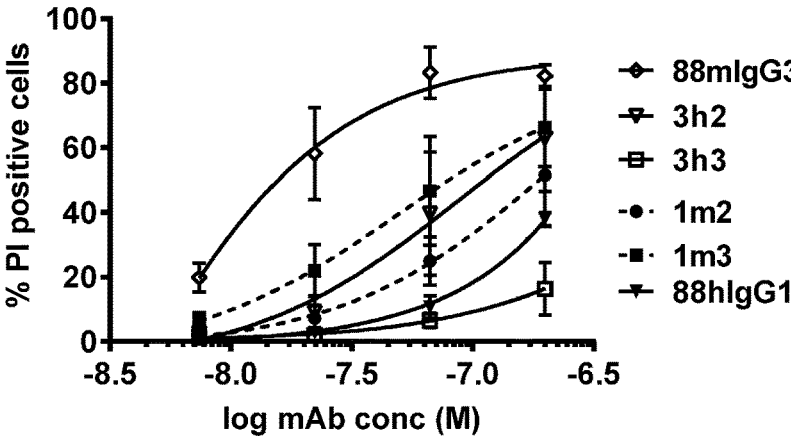
Figure 2D:
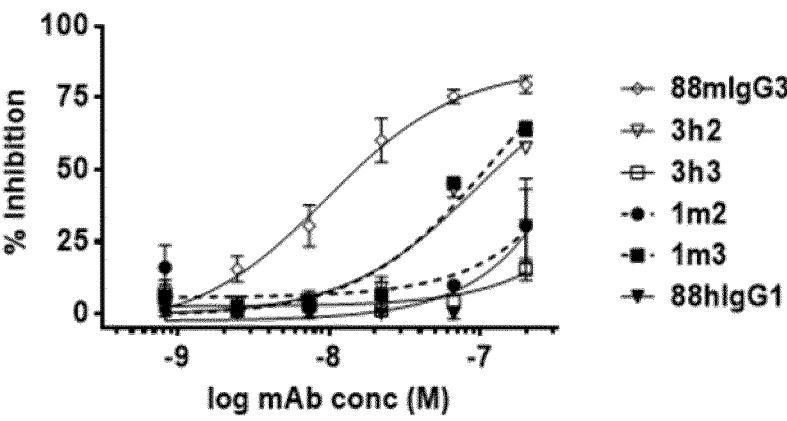
Figure 2E:
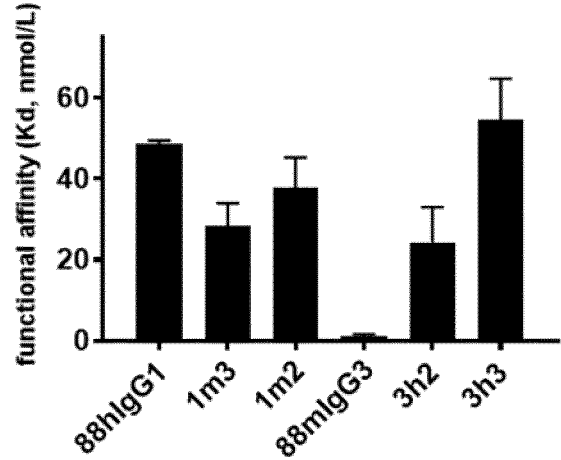
Figure 2F:
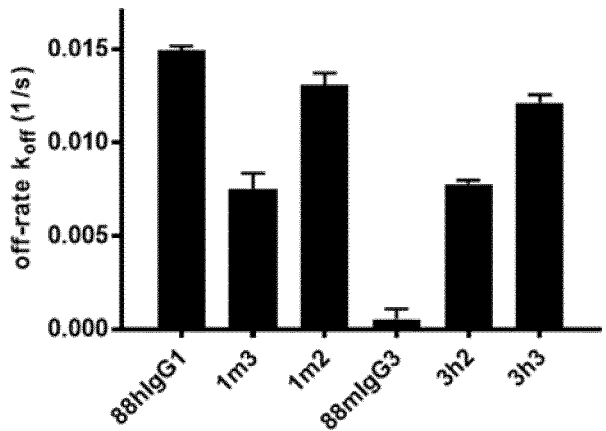

Collectively, the results suggested that the high Lewis$^a$-APD-HSA functional affinity exhibited by FG88 and 88mIgG3, predominantly driven by their slow dissociation, potentially resulting from the intermolecular cooperativity of this isotype, contributed to their direct cytotoxic effect on high-binding cancer cell lines. We thus set out to engineer a IgG1 cancer glycan targeting mAb with direct cytotoxic activity, via the transfer of selected mIgG3 constant region residues into 88IgG1. Firstly, mIgG3 contributing regions were identified through the creation of hybrid 88IgG1 constructs, containing mIgG3 CH1, CH2 or CH3 domains. Preliminary analyses ascertained that mIgG3 CH1 had a negligible contribution to the direct cytotoxicity ability of 88mIgG3, as introducing mIgG3 CH1 into 88IgG1 (1 ml) did not lead to a significant increase in cytotoxicity (FIGS. 2A and 2B). Conversely, introducing IG1 CH1 into 88mIgG3 (3h1), equally, did not instigate a significant reduction in killing activity (FIGS. 2A and 2B). Next, in a gain-of-function approach, the mIgG3 CH2 and CH3 domains, separately, were introduced in 88IgG1. 88IgG1 containing murine CH3 (1 m3) exhibited a significant gain in PI uptake on HCT15, as well a significant increased proliferation inhibition of COLO205 cells, when compared to 881gG1 (FIGS. 2C and D). Introducing murine CH2 into 881gG1 (1m2) led to small, but not significant, increase in killing activity across both assays (FIGS. 2C and D). As a confirmation of the contributions made by both domains, the reverse strategy was followed whereby a loss of cytotoxicity activity was evaluated due to the introduction IgG1 CH2 or CH3 domains into 88mIgG3. This scenario led to a significant decrease in cytotoxicity for 88mG3 containing IgG1 CH3 (3h3), corroborating the previous gain-of-function results. Importantly, this strategy also identified a small contribution by the murine CH2, as 88mIgG3 containing human CH2 (3h2) exhibited a significant decrease in cytotoxicity activity (FIGS. 2C and D). Next, the kinetic binding behaviour of the hybrid constructs was analysed. The hybrid construct 1m3 exhibited a modest, but significant increase in functional affinity (decreased $K_d$), whilst 3h3, containing human CH3, displayed a significant decrease in functional affinity (increased $K_d$, FIG. 2E), in both cases, mirroring the direct cytotoxicity. Human CH2 in construct 3h2 also led to a modest, but significant drop in functional affinity. In all cases, the changes in functional affinity were predominantly driven by changes in the off-rate of the mAbs, with 1m3 showing a significantly decreased off-rate compared to 881gG1 and 3h3, as well as 3h2, exhibiting a significantly increased off-rate compared to 88mIgG3 (FIG. 2F). Murine CH2 in construct 1m2 did not lead to increased functional affinity nor a decreased off-rate, underlying the insignificant cytotoxicity of this construct compared to 881gG1 (FIGS. 2C and D). Taken together the results indicate that the murine CH3 has a more pronounced contribution to cytotoxicity, as well as kinetic binding, whereas the contribution by murine CH2 is smaller, only observed in a loss-of-function setting.

Figure 3A:
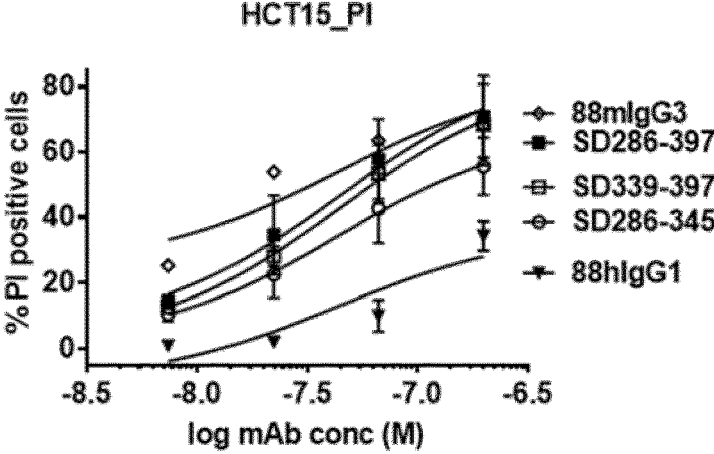
FIG. 3. SD286-397 encompassing the CH2:CH3 junction underlies mIgG3 direct cytotoxicity and improved functional affinity. Subdomain divisions of CH2CH3 identify two regions that do not contribute: SD232-294 and SD390-447, as well as two regions that significantly contribute to direct cytotoxicity and functional affinity: SD286-345 (CH2) as well as SD339-397 (CH3). Significantly increased PI uptake by both constructs and the combination (SD286-397) compared to 881gG1 on HCT15 (Panel A) and COLO205 (Panel B). Significantly increased proliferation inhibition by both constructs and the combination compared to 881gG1 on COLO205 (Panel C) and HCT15 (Panel D). Significantly increased functional affinity (SPR), resulting mainly from reduced off-rates by the two aforementioned constructs (Panels E and F, respectively). Significantly reduced CDC activity (HCT15) by SD339-397 compared to 88IgG1 (Panel G); maintenance of ADCC activity (COLO205) by the aforementioned constructs (Panel H). Significance versus respective parental constructs was deduced from two-way ANOVA (direct cytotoxicity) or one-way ANOVA (functional affinity, off-rate, effector functions), with Dunnett's corrections for multiple comparisons.
Figure 3B:
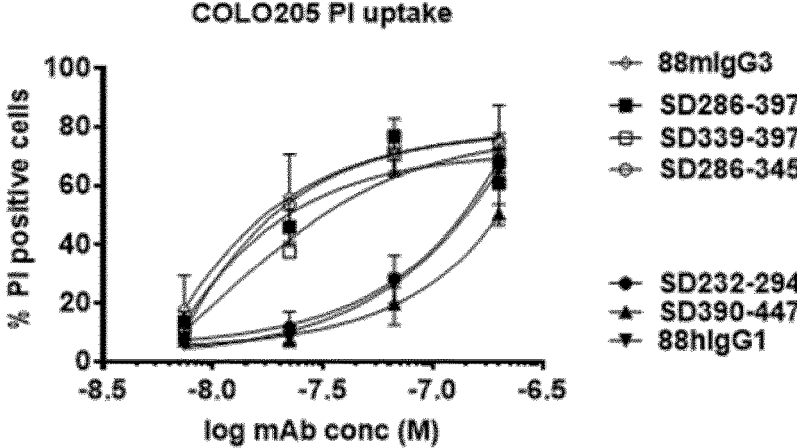
Figure 3C:
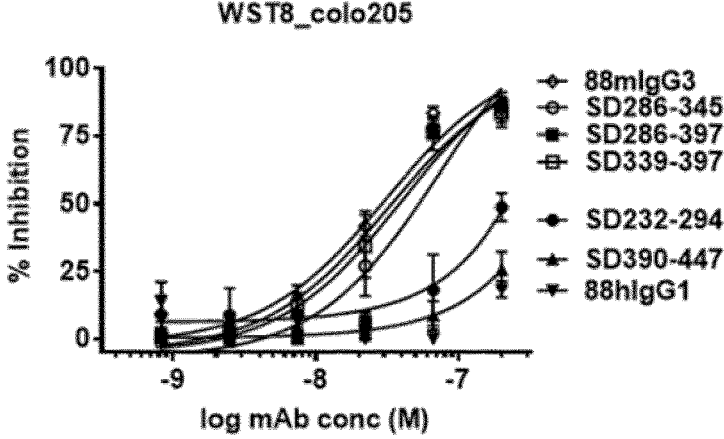

Example 3. Discontinuous Sequences within the CH2-CH3 Region of Aa 286-397 are Essential for Killing Activity and Increased Functional Affinity As the cytotoxic effect endowed by the murine CH3 was not complete, and in order to further narrow down the other contributing residues, we designed hybrid 88 mAb constructs where the CH2 and CH3 domains were further subdivided into two subdomains (SD) with junction regions containing a 10 residue overlap: CH2: SD232-294 and SD286-345 and CH3: SD339-397 and SD390-447. On COLO205, both SD339-397 and SD286-345 afforded a similar significant increase in cytotoxicity, most evident at the lower concentrations, whereas SD232-294 as well as SD390-447, alone, or in combination (not shown), were dispensable for cytotoxicity (FIGS. 3A and C). On HCT15 however, the significant contribution by residues within SD339-397 was larger than that of SD286-345 (FIGS. 3B and D), suggesting that subtle differences in glyco-antigen density and composition can modulate mAb binding and ensuing cytotoxic activity. Strikingly, 88IgG1, containing the combined mIgG3 SD286-345 and SD339-397 (SD286-397), recovered virtually all the cytotoxicity of 88mIgG3 on both cell lines and across both assays (FIG. 3A-D), obviating the need for adding additional subdomains. Functional affinity analysis of the subdomain constructs, compared to 88IgG1, revealed a striking improvement in functional affinity for SD286-397, as well as SD339-397, both now matching the 88mIgG3 functional affinity, with a more modest improvement for SD286-345 (FIG. 3E). The improved functional affinity resulted mainly from a dramatically reduced apparent off-rate (~$10^{-6}$ 1/s) for SD286-397 as well as SD339-397, with the SD286-345 off-rate showing a more modest improvement (~$10^{-3}$ 1/s) (FIG. 3F). These results add further weight to the cytotoxicity observations and suggest that creating a mAb with a reduced target dissociation rate supports direct cytotoxicity.

Figure 3G:
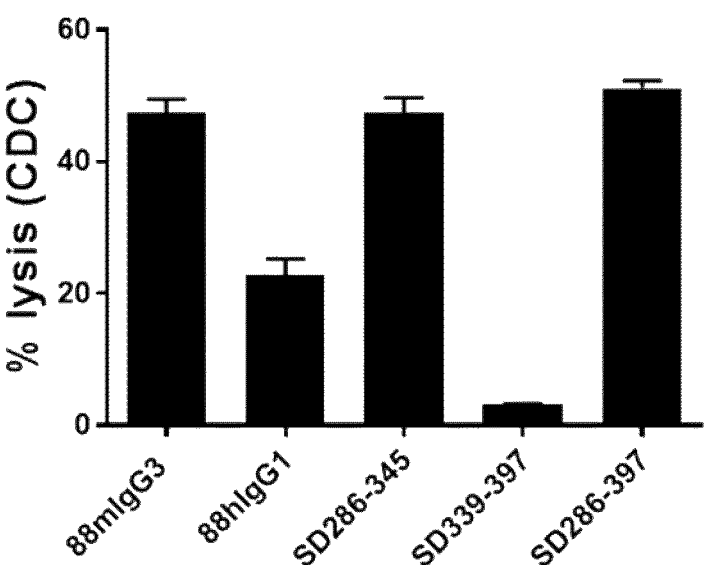
Figure 3H:
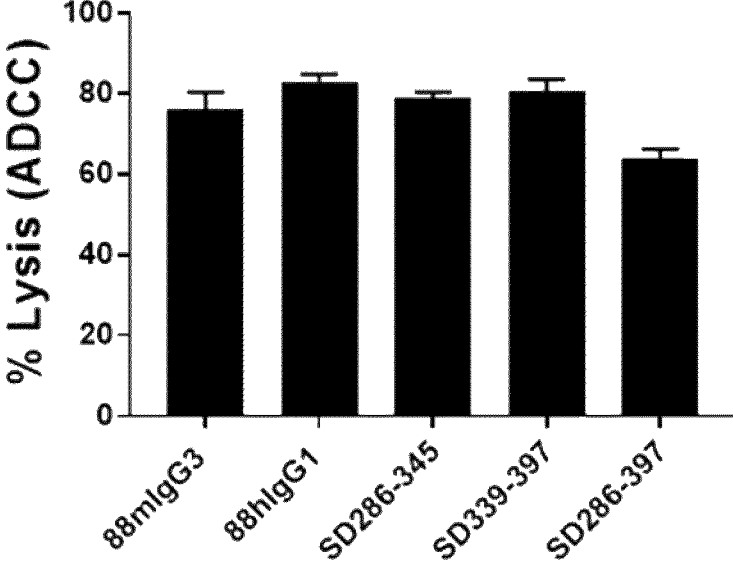
Figure 4A:
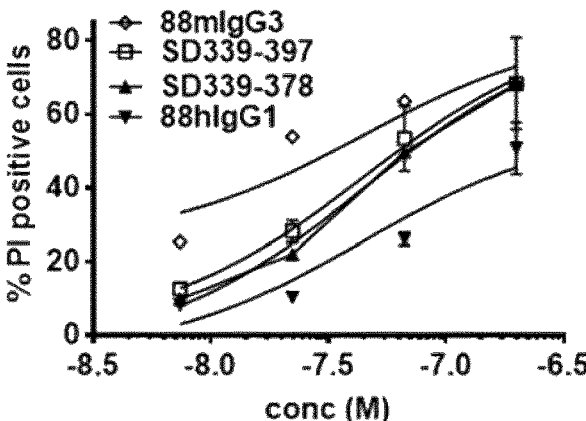
FIG. 4. Discontinuous region consisting of 286-306 combined with 339-378 imparts direct cytotoxicity and enhanced functional affinity, whilst maintaining immune effector functions. Significantly increased PI uptake (Panel A) and proliferation inhibition (Panel B) by SD339-378 compared to 88IgG1 on HCT15. Significantly reduced PI uptake by SD307-345 compared to SD286-345, suggesting a contribution by SD286-306 (Panel C). Significantly increased proliferation inhibition by the combination of SD286-306+339-378 compared to 88IgG1 on HCT15 (Panel D) and COLO205 (Panel E), as well as PI uptake on COLO205 (Panel F). Significantly increased functional affinity (SPR) by SD286-306+339-378 compared to 88IgG1 (Panel G). Maintenance of CDC activity on HCT15 (Panel H) and ADCC on COLO205 (Panel I) by SD286-306+339-378 compared to 88IgG1. Significance versus respective parental constructs was deduced from two-way ANOVA (direct cytotoxicity) or one-way ANOVA (functional affinity, and effector functions), with Dunnett's corrections for multiple comparisons.
Figure 4B:
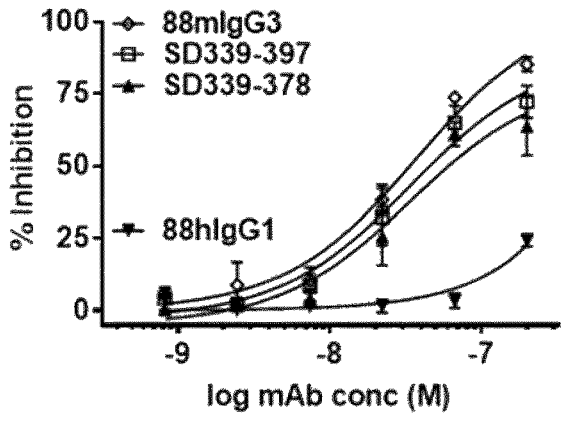
Figure 4C:
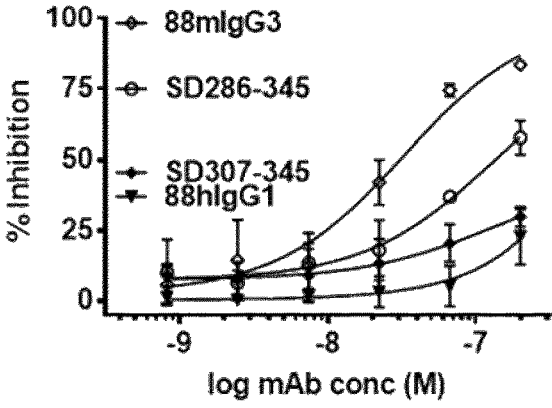
Figure 4D:
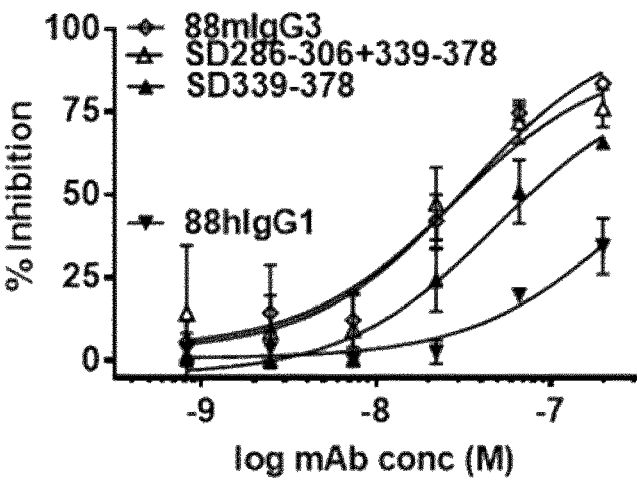
Figure 4E:
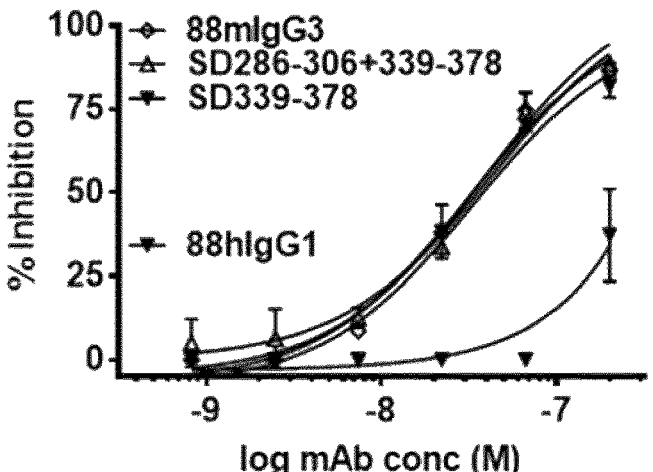
Figure 4F:
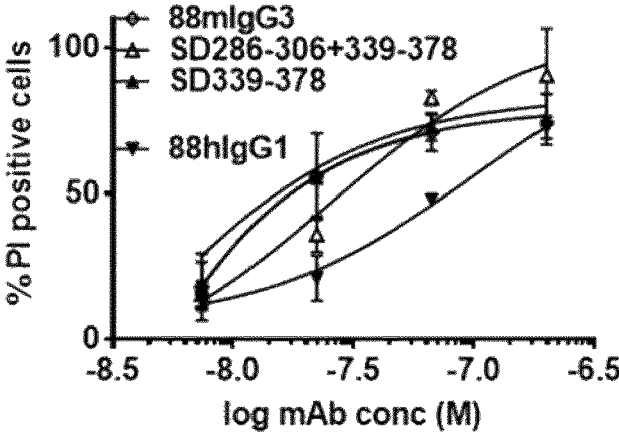
Figures 4G, 4H, 4I:
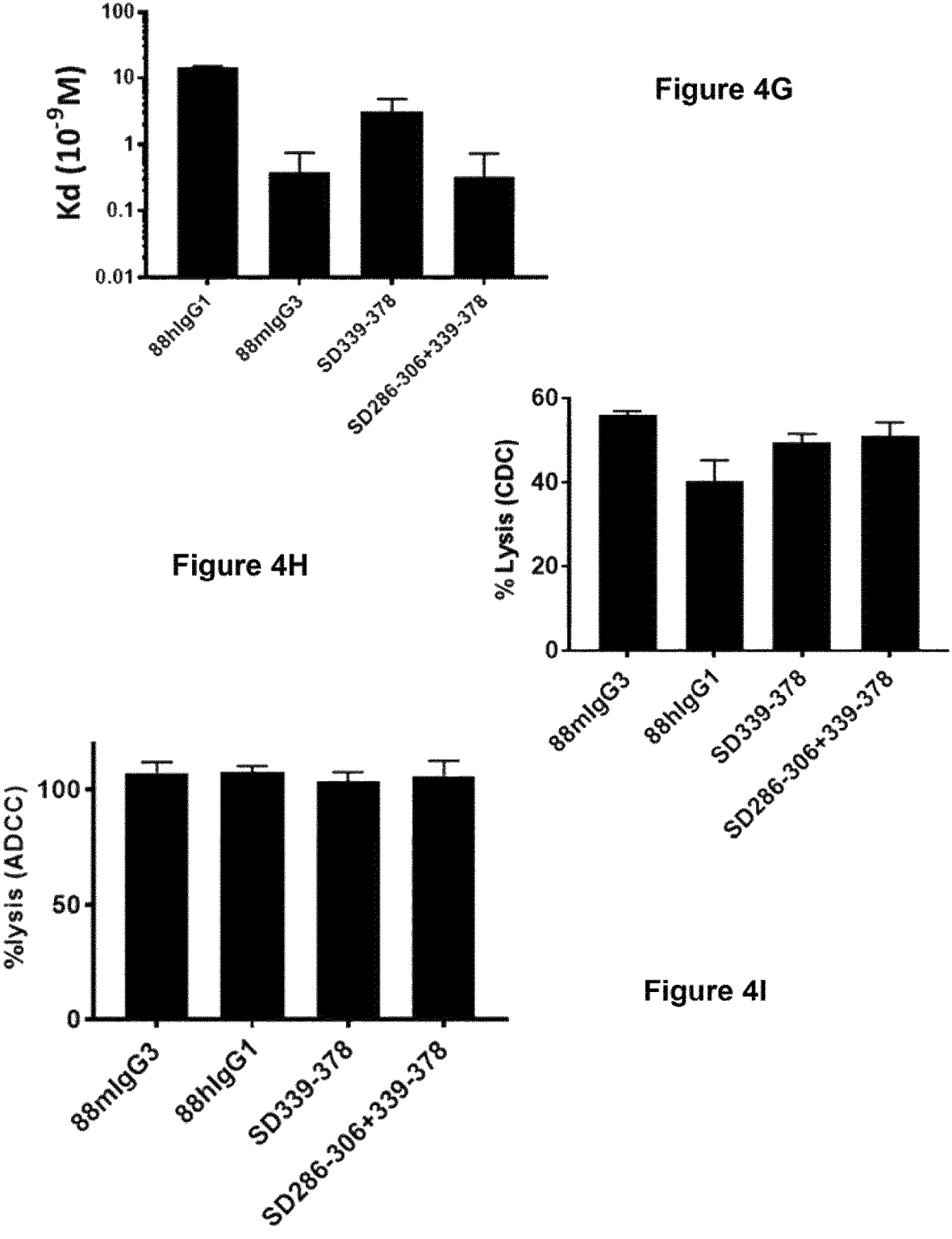

Although SD339-397, with 27 mIgG3 residues, recapitulated up to 90% of the desirable attributes of 88mIgG3, notably the slow dissociation and enhanced cytotoxicity, it exhibited a significantly reduced CDC activity compared to 881gG1 (FIG. 3G), necessitating the use of SD286-397 for further development. In contrast, ADCC activity of SD339-397 was not reduced compared to 88IgG1 (FIG. 3H). Although SD286-397 fully recapitulated 88mIgG3 cytotoxicity, it still contained 41 mIgG3 residues. Consequently, additional subdivisions of SD286-345 and SD339-397 were analysed for cytotoxic activity and functional affinity. This analysis highlighted two areas, in SD339-397 and SD286-345, respectively, that contributed to direct cytotoxicity. Firstly, SD339-378, containing 20 mIgG3-specific residues, upon introduction in 88IgG1 led to a significant regain of cytotoxicity to within ~80% to 90% of mIgG3 cytotoxicity across both assays (FIGS. 4A and B). This region, also instilled a significant increase in functional affinity, compared to 88IgG1, but this improvement was not as pronounced as in the case of SD339-397 (FIG. 4G). Within the same set of constructs, we identified another region of interest via the loss-of-function approach. The significant reduction in cytotoxicity by SD307-345 compared to SD286-345, implied a further contribution by residues 286-306 (FIG. 4C). Collectively, the results suggested that a construct containing the combination of residues 286-306 and 339-378, totaling 26 mIgG3-specific residues, could potentially fully recapitulate 88mIgG3 direct cytotoxicity and functional affinity. To test this hypothesis, the cytotoxic activity and functional affinity of SD286-306+339-378 was evaluated. SD286–306+339–378 exhibited significantly improved direct cytotoxicity, compared to 88 IgG1, on both cell lines, now matching 88mIgG3 cytotoxicity (FIG. 4D-F). SPR analysis of SD286–306+339–378 revealed a significantly improved functional affinity compared to 881gG1 with a $K_d$ (0.3×$10^{-9}$ nmol/L) and similar to 88mIgG3 (FIG. 4G). Importantly, neither the CDC activity, nor the ADCC activity of the SD286-306+339-378 construct was significantly different from that of 881gG1 (FIGS. 4H and I). The combination of improved functional affinity with direct cytotoxicity, as well as maintained immune effector functions, indicates that our SD286-306+339-378 hybrid IgG1 mimics the desirable attributes of 88mIgG3.

Example 4. Reversal of One in Silico Identified Immunogenic Cluster Generates the Lead Candidate, Improved 'i' 88G1, with Robust Cell Killing, Pore-Forming Ability and Sound Immune Effector Functions In order to assess the potential immunogenicity of our hybrid SD286-306+339-378 construct, created by the presence of 26 mIgG3 residues, we performed an in silico screen of the SD286–306+339–378 sequence for MHCII-binding epitopes (Immune Epitope Database, IEDB). Class II-restricted T helper cells are more relevant to the humoral immune response and predicted binding clusters have been shown to be strong indicators of T cell responses (Jawa et al. 2013). Two MHCII binding clusters, containing several high-scoring binding epitopes, were identified: cluster 1 (residues 294-315) and cluster 2 (residues 365-393) (FIG.

Figure 6A:
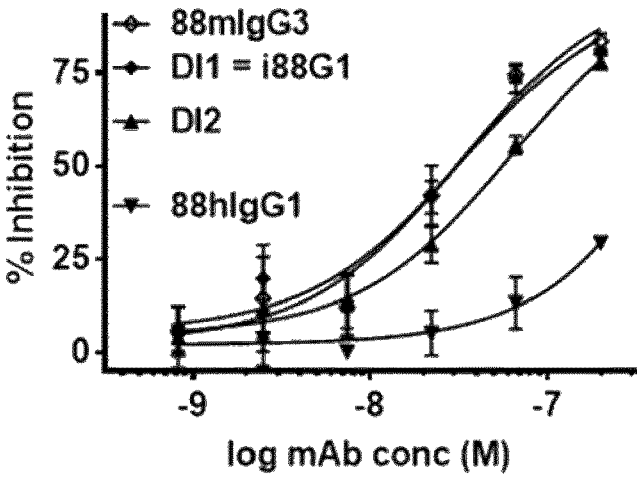
FIG. 6. i88G1 with direct cytotoxicity and enhanced functional affinity, whilst maintaining immune effector functions, exhibits pore forming ability. Significantly increased proliferation inhibition on HCT15 (Panel A) and COLO205 (Panel B) by i88G1 compared to 88IgG1. Significantly increased functional affinity (SPR) by i88G1 compared to 88IgG1 (Panel C). Slight but significant reduction in ADCC by i88G1 compared to 88IgG1 on COLO205 (Panel D) and significantly increased CDC activity by i88G1 compared to 88IgG1 on HCT15 (Panel E). Evidence of cellular detachment, aggregation and pore forming ability by i88G1 on HCT15 (Panel F).
Figure 6B:
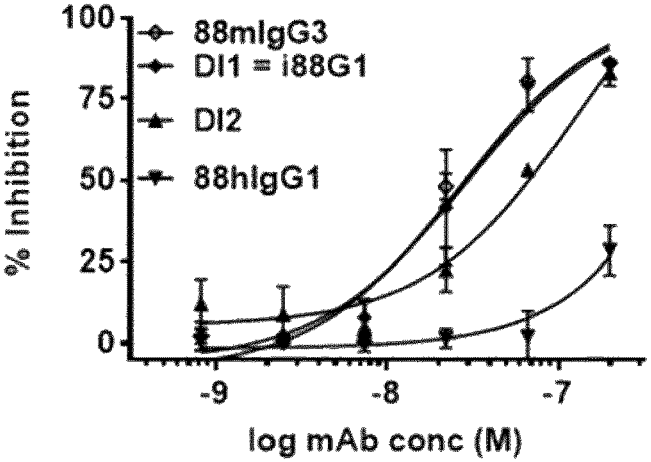
Figure 6C:
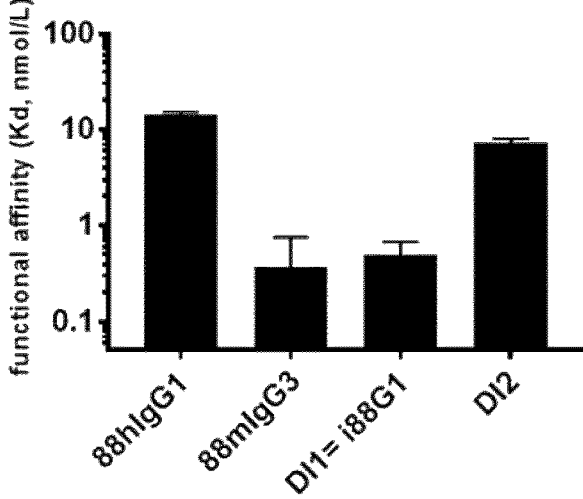
Figure 6D:
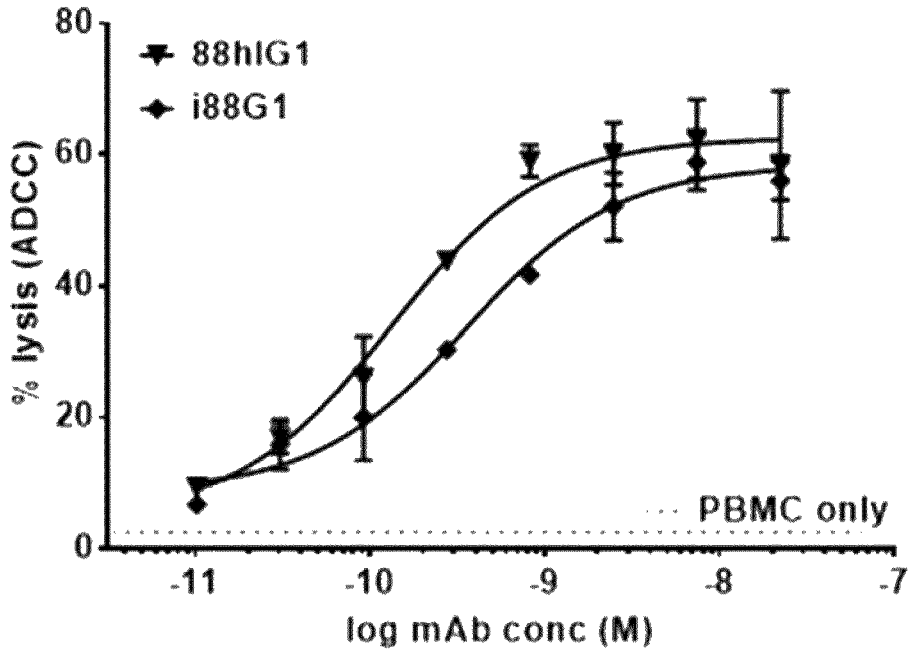
Figure 6E:
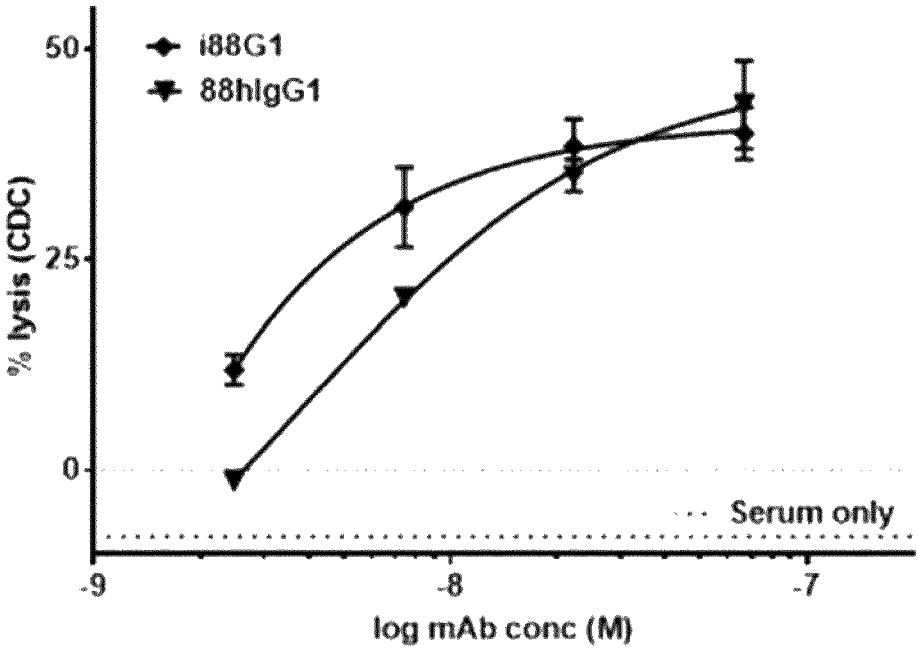

5/FIG. 20). Reversion of three murine residues, 294 (A to E), 300 (F to Y) and 305 (A to V) back to human residues, within the cluster 1, produced a human sequence section to which individuals would have been tolerized. Similarly, reversal of two residues 351 (I to L) and 371 (N to G), within the 339-378 region, removed two MHCII binding cores. We thus created two additional SD286-306+339-378-based constructs, based on the above in silico screen: clusters 1 (DI1) and 2 (DI2), containing three and two human reverted residues, respectively, and assayed their cytotoxicity. DI1, as well as DI2, maintained significantly improved cytotoxicity compared to 88IgG1, but DI2 showed a small, but consistent decreased activity compared to 88mIgG3 (FIGS. 6A and B). Additionally, in the case of 88DI1 the direct cytotoxicity coincided with a favourable functional affinity profile, with an apparent off-rate of ($\sim 10^{-4}$ 1/s) and a $K_d$ of $0.5\times10^{-9}$ nmol/L that was not significantly different from 88mIgG3 (FIG. 6C, Table 2). In contrast, DI2 displayed a significantly decreased functional affinity compared to 88mIgG3 (FIG. 6C). Based on these finding, we focused on 88DI1, containing 23 mIgG3 residues, now renamed improved 'i' (improved) 88G1, for further analysis of its immune effector functions. 88IgG1 showed potent ADCC activity on COLO205 with sub-nanomolar $EC_{50}$ (FIG. 6D), in line with the potent immune effector functions of FG88 (Chua et al. 2015). Similarly, i88G1 displayed potent ADCC with sub-nanomolar $EC_{50}$ (0.35 nmol/L) albeit somewhat reduced compared to 88IgG1 ($EC_{50}$ 0.13 nmol/L). The CDC activity of i88G1 was modestly improved compared to 88IgG1 (FIG. 6E, Table 2).

Figure 6F:
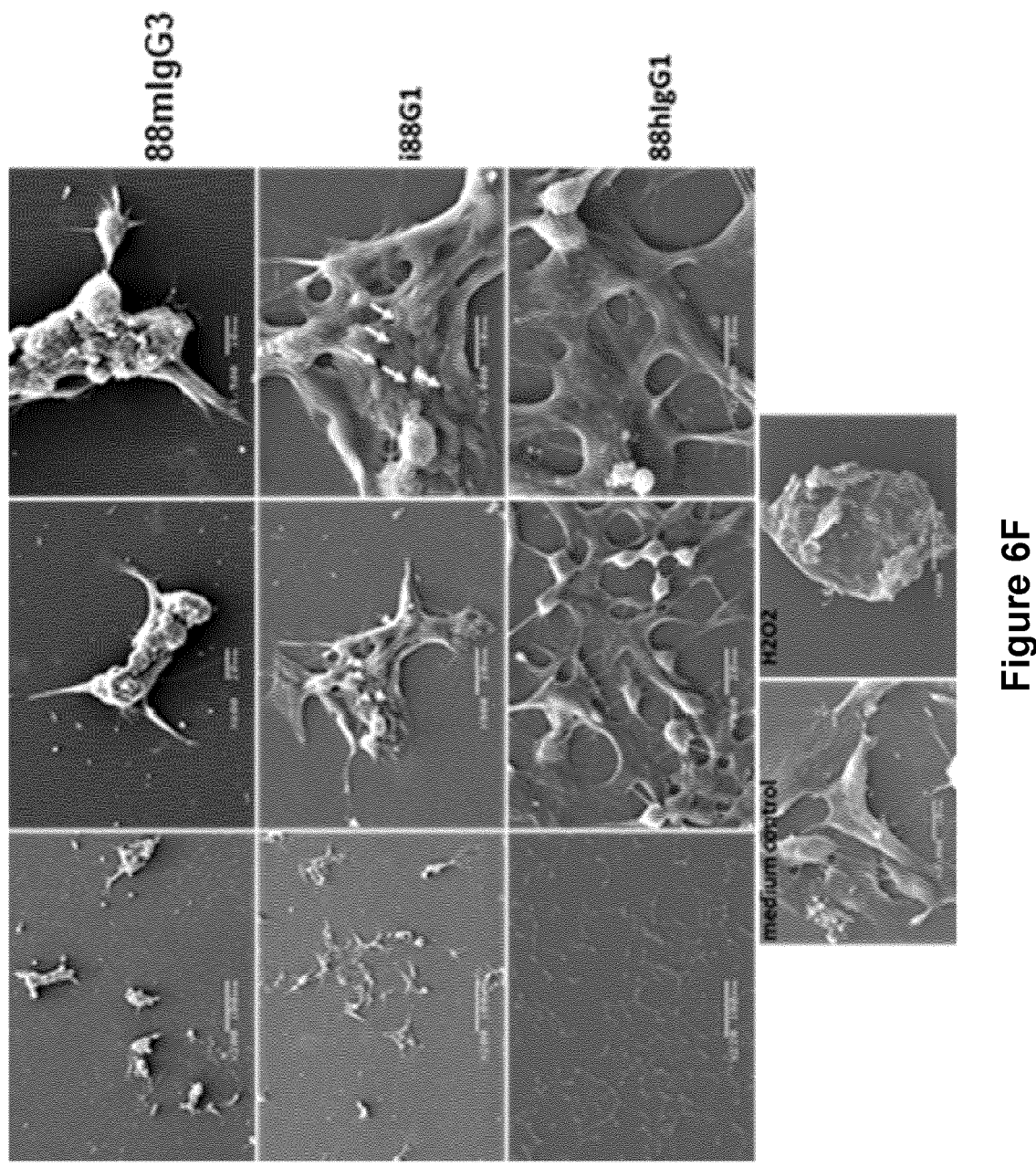

Earlier work on the parental hybridoma-produced FG88 mAb had demonstrated its pore-forming ability, which was surmised to underlie its cytotoxicity (Chua et al. 2015). We thus set out to analyse the pore-forming ability of i88G1 on HCT15, using SEM. Incubation of HCT15 with i88G1 or 88mIgG3, but not 88IgG1, resulted in monolayer disruption, cell rounding and clustering. At higher magnification, irregular pore formation was evident (FIG. 6F), mirroring the original data observed for the hybridoma-produced FG88 mAb (Chua et al. 2015).

Collectively the results indicate that transfer of selected regions from the mIgG3 constant region into the 88IgG1 backbone created a hybrid mAb with direct cell killing ability, increased functional affinity as well as robust immune effector functions.

Example 5. Transfer of the 'iG1' Sequences into an Alternative, Non-Killing, Glycan Binding mAb (129 IgG1) Creates a Cancer-Targeting mAb with Improved In Vitro and In Vivo Anti-Tumour Activity We recently described the generation of a sialyl-di-Lewis$^a$ recognizing mAb (129 mAb) with development potential for cancer immunotherapy. The 129 mAb has a more favourable tumour versus normal human tissue distribution compared to the above-described 88 mAb, predominantly resulting from its very restricted normal tissue reactivity. Neither the hybridoma-produced FG129, a murine IgG1 mAb, nor the chimeric 129IgG1, exhibit direct cytotoxicity. This led us to test the hypothesis that the introduction of the 23 above-selected mIgG3 constant region residues into the Fc region of CH129 would create an 'i'129G1 with direct cytotoxicity and improved functional affinity and thus exhibit superior clinical utility.

Figure 7A:
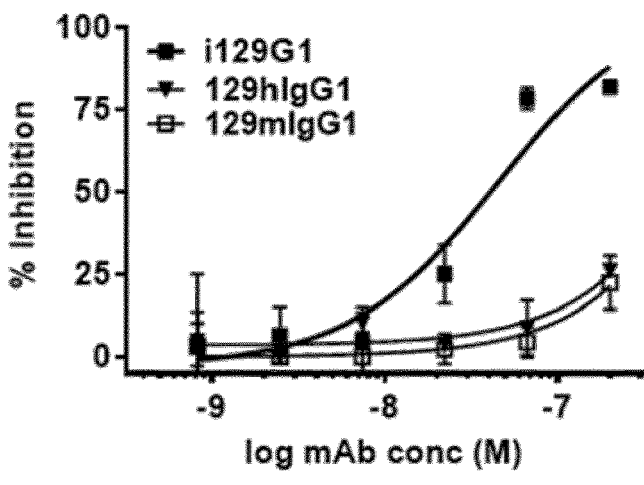
FIG. 7. i129G1 with direct cytotoxicity and enhanced functional affinity, whilst maintaining immune effector functions, exhibits pore forming ability and in vivo tumour control. Significantly increased proliferation inhibition (Panel A) and PI uptake (Panel B) on COLO205 (Panel A) by i129G1 compared to 129IgG1. Significantly increased functional affinity (SPR) by i129G1 compared to 129IgG1 (Panel C). i129G1 maintains some ADCC activity on COLO205, but significantly reduced compared to h129IgG1 (Panel D). CDC activity by i129G1 on COLO205 is significantly increased compared to 129IgG1 (Panel E). Evidence of cellular detachment, aggregation and pore forming ability by i129G1 on COLO205 (Panel F). Significant in vivo tumour control by i129G1 compared to vehicle control and compared to 129IgG1 in a COLO205 xenograft model (Balb/c mice) (Panel G). No significant effect on mean body weight during the course of the mouse study (Panel H). Significance versus respective parental constructs was deduced from two-way ANOVA (direct cytotoxicity, and in vivo tumour control) or one-way ANOVA (functional affinity and effector functions), with Dunnett's corrections for multiple comparisons.
Figure 7B:
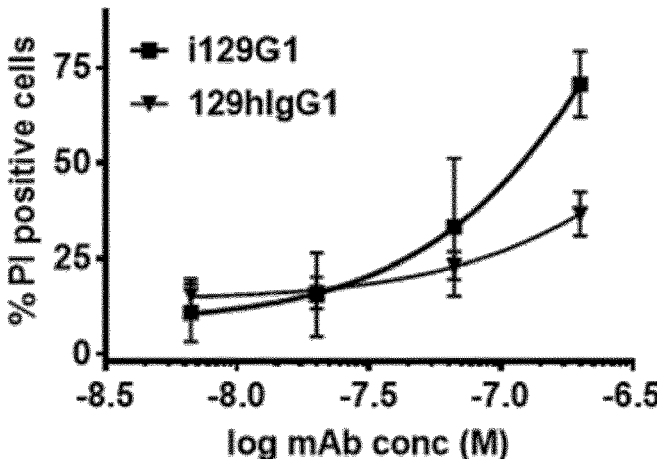
Figure 7C:
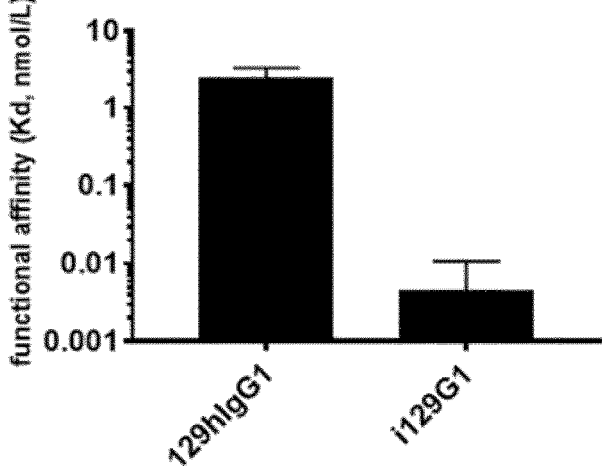
Figure 7D:
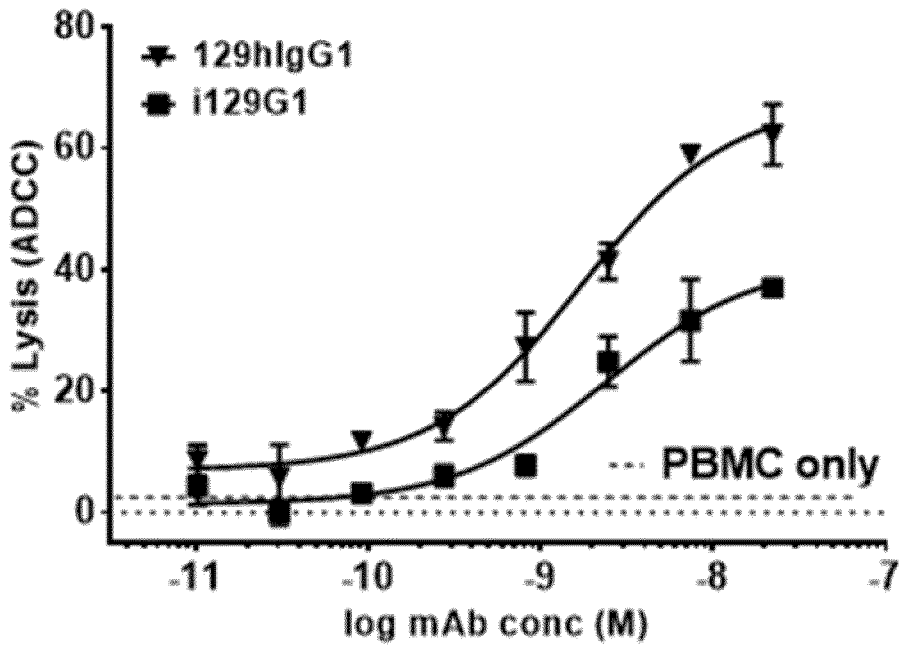
Figure 7E:
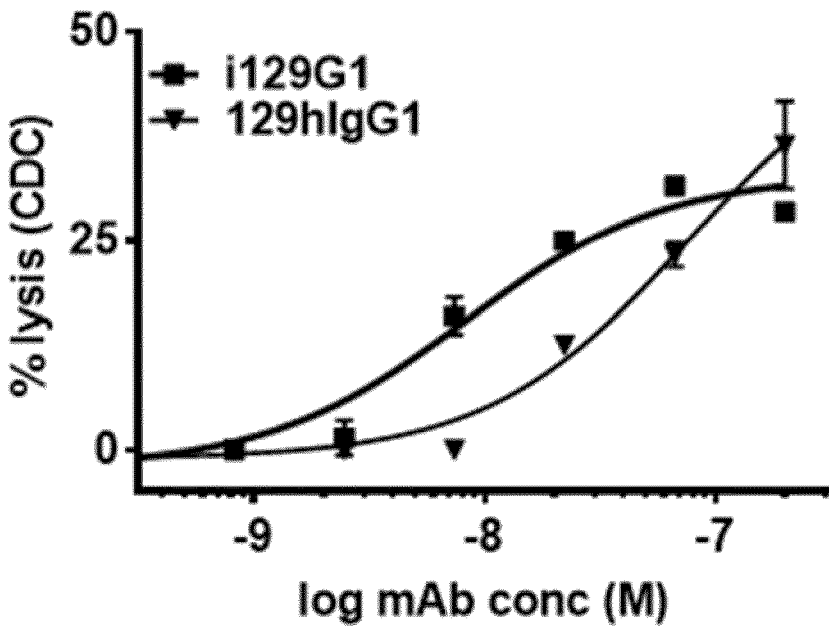
Figure 7F:
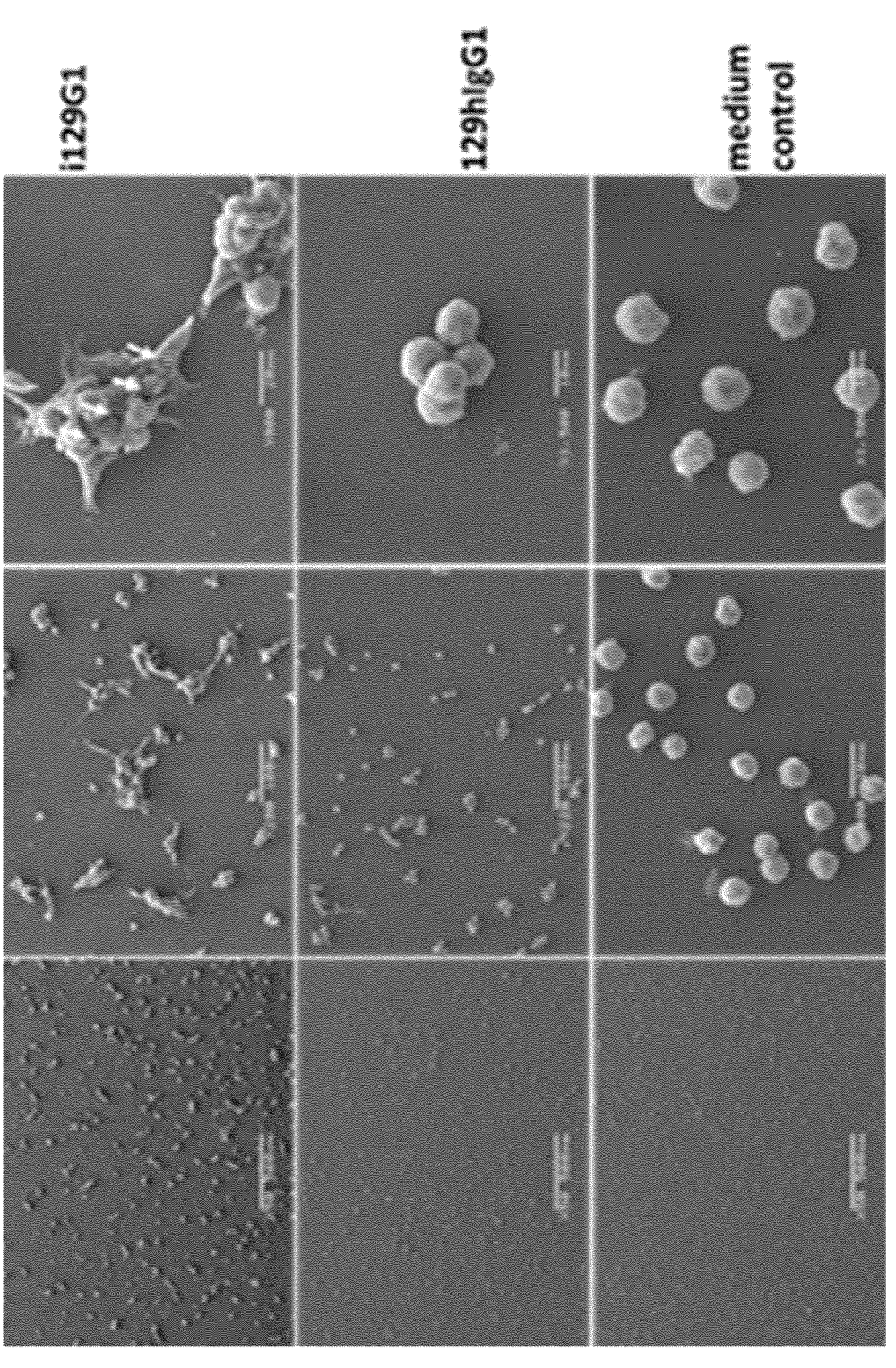

We evaluated the direct cytotoxicity ability of i129G1 on COLO205, previously shown to be a high-binding cancer cell line for the 129 mAb. The i129G1 displayed significantly improved (compared to 129IgG1), dose-dependent proliferation inhibition (FIG. 7A), with an $EC_{50}$ of 45.6 nmol/L, as well as a significantly improved, but more modest, PI uptake (FIG. 7B). Next, we analysed the functional affinity of i129G1 using a sialyl Lewis$^a$-APD-HSA-coated chip and SPR. The i129G1 mAb exhibited significantly improved functional affinity compared to 129IgG1 (FIG. 7C, Table 2), resulting predominantly from an improvement in off-rate by almost two logs ($2.6\times10^{-4}$ s$^{-1}$ and $5.5\times10^{-6}$ s$^{-1}$ for 129IgG1 and i129G1, respectively). 129IgG1 previously exerted potent ADCC effector functions on COLO205, consequently the ADCC as well as CDC activity of i129G1 on COLO205 were evaluated. The ADCC activity of i129G1 was significantly reduced compared to that of 129IgG1, but cell lysis was maintained in the nanomolar range ($EC_{50}$ of 2.4×nmol/L and 1.7×nmol/L, for i129G and 129IgG1, respectively) (FIG. 7D, Table 2). The CDC activity of i129G1, however, was significantly increased compared to the parental 129IgG1, with $EC_{50}$ of 8.2×nmol/L and 75×nmol/L, for i129G1 and 129IgG1, respectively (FIG. 7E, Table 2). The direct cytotoxicity as well as improved functional affinity of i129G1 led us to analyse its pore-forming ability on COLO205. The incubation of COLO205 with i129G1, caused the formation of large cell clumps with uneven surfaces, as well as the appearance of irregular pore-like structures (FIG. 7F). Incubation with 129IgG1, at the same concentration, also led to a degree of cell clumping, but smaller and fewer clumps were observed, without evidence of pore formation.

Figure 7G:
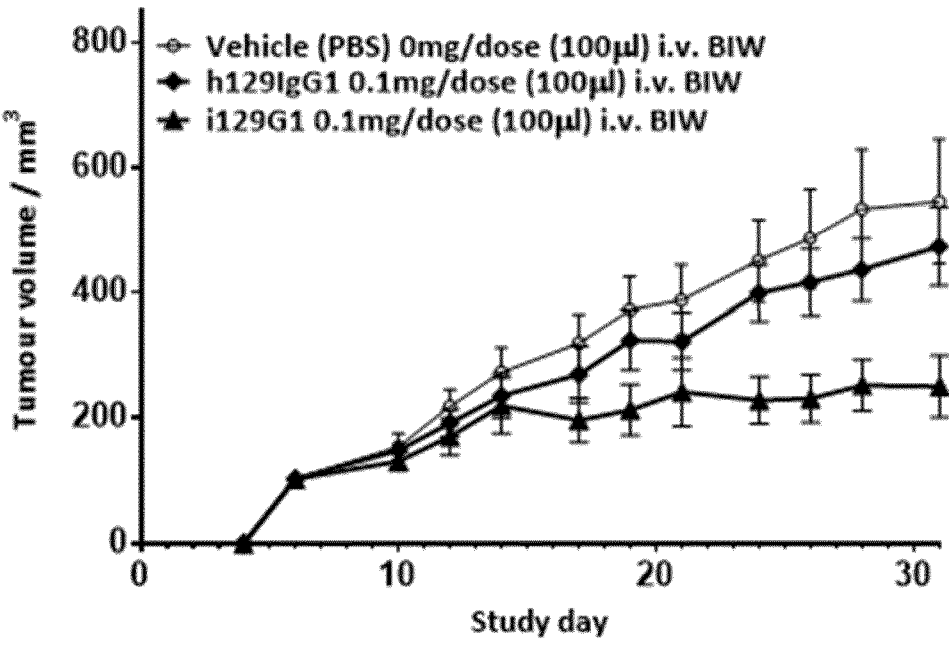
Figure 7H:
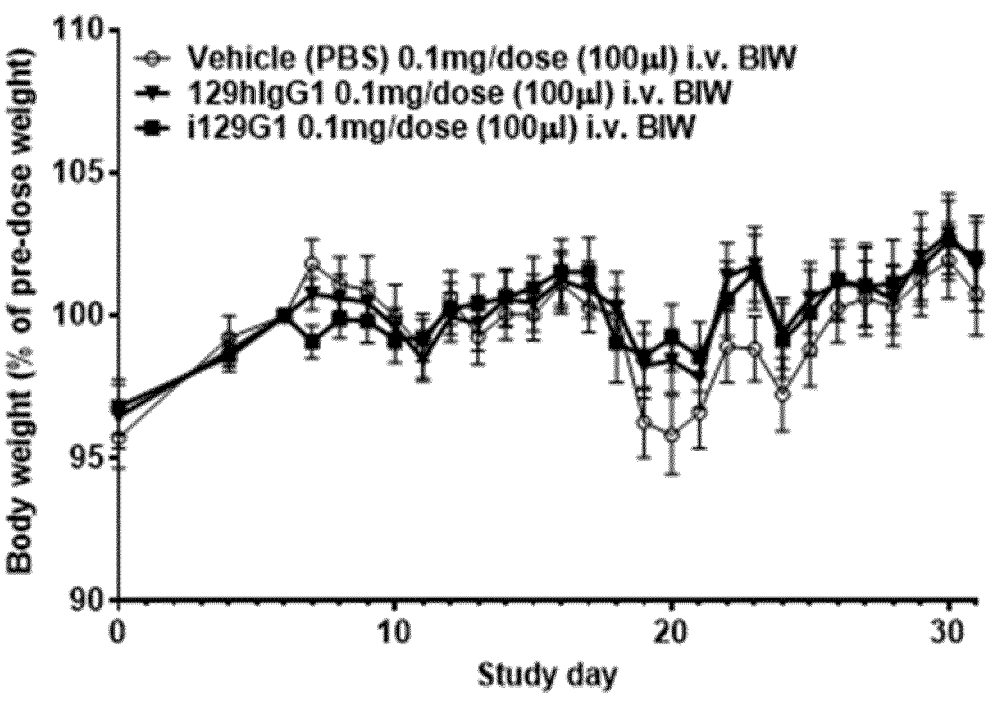

The direct cytotoxicity and improved functional affinity of i129G1 directed us towards analysing the in vivo anti-tumour activity of i129G1 in comparison with the parental 129IgG1 in a COLO205 xenograft model. The i129G1 mAb instigated a significant reduction in tumour volume compared to vehicle control (two-way ANOVA, p<0.0001) which remained significant when compared to 129IgG1, thereby corroborating the in vitro results (FIG. 7G). No effect on mean body weight was observed (FIG. 7H).

The creation of a mAb, through the introduction of a select number of mIgG3 constant region residues, with direct cytotoxicity, improved functional affinity and superior in vivo anti-tumour activity paves the way to applying our strategy to other cancer-targeting mAbs with clinical utility.

Figure 8A:
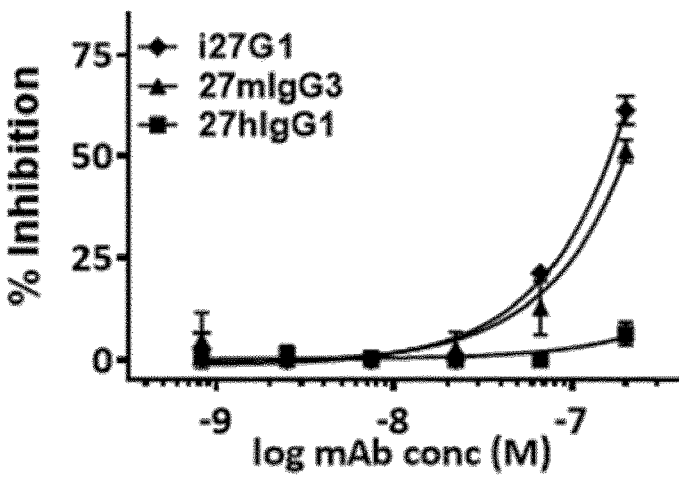
FIG. 8. i27G1 exhibits significantly improved direct cytotoxicity and functional affinity compared to 27IgG1, whilst maintaining immune effector functions Significantly increased proliferation inhibition on MCF7 (Panel A) and AGS (Panel B) by i27G1 compared to 27IgG1. Significantly increased functional affinity (SPR) by i27G1 compared to 27IgG1 (Panel C). i27G1 maintains equivalent ADCC (Panel D) as well as CDC activity (panel E) on MCF7. Significance versus parental constructs was deduced from two-way ANOVA (direct cytotoxicity) or one-way ANOVA (functional affinity) with Dunnett's corrections for multiple comparisons.
Figure 8B:
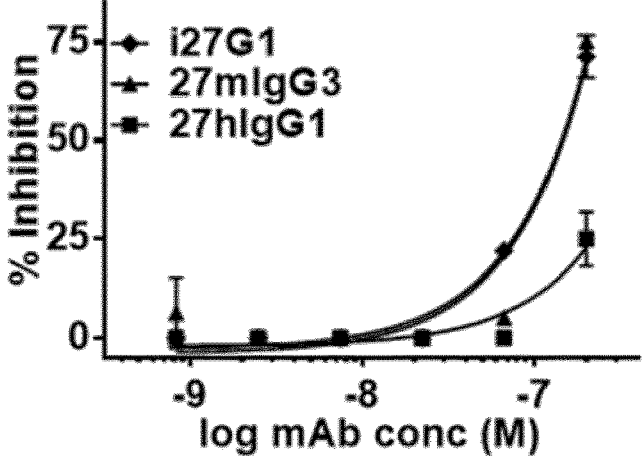
Figure 8C:
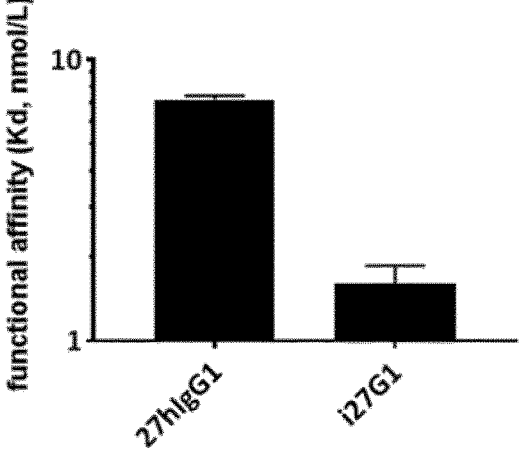
Figure 8D:
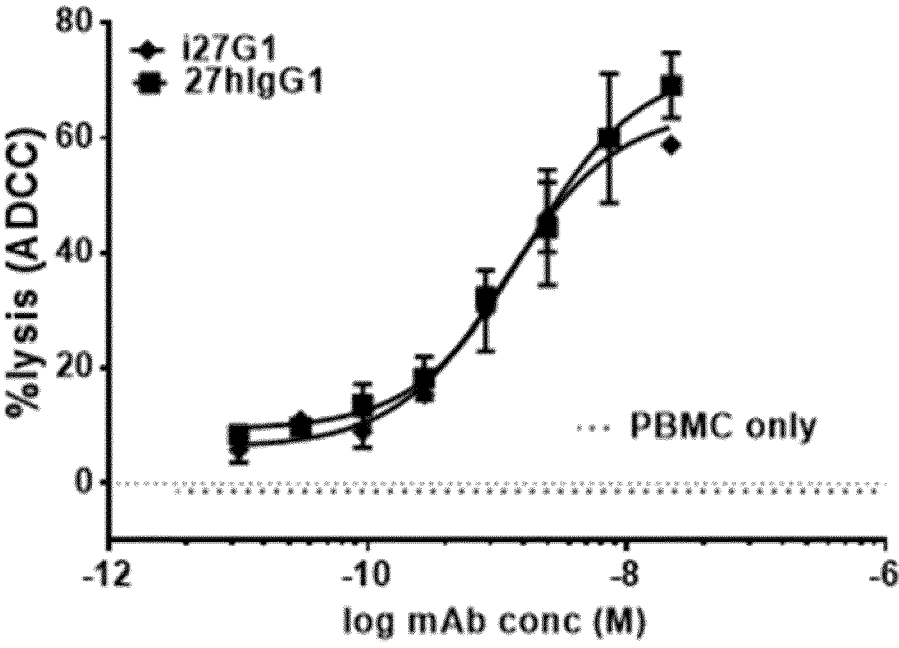
Figure 8E:
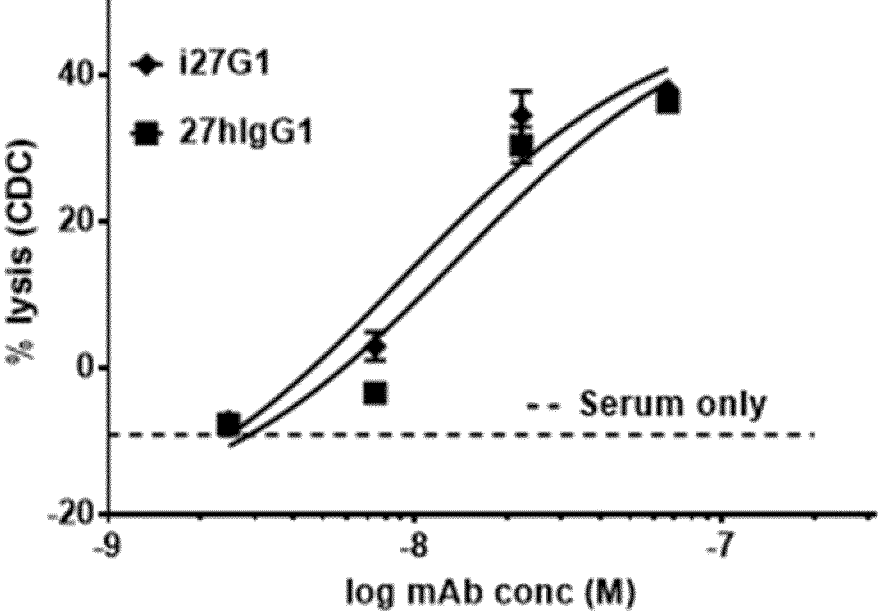

Example 6. Transfer of the 'iG1' Sequences into an Alternative, Lewis$^y$ Glycan Binding mAb (27IgG1) Creates a Cancer-Targeting mAb with Improved In Vitro Direct Cell Killing Ability We also created a mono-specific Lewis$^y$-binding mAb, 27mAb with a wide-ranging tumour tissue distribution and favourable normal human tissue binding. This mIgG3 mAb displays direct cell killing on the Lewis$^y$-expressing AGS and MCF7 cell lines, whereas the chimeric 27IgG1 did not (FIGS. 8A and B). We introduced our selected 23 mG3 residues into 27IgG1, thereby creating i27G1 and analysed its direct cell killing. On both MCF7 and AGS, the i27G1 displays significantly improved direct cell killing, compared to 27IgG1, equivalent to the 27mG3 mAb (FIGS. 8A and B). Additionally, i27G1 exhibits significantly improved functional Lewis$^y$ affinity compared to the 27IgG1 (FIG. 8C). Importantly, the effector functions of i27G1, ADCC as well as CDC, were both equivalent to those of 27IgG1, on MCF7 (FIGS. 8D and 8E).

Collectively the results indicate that transfer of selected regions from the mIgG3 constant region into the 27IgG1 backbone created a hybrid mAb with direct cell killing ability, increased functional affinity as well as robust immune effector functions.

Figure 9A:
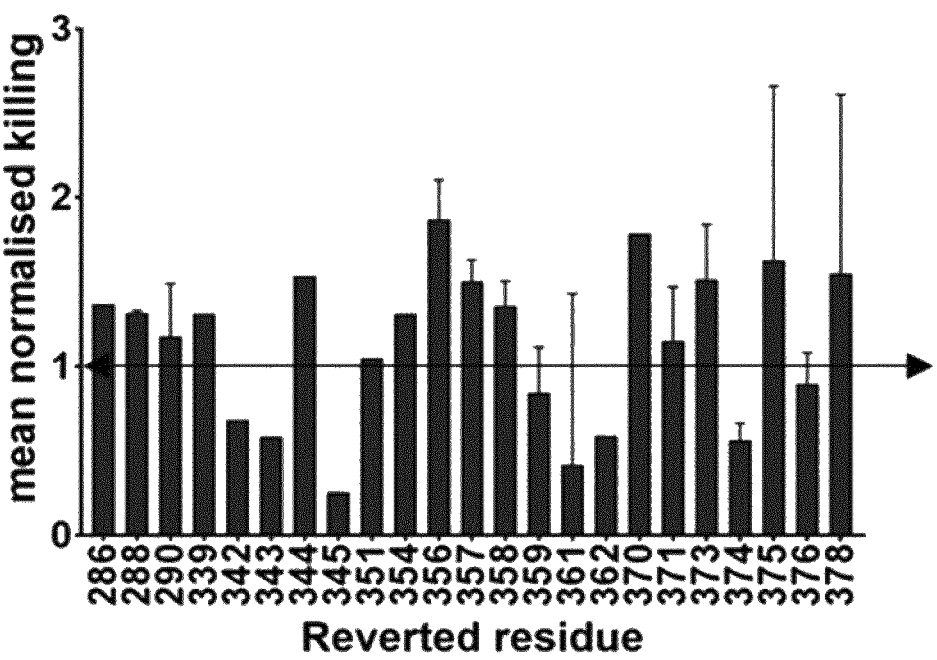
FIG. 9. Single revertant analysis reveals a minimum of 15 residues are required to maintain direct cell killing. Direct cytotoxicity of 23 single i88G1 revertants on COLO205 (Panel A) and HCT15 (Panel B). Normalised cell killing (relative to i88G1) demonstrates the need for an increased number of mG3 residues to maintain direct cytotoxicity on HCT15 (15 residues), compared to COLO205 (seven residues). Improved constructs with 15 mG3 residues (i88G1v2, panels C and E and i129G1v2, Panel D) maintain equivalent direct cytotoxicity on COLO205 and HCT15 compared to parental constructs with 23 mG3 residues, i88G1 and i129G1, respectively.
Figure 9B:
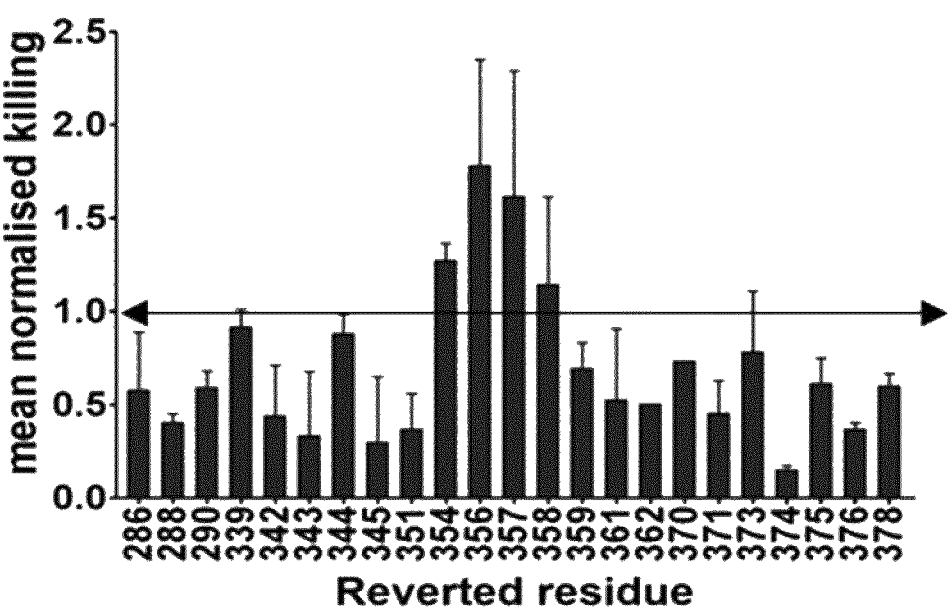
Figure 9C:
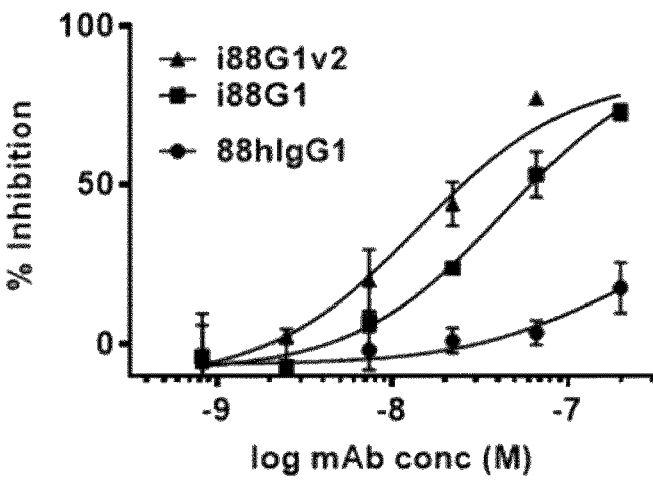
Figure 9D:
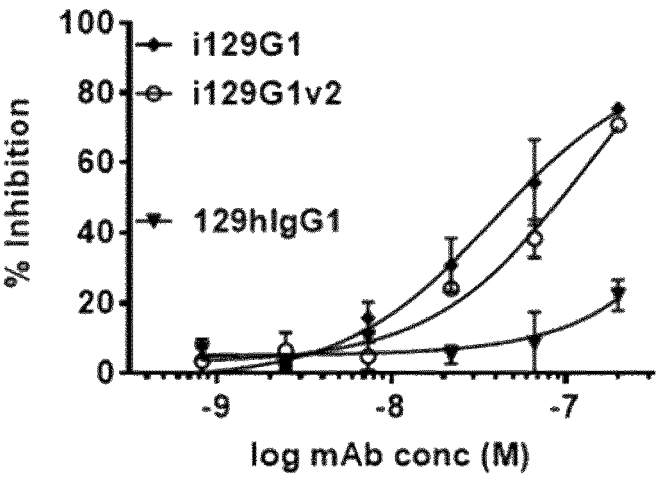
Figure 9E:
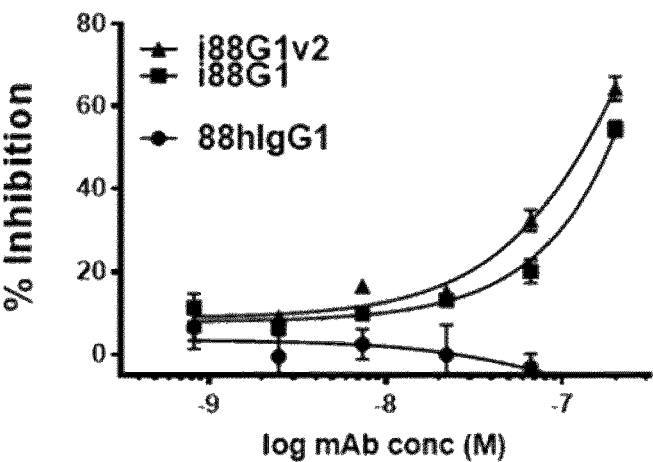

Example 7. Further Fine-Tuning of the 23 'IG1' Sequences Suggests that 15 or 7 Resides are Essential to Maintain Direct Cell Killing in a Cell-Type Dependent Manner In order to evaluate the individual contribution of each of the 23 selected mG3 residues, a single revertant strategy based on i88G1 (Example 4) was performed. Each of the 23 mG3 residues in i88G1, singly, were reverted to the hG1 residue and the resulting construct was analysed for direct cell killing on COLO205 as well as HCT15, using the cellular proliferation assay (CCK-8, Sigma 96992) and compared to the parental i88G1. The fixed concentration percentage killing was normalised against the corresponding percentage killing by i88G1 at the same concentration, in the same experiment, in order to relate cell killing across multiple experiments. Most i88G1 revertant constructs retained good direct cell killing against COLO205 cells (FIG. 9A). Residues 342, 343, 345, 361, 362, 374 and 376 (seven in total) had a mean normalised killing less than 1 and were considered essential for the direct cell killing on the high-binding COLO205 cell line. In contrast if these seven residues alone were reverted this minimal construct did not express/fold and therefore this construct has not been pursued. Direct cell killing of the moderate-binding HCT15 proved to be more sensitive to reversal back to hG1 residues, with only eight reverted residues (339, 344, 354, 356, 357, 358, 370, 373) maintaining cell killing to within one standard deviation of 188G1, thus necessitating the retention of 15 mG3 residues: N286T, K288W, K290Q, Q342R, P343A, E345T, L351I, T359S, N361K, Q362K, G371N, P374S, S375E, D376A, A378S (FIG. 9B). The latter construct was created for both the 88 and 129mAbs, i88G1v2 and i129G1v2, respectively and their cell killing analysed on COLO205 and HCT15. Direct cell killing of COLO205 by 188G1v2 as well as i129G1v2 was equivalent to that observed by i88G1 and i129G1, respectively (FIGS. 9C and 9D). Direct cell killing of HCT15 by i88G1v2, equally, matched that observed by i88G1 (FIG. 9E).

Collectively, the results suggest that 15 mG3 residues: N286T, K288W, K290Q, Q342R, P343A, E345T, L351I, T359S, N361K, Q362K, G371N, P374S, S375E, D376A, A378S, suffice to induce direct cell killing on high as well as moderate-binding cancer cell lines.

TABLE 1

Overview of the kinetic binding parameters of the parental 88 mAbs
Real-time Lewis$^a$-HSA binding$^{a,b}$

| mAb | Association Rate $k_{on}$ (1/mols/L) | Dissociation Rate $k_{off}$ (1/s) | Dissociation Constant $K_d$ (nmol/L) |
|---|---|---|---|
| FG88 | $7.0 \times 10^4$ | $3.6 \times 10^{-6}$ | 0.05 |
| 88mIgG3 | $5.2 \times 10^5$ | $1.8 \times 10^{-4}$ | 0.3 |
| 88IgG1 | $3.1 \times 10^5$ | $1.5 \times 10^{-2}$ | 48.3 |

$^a$representative of a minimum of 3 analyses
$^b$results for high-density surface binding are presented

TABLE 2

Overview of the functional characteristics of the improved constructs
Biological activity characteristics

| mAb | functional affinity $K_d$ (nmol/L) | direct cytotoxicity$^a$ EC$_{50}$ (nmol/L) | ADCC EC$_{50}$ (nmol/L) | CDC EC$_{50}$ (nmol/L) | Pore forming ability |
|---|---|---|---|---|---|
| 88mIgG3 | 0.3 | 26.7 | ND | ND | +++ |
| 88IgG1 | 48.3 | N/A | 0.13 | 3.9 | – |
| i88G1 | 0.5 | 29.4 | 0.35 | 0.1 | ++ |
| 129IgG1 | 2.5 | N/A | 1.7 | 75.3 | – |
| i129G1 | 0.005 | 45.6 | 2.4 | 8.2 | ++ |

$^a$deduced from proliferation inhibition on COLO205
N/A: not appropriate, ND: not determined

Example 8. Generation and Initial Characterisation of FG27 mAbs: FG27 was Raised by Immunisation with Gastric Tumour Cell Glycolipid Analysis of antibody response to immunisations: Antibody titres were initially monitored by lipid enzyme-linked immunosorbent assay (ELISA). Thin layer chromatography (TLC) analysis using ST16 total and plasma membrane lipid extracts, flow cytometry analysis (FACS) using ST16 tumour cells and Western blot using ST16 whole cell extract, total and plasma membrane lipid extracts were subsequently performed. The mouse considered to have the best response, compared to the pre-bleed serum control was boosted intravenously (i.v.) with ST16 plasma membrane lipid extract prior to fusion.

Figures 9F, 10:
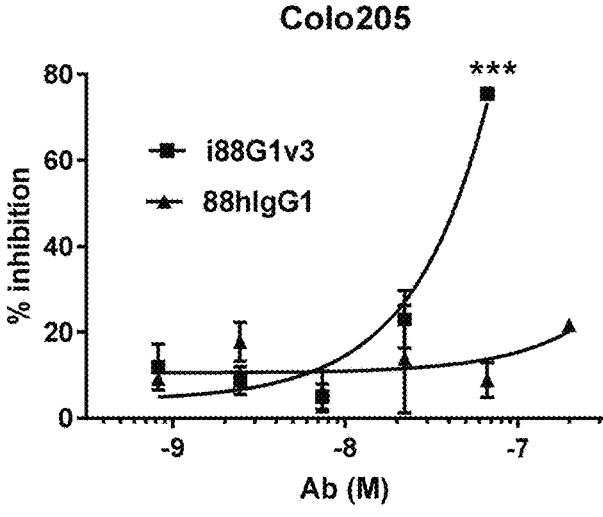
FIG. 10. Binding of FG27.10 and FG27.18 to ST16, HUVEC and PBMCs. The negative control for this assay was NSO supernatant for ST16 and HUVEC, or cell alone for the PBMCs and the positive control was either the anti-sialyl-di Lewis$^a$ mAb, 505/4, or W6/32 which recognises HLA.
Figure 11:
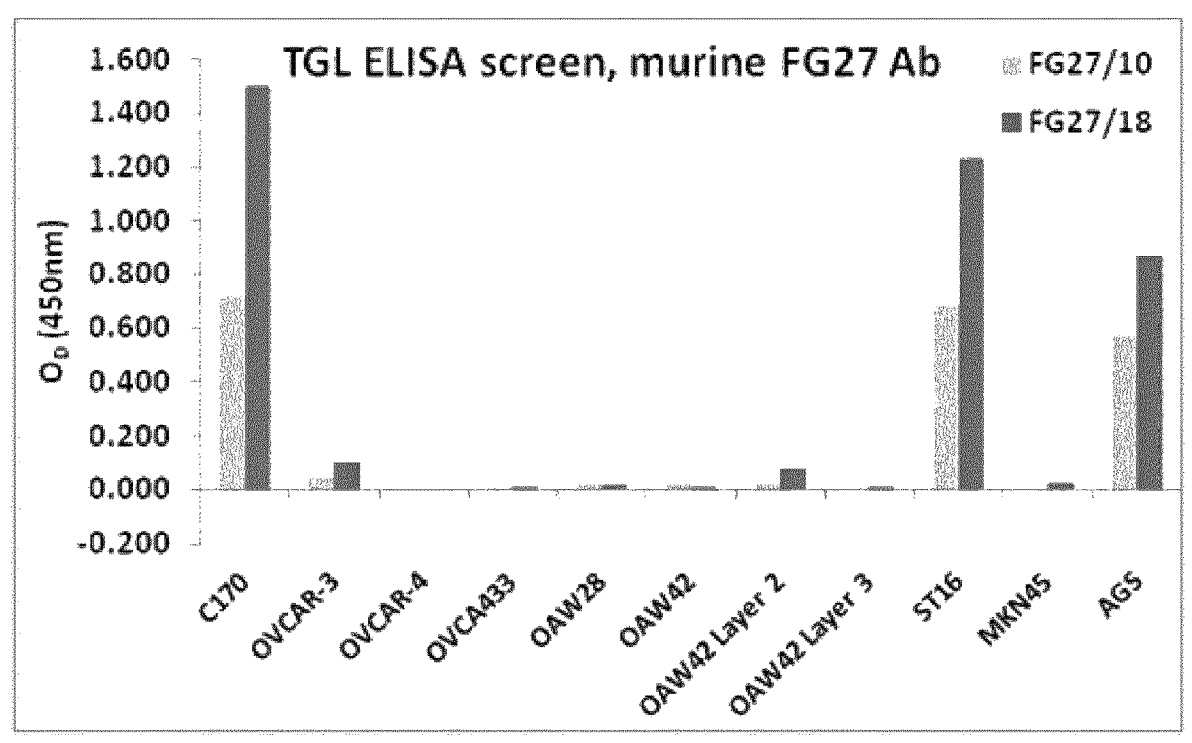
FIG. 11. Binding of FG27.10 and FG27.18 to glycolipid extracts from colorectal (C170), ovarian (OVCAR-3, OVCAR-4, OVCA433, OAW28, OAW42) and gastric cell lines (ST16, MKN45, AGS). Glycolipid extracted from a range of cancer cell lines was plated on ELISA plates. Cells and glycolipid were then incubated with FG27.10 or FG27.18 supernatant. Binding to glycolipid was probed with anti-IgG-HRP/TMB.

Binding of FG27 hybridoma supernatant to a panel of tumour cell lines was analysed by direct immunofluorescence and FACS analysis. Both FG27.10 and FG27.18 bound ST16 but did not bind human umbilical vein endothelial cells (HUVECs) or peripheral blood mononuclear cells PBMCs when compared to positive control anti-HLA mAb, W6/32 (eBioscience, CA, USA), and the negative control (FIG. 10). FG27.10 and FG27.18 were both cloned. FG27.10 was an IgG3K and FG27.18 was an IgG1K subclass. To ensure that both mAbs bound to glycolipid, glycolipid was extracted from a range of cell lines, dried onto an ELISA plate before incubating with FG27.10 and FG27.18. Binding was seen with C170, ST16 and AGS derived glycolipid with both mAbs but not cell lines which showed a lack of binding to whole cells (MKN-45, OAW28, OVCAR-3, OVCAR-4 and OAW42; FIG. 11).

Example 9. Direct Cell Killing of Parental FG27 mAb

A number of anti-glycan mAbs have been shown to induce direct cell death in antigen positive cell lines with no need for effector cells or complement. This can potentially enhance their in vivo efficacy as tumours can develop mechanisms to avoid immune-mediated cell death. This capability is mainly associated with glycan-binding mAbs of the mIgG3 isotype, hence the property is lost upon chimerisation or humanisation.

Figure 12A:
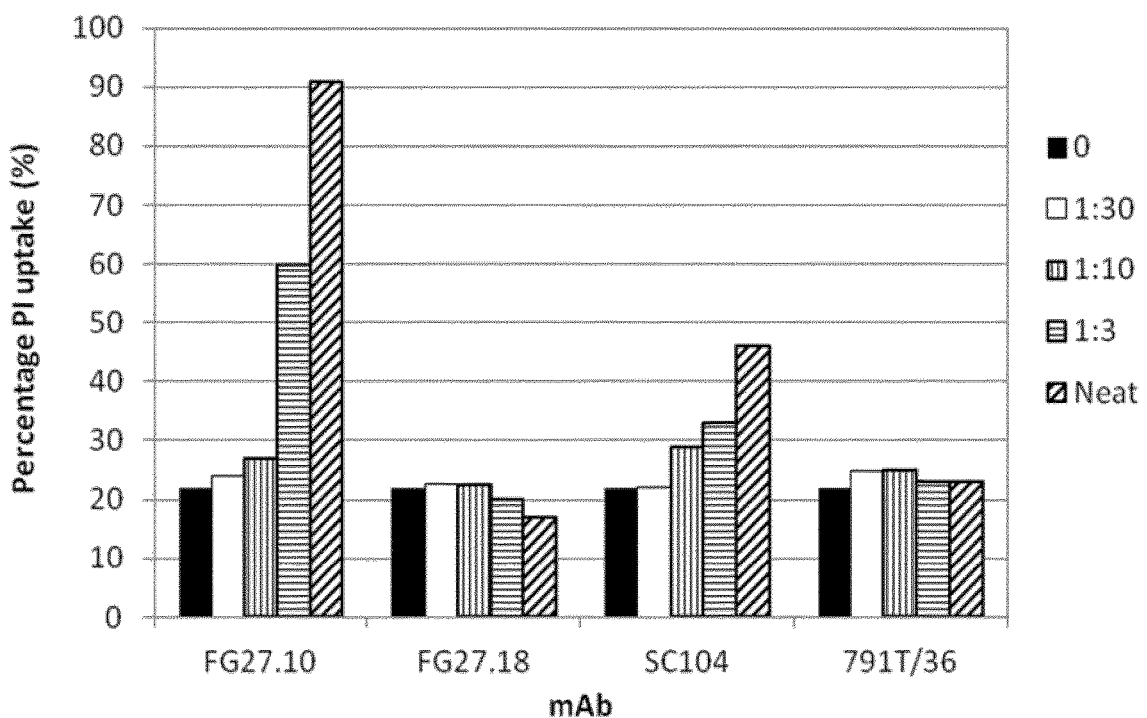
FIG. 12A. PI uptake of ST16 cells mediated by the mouse IgG3 mAb FG27.10 induced potent uptake of PI even at 4° C. but the IgG1 variant FG27.18 did not.
Figure 12B:
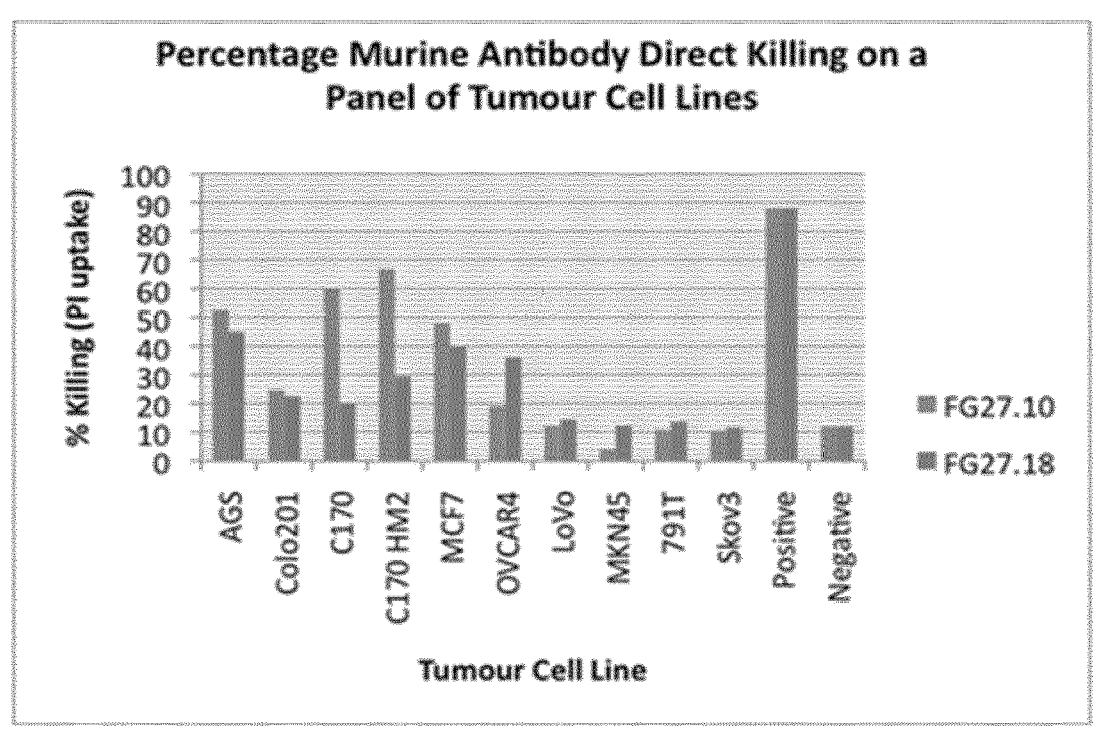
FIG. 12B: PI uptake mediated by FG27.10 and FG27.18 on a panel of tumour cell lines (AGS, Colo201, C170, C170HM2, MCF7, OVCA4, LoVo, MKN45, 791T and Skov3).

In order to determine whether FG27.10 and FG27.18 have the ability to cause direct cell death, ST16 cells were incubated with FG27.10, FG27.18 and the anti-sialyl Lewis$^a$ mAb SC104 for 2 hrs at RT, before cell death was measured by the uptake of PI, which is a DNA intercalating agent that is only taken up by dying cells (FIG. 12A). Interestingly, despite having the same variable region, only FG27.10 was able to induce direct cell death, with no uptake of PI observed with FG27.18. FIG. 12B shows direct cell killing of a range of antigen positive (AGS, Colo201, C170, C170HM, MCF-7, OVCAR4) cell lines with the two mAbs showing variable amounts of killing. Neither mAb showed killing of the antigen negative cell lines (LoVo, MKN45, 791T, SKOV3).

Figure 12C:
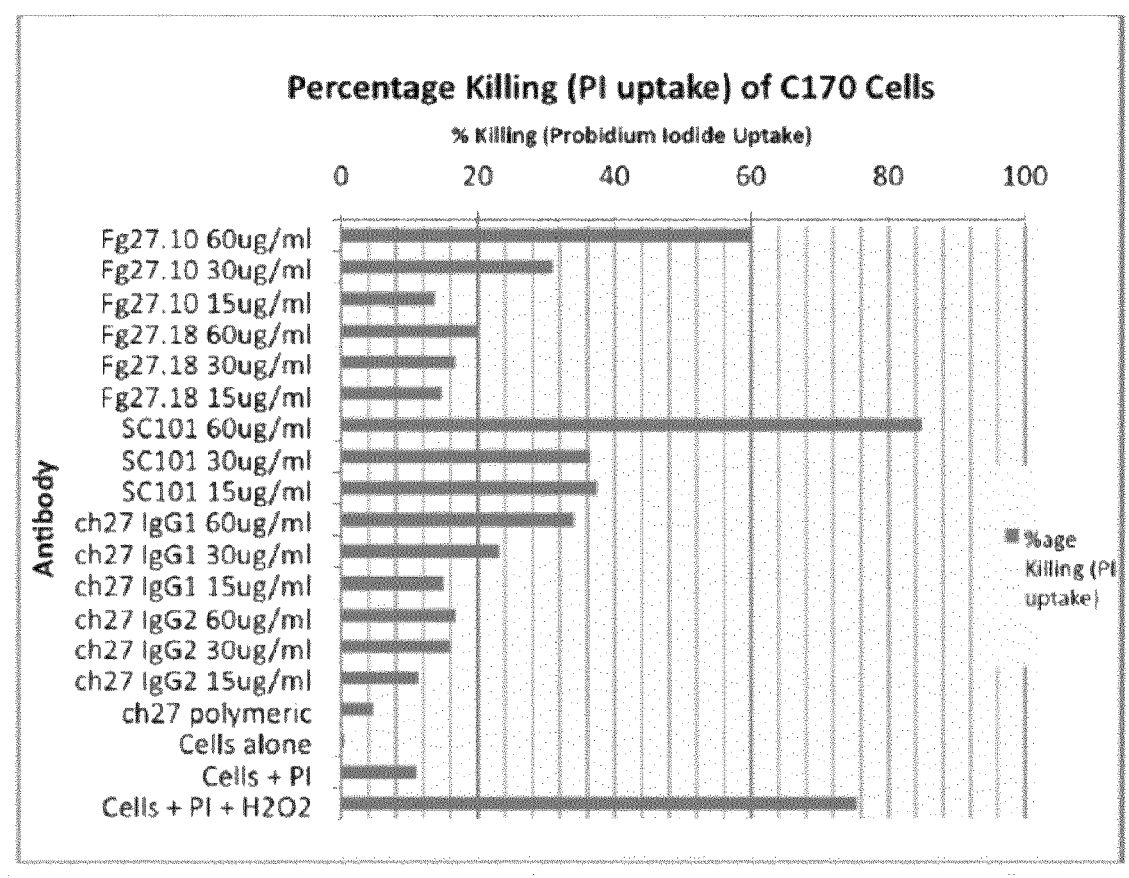
FIG. 12C: PI uptake mediated by FG27.10, FG27.18, CH27 IgG2, CH27 IgG1 on C170 cells.

FIG. 12C shows PI uptake in the colorectal cell line C170 by a range of mAbs. FG27.10 and the positive control antibody SC101 showed strong titratable killing. FG27.18 showed weak non titratable killing. The modified IgG1 chimeric showed moderate titratable killing whereas the IgG2 variant did not.

Example 10. FG27 Binding Studies

Figure 13A:
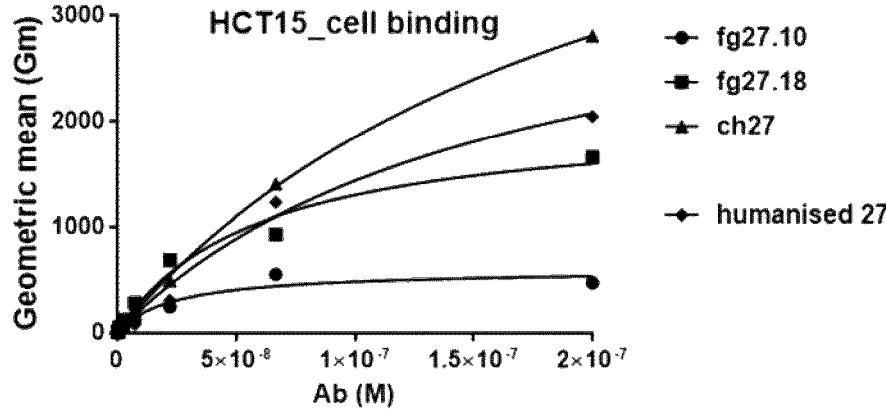
FIG. 13A, HCT15.
Figure 13B:
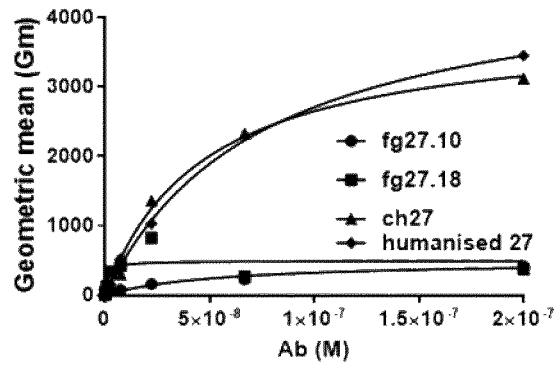
FIG. 13B, AGS.
Figure 13C:
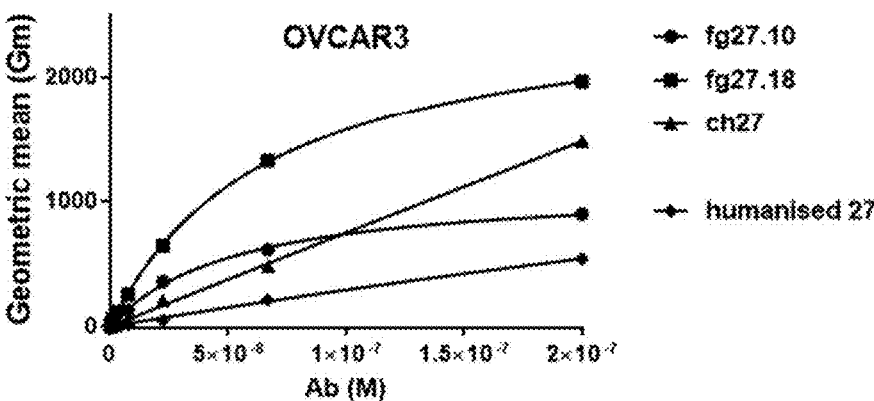
FIG. 13C, OVCAR3.
Figure 13D:
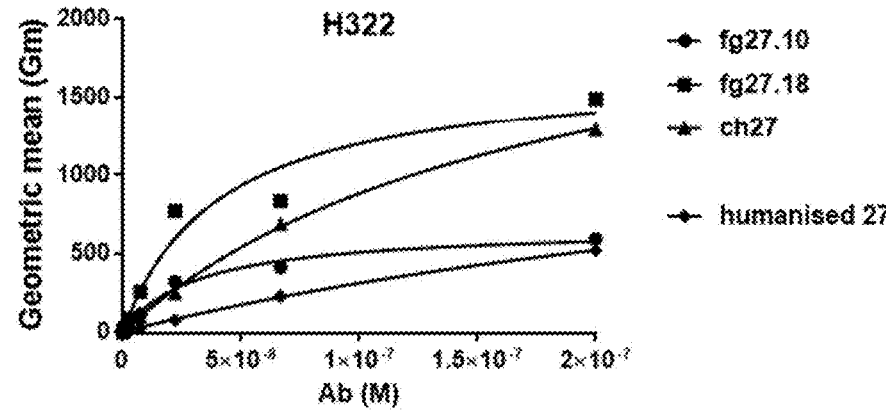
FIG. 13D, H322, and FIG. 13E, MCF7, and SPR analysis for FG27.10 (FIG. 13F) and FG27.18 (FIG. 13G).
Figure 13E:
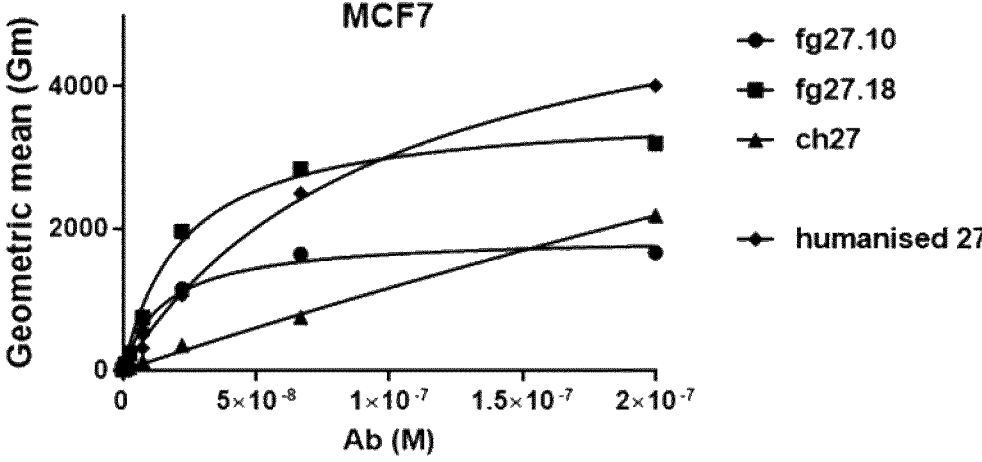
FIG. 13. Binding of FG27.10, FG27.18, ch27IgG1 and the humanised variant hLewAC to a panel of cell lines.
Figure 13F:
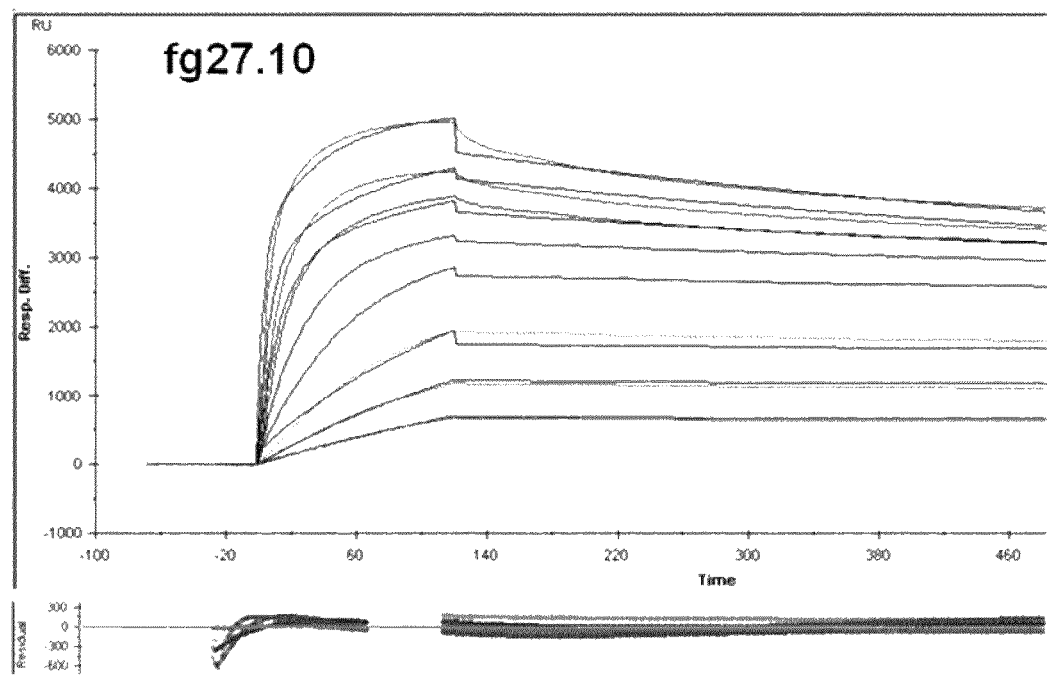
Figure 13G:
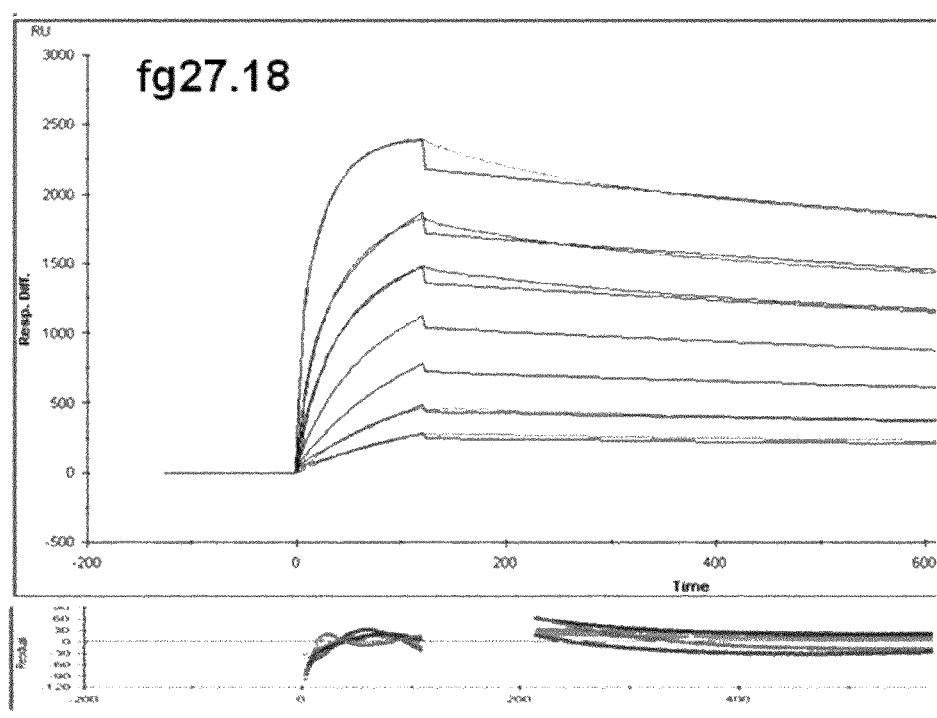

The humanised (humanized 27) and chimeric mAbs (CH27) demonstrated a similar cell binding pattern on titration on cancer cell lines (FIG. 13A-E). Equilibrium affinity constants are overall on the same order, but slightly higher compared to the parental murine antibodies (FIG. 13F-G), whereas the maximum binding capacity of the humanised 27 and CH27 are larger compared to those of the murine mAbs. This result suggests a successful outcome of the humanization process.

Example 11. Direct Cell Killing of the Humanised FG27 mAb

In order to enhance the direct cell killing of the human IgG1 27 chimeric (271gG1), we transferred selected mIgG3 constant region residues into the IgG1 Fc domain thereby creating an improved 'i27G1' LewisY glycan binding mAb with improved in vitro direct cell killing ability.

Figure 14:
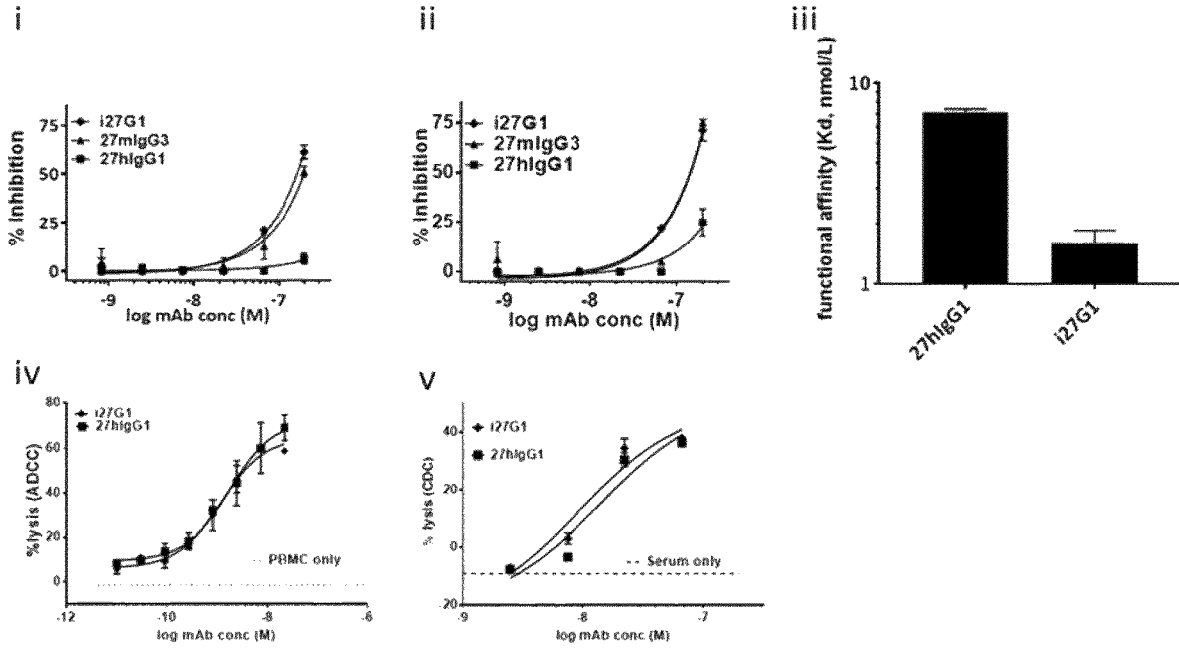
FIG. 14. i27G1 exhibits significantly improved direct cytotoxicity and functional affinity compared to 27IgG1, whilst maintaining immune effector functions. Significantly increased proliferation inhibition on MCF7 (Panel i) and AGS (Panel ii) by i27G1 compared to 27IgG1. Significantly increased functional affinity (SPR) by i27G1 compared to 27IgG1 (Panel iii). i27G1 maintains equivalent ADCC (Panel iv) as well as CDC activity (panel v) on MCF7. Significance versus parental constructs was deduced from two-way ANOVA (direct cytotoxicity) or one-way ANOVA (functional affinity) with Dunnett's corrections for multiple comparisons.

FIG. 14 shows direct cell killing, functional affinity as well as effector functions of the improved i27G1. The mIgG3 27 antibody has direct cell killing ability on the Lewis^y-expressing MCF7 (FIG. 14*i*) and AGS cell lines (FIG. 14*ii*) whereas the chimeric 27IgG1 does not. Our i27G1, containing selected mIgG3 constant region residues, displays significantly improved direct cell killing, compared to 27IgG1, equivalent to the 27mG3 mAb, on both MCF7 (FIG. 14*i*) and AGS (FIG. 14*ii*).

Additionally, i27G1 exhibits significantly improved functional Lewis^y affinity compared to the 27IgG1 (FIG. 14*iii*). Importantly, the effector functions of i27G1, ADCC as well as CDC, were both equivalent to those of 271gG1, on MCF7 (FIG. 14*iv* and 14v). Collectively the results indicate that transfer of selected regions from the mIgG3 constant region into the 27IgG1 backbone created a hybrid mAb with direct cell killing ability, increased functional affinity as well as robust immune effector functions.

Figure 18A:
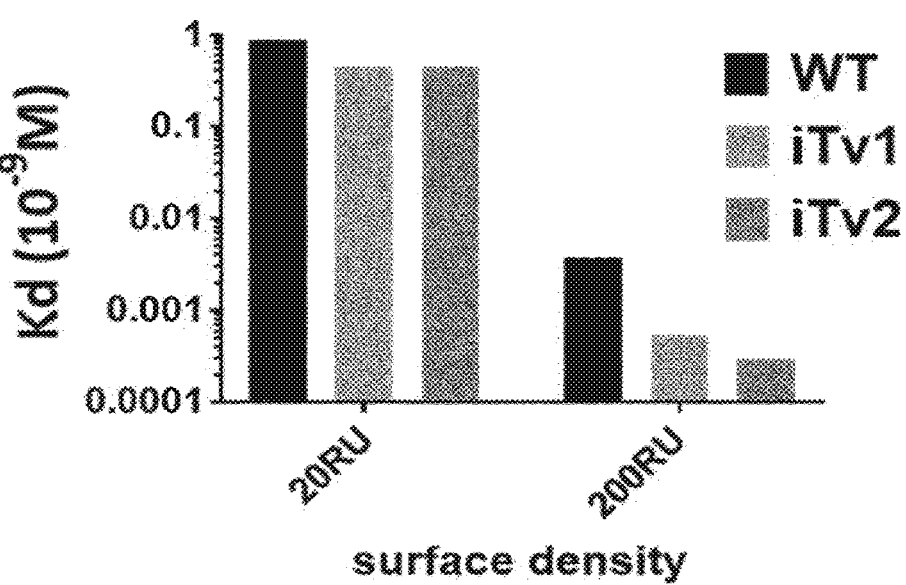
FIG. 18. iTrastuzumab (iTv1 and iTv2) exhibit improved functional affinity compared to wild-type Trastuzumab (WT) in a ligand density-dependent manner (Biacore® T200 analysis, Panel A). Cell binding overview of Trastuzumab constructs on a range of high-binding (SKBR3, BT474) and low-to-moderate binding cell lines (MDA-MB231 and SKOV3) (Panel B). Significantly improved direct cytotoxicity (iTv2) on MDA-MB231 compared to wild-type Trastuzumab (Panel C). Enhanced PI uptake on BT474 cells (reflecting membrane damage) by iTv1 and iTv2 (highest concentration) compared to wild-type Trastuzumab (Panel D). Improved solid-phase Her2 binding by directly labelled iTv2 compared to wild-type trastuzumab (Panel E). Significance versus parental constructs was deduced from two-way ANOVA (direct cytotoxicity) with Dunnett's corrections for multiple comparisons.
Figure 18B:
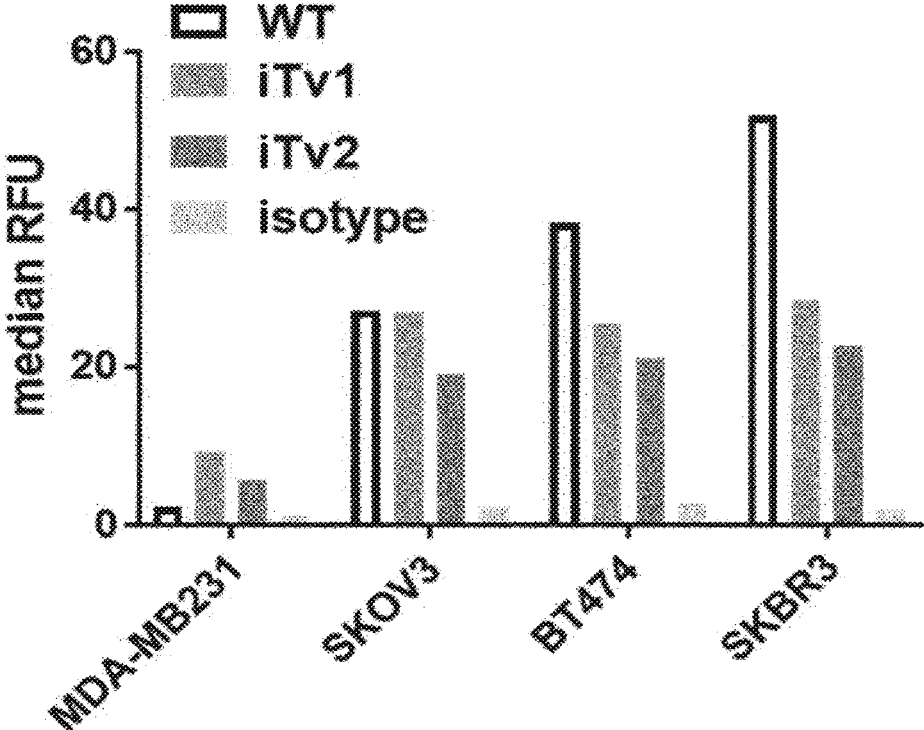
Figure 18C:
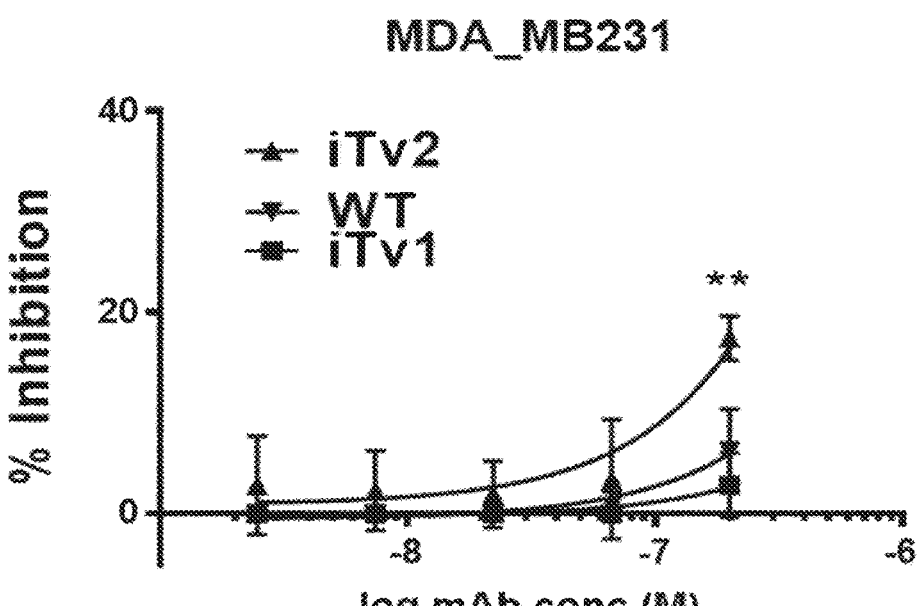
Figure 18D:
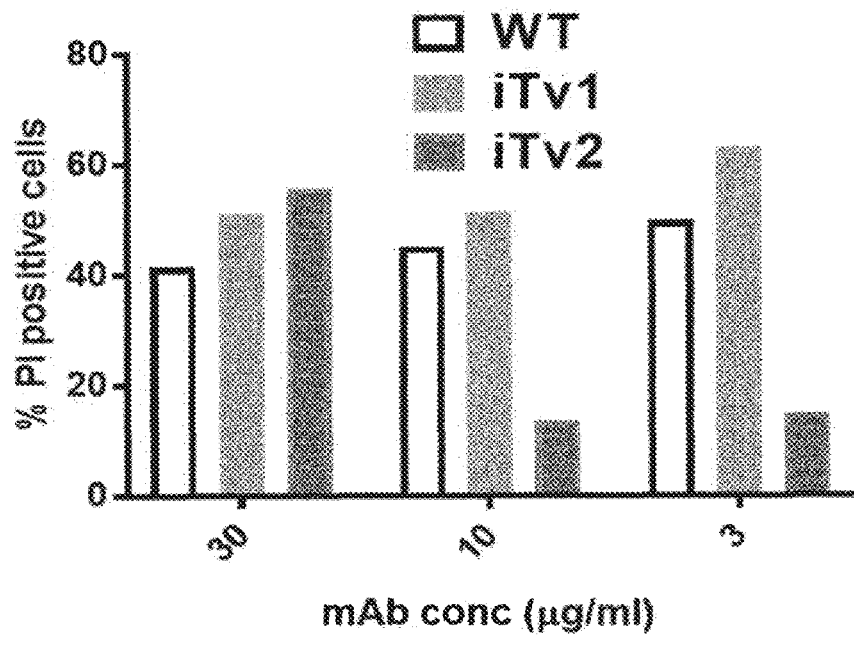

Example 12. Transfer of the 'iG1' Sequences into a Protein Binding mAb (Trastuzumab) Creates a Cancer-Targeted mAb with Improved Functional Affinity In order to evaluate if altering the amino acid residues of an antibody targeting cancer-associated proteins resulted in increased functional affinity, the 'iG1' residues (23, 'vi' as well as 15, 'v2') were altered and the affinity of the resultant, 'improved' antibody variants determined via SPR analysis. To determine the functional affinity, the three Trastuzumab antibody constructs were titrated across HER2-coated chips at three different ligand densities. Multicycle kinetic analysis (in the concentration range of 90 nM-0.37M) was performed and demonstrated increased functional affinity by iTv1 and iTv2 compared to WT on both the low density (20RU) and high density (200RU) surfaces (FIG. 18A). The improvement was more pronounced on the high-density surface and was driven predominantly by a reduction in off-rate ($8.5\times10^{-8}$ 1/s for iTV1 and $7.4\times10^{-8}$ 1/s for iTv2 versus $6.0\times10^{-7}$ 1/s for WT). HEK293-expressed wild-type Trastuzumab (WT) and the 'improved' variants (iTv1 and iTv2) gave high binding to the HER2 expressing cell lines SKBR3 and BT474, and low to moderate binding to MDA-MB231 and SKOV3 (FIG. 18B). In order to evaluate whether the more avid binding by iTv1 and iTv2 would result in differential cytotoxicity, proliferation inhibition on MDA-MB231 and PI uptake on BT474 were explored. iTv2 displayed significantly improved proliferation inhibition compared to WT on MDA-MB231 (FIG. 18C), with both iTv1 and iTv2 showing improved PI uptake on BT474 cells compared to WT, most pronounced at the highest concentration tested (FIG. 18D). Titration of directly HRPO-labelled mAbs onto HER2 coated ELISA plates revealed improved binding by iTv2 versus WT. Collectively the results indicate improved functional affinity by the 'iG1' engineered Trastuzumab constructs suggesting that our approach can also benefit protein-targeting mAbs, in addition to glycan targets. The final outcome of our engineering approach however, relies on the interplay between the intricate avidity of the mAb combined with the target density.

EMBODIMENTS

Certain embodiments of the present invention are described below. Various features of the following embodiments may be combined with features of other embodiments, for example structural features such as sequence motifs may be combined with functional features of the claimed antibodies or antigen binding fragments thereof.

1. A modified IgG1 antibody or antigen-binding fragment thereof comprising one or more residues of an Fc-region of an immunoglobulin and a binding region, wherein one or more residues of the Fc-region are modified to the corresponding residue from a mouse IgG3 antibody and wherein the modified IgG1 antibody or antigen-binding fragment thereof has enhanced functional affinity when compared to a corresponding IgG1 antibody or antigen-binding fragment thereof comprising wildtype Fc-region residues.

2. The modified IgG1 antibody or antigen-binding fragment thereof according to embodiment 1 wherein the functional affinity of the modified IgG1 antibody or antigen-binding fragment thereof is enhanced by at least about 10% when compared to a corresponding IgG1 antibody or antigen-binding fragment thereof comprising wildtype Fc-region residues.

3. The modified IgG1 antibody or antigen-binding fragment thereof according to embodiment 1 or embodiment 2 wherein the functional affinity of the modified IgG1 antibody or antigen-binding fragment thereof is enhanced by at least about 20%, at least about 30%, at least about 40%, at least about 50%, at least about 60%, at least about 70%, at least about 80%, at least about 90% or at least about 100% when compared to a corresponding IgG1 antibody or antigen-binding fragment thereof comprising wildtype Fc-region residues.

4. The modified IgG1 antibody or antigen-binding fragment thereof according to any one of embodiments 1 to 3, wherein the modified IgG1 antibody or antigen-binding fragment thereof has enhanced direct cell-killing when compared to a corresponding IgG1 antibody or antigen-binding fragment thereof comprising wildtype Fc-region residues.

5. The modified IgG1 antibody or antigen-binding fragment thereof according to embodiment 4 wherein the direct cell-killing of the modified IgG1 antibody or antigen-binding fragment thereof is enhanced by at least about 10% when compared to a corresponding IgG1 antibody or antigen-binding fragment thereof comprising wildtype Fc-region residues.

6. The modified IgG1 antibody or antigen-binding fragment thereof according to embodiment 1 or embodiment 2 wherein the direct cell-killing of the modified IgG1 antibody or antigen-binding fragment thereof is enhanced by at least about 20%, at least about 30%, at least about 40%, at least about 50%, at least about 60%, at least about 70%, at least about 80%, at least about 90% or at least about 100% when compared to a corresponding IgG1 antibody or antigen-binding fragment thereof comprising wildtype Fc-region residues.

7. The modified IgG1 antibody or antigen-binding fragment thereof according to any preceding embodiment, wherein the one or more residues of the Fc-region are selected from: Q342, P343, E345, N361, Q362, P374, D376.

8. The modified IgG1 antibody or antigen-binding fragment thereof according to any preceding embodiment, wherein the one or more modified residues of the Fc-region are selected from: Q342R, P343A, E345T, N361K, Q362K, P374S, D376A.

9. The modified IgG1 antibody or antigen-binding fragment thereof according to any preceding embodiment, wherein the one or more residues of the Fc-region are selected from: N286, K288, K290, Q342, P343, E345, L351, T359, N361, Q362, G371, P374, S375, D376, A378.

10. The modified IgG1 antibody or antigen-binding fragment thereof according to any preceding embodiment, wherein the one or more modified residues of the Fc-region are selected from: N286T, K288W, K290Q, Q342R, P343A, E345T, L351I, T359S, N361K, Q362K, G371N, P374S, S375E, D376A, A378S.

11. The modified IgG1 antibody or antigen-binding fragment thereof according to any preceding embodiment, wherein the one or more residues of the Fc-region are selected from: N286, K288, K290, A339, Q342, P343, R344, E345, L351, S354, D356, E357, L358, T359, N361, Q362, K370, G371, Y373, P374, S375, D376, A378.

12. The modified IgG1 antibody or antigen-binding fragment thereof according to any preceding embodiment, wherein the one or more modified residues of the Fc-region are selected from: N286T, K288W, K290Q, A339P, Q342R, P343A, R344Q, E345T, L351I, S354P, D356E, E357Q, L358M, T359S, N361K, Q362K, K370T, G371N, Y373F, P374S, S375E, D376A, A378S.

13. The modified IgG1 antibody or antigen-binding fragment thereof according to any preceding embodiment, wherein the one or more residues of the Fc-region are selected from: N286, K288, K290, E294, Y300, V305, A339, Q342, P343, R344, E345, L351, S354, D356, E357, L358, T359, N361, Q362, K370, G371, Y373, P374, S375, D376, A378.

14. The modified IgG1 antibody or antigen-binding fragment thereof according to any preceding embodiment, wherein the one or more modified residues of the Fc-region are selected from: N286T, K288W, K290Q, E294A, Y300F, V305A, A339P, Q342R, P343A, R344Q, E345T, L351I, S354P, D356E, E357Q, L358M, T359S, N361K, Q362K, K370T, G371N, Y373F, P374S, S375E, D376A, A378S.

15. The modified IgG1 antibody or antigen-binding fragment thereof according to any preceding embodiment, wherein the antibody or antigen-binding fragment thereof is a human antibody, humanised antibody or chimeric antibody.

16. The modified IgG1 antibody or antigen-binding fragment thereof according to any preceding embodiment, wherein the IgG1 antibody or antigen-binding fragment thereof is a monospecific antibody, bispecific antibody or multispecific antibody.

17. The modified IgG1 antibody or antigen-binding fragment thereof according to embodiment 16, wherein the IgG1 antibody or antigen-binding fragment thereof is a bispecific antibody comprising an Fc-region with a first heavy chain and a first antigen-binding region, a second heavy chain and a second antigen-binding region.

18. The modified IgG1 antibody or antigen-binding fragment thereof according to embodiment 16 or 17, wherein the IgG1 antibody or antigen-binding fragment thereof is a bispecific antibody that binds to a CD3 antigen.

19. A modified IgG1 antibody or antigen-binding fragment thereof comprising the motif RAXTXXXXXXXXXXXXXXKKXXXXXXXXXXXS XA, wherein X is any amino acid.

20. A modified IgG1 antibody or antigen-binding fragment thereof comprising the motif TXWXQXXXXXXXXXXXXXXXXXXXXXXXXXXX XXXXXXXXXXXXXXXXXXXXXXXXXRAXTXXXXX IXXXXXXXSXKKXXXXXXXXXNXXSEAXS, wherein X is any amino acid.

21. A modified IgG1 antibody or antigen-binding fragment thereof comprising the motif TXWXQXXXXXXXXXXXXXAXXXXXXXXXXX XXXXXXXXXXXXXXXXXXXXPXXRAQTXXXX XIXXPXEQMSXKKXXXXXXXTXXFSEAXS, wherein X is any amino acid.

22. A modified IgG1 antibody or antigen-binding fragment thereof comprising the motif TXWXQXXXAXXXXXFXXXXAXXXXXXXXXXX XXXXXXXXXXXXXXXXXXXXPXXRAQTXXXX XIXXPXEQMSXKKXXXXXXXTNXFSEAXS, wherein X is any amino acid.

23. A modified IgG1 antibody or antigen-binding fragment thereof comprising any one or more motifs selected from the following list:
   (i) TXWXQ
   (ii) RAXTXXXXXI
   (iii) SXKKXXXXXXXXXNXXSEAXS
   (iv) NXXSEAXS
   wherein X is any amino acid.

24. A method of increasing the direct cell killing ability of an IgG1 antibody or antigen-binding fragment thereof comprising one or more residues of an Fc-region of an immunoglobulin and a binding region, wherein the method comprises replacing one or more residues of the CH2 and/or the CH3 domains of said Fc-region with one or more corresponding residues from mouse IgG3 CH2 and/or CH3 domains.

25. The method of increasing the direct cell killing ability of an IgG1 antibody or antigen-binding fragment thereof according to embodiment 24 wherein the method comprises modifying one or more residues of the Fc region selected from: Q342, P343, E345, N361, Q362, P374, D376.

26. The method according to embodiment 25 wherein the one or more modified residues are selected from: Q342R, P343A, E345T, N361K, Q362K, P374S, D376A.

27. The method of increasing the direct cell killing ability of an IgG1 antibody or antigen-binding fragment thereof according to embodiment 24 wherein the method comprises modifying one or more residues of the Fc region selected from: N286, K288, K290, Q342, P343, E345, L351, T359, N361, Q362, G371, P374, S375, D376, A378.

28. The method according to embodiment 27 wherein the one or more modified residues are selected from: N286T, K288W, K290Q, Q342R, P343A, E345T, L3511, T359S, N361K, Q362K, G371N, P374S, S375E, D376A, A378S.

29. The method of increasing the direct cell killing ability of an IgG1 antibody or antigen-binding fragment thereof according to embodiment 24 wherein the method comprises modifying one or more residues of the Fc region selected from: N286, K288, K290, A339, Q342, P343, R344, E345, L351, S354, D356, E357, L358, T359, N361, Q362, K370, G371, Y373, P374, S375, D376, A378.

30. The method according to embodiment 29 wherein the one or more modified residues are selected from: N286T, K288W, K2900, A339P, Q342R, P343A, R344Q, E345T, L3511, S354P, D356E, E357Q, L358M, T359S, N361K, Q362K, K370T, G371N, Y373F, P374S, S375E, D376A, A378S.

31. The method of increasing the direct cell killing ability of an IgG1 antibody or antigen-binding fragment thereof according to embodiment 24 wherein the method comprises modifying one or more residues of the Fc region selected from: N286, K288, K290, E294, Y300, V305, A339, Q342, P343, R344, E345, L351, S354, D356, E357, L358, T359, N361, Q362, K370, G371, Y373, P374, S375, D376, A378.

32. The method according to embodiment 31 wherein the one or more modified residues are selected from: N286T, K288W, K290Q, E294A, Y300F, V305A, A339P, Q342R, P343A, R344Q, E345T, L3511, S354P, D356E, E357Q, L358M, T359S, N361K, Q362K, K370T, G371N, Y373F, P374S, S375E, D376A, A378S.

33. A pharmaceutical composition comprising the modified IgG1 antibody or antigen-binding fragment thereof according to any one of embodiments 1 to 23, and a pharmaceutically acceptable carrier.

34. The pharmaceutical composition according to embodiment 33, further comprising at least one other therapeutic agent.

35. The pharmaceutical composition according to embodiment 33 or 34 comprising the modified IgG1 antibody or antigen-binding fragment thereof according to any one of embodiments 1 to 23 and an immunomodulatory agent.

36. A modified IgG1 antibody or antigen-binding fragment thereof according to any one of embodiments 1 to 23 or a composition according to any one of embodiments 33-35 for use as a medicament.

37. A modified IgG1 antibody or antigen-binding fragment thereof according to any one of embodiments 1 to 23 or a composition according to any one of embodiments 33-35 for use in the treatment of cancer, autoimmune diseases, inflammatory diseases or infectious diseases.

38. A method of treating an individual having a disease comprising administering to said individual a pharmaceutically effective amount of a modified IgG1 antibody or antigen-binding fragment thereof according to any one of embodiments 1 to 23 or a composition according to any one of embodiments 33-35.

39. The method of treating an individual according to embodiment 38, wherein the disease is selected from the group of cancer, autoimmune disease, inflammatory disease and infectious disease.

40. The method of treating an individual according to any one of 38-39, wherein the method further comprises administering an additional therapeutic agent to the individual.

41. The method of treating an individual according to embodiment 40 wherein the additional therapeutic agent is an immunomodulatory agent.

42. A kit comprising a modified IgG1 antibody or antigen-binding fragment thereof according to any one of embodiments 1-23 or a composition according to any one of embodiments 33-35, wherein said modified IgG1 antibody or antigen-binding fragment thereof, or composition is in one or more containers such as vials.

43. The kit according to embodiment 42, wherein the modified IgG1 antibody or antigen-binding fragment thereof or composition is for simultaneous, separate or sequential use in therapy.

44. Use of a modified IgG1 antibody or antigen-binding fragment thereof according to any one of embodiments 1-23 or a composition according to any one of embodiments 33-35 for the manufacture of a medicament for treatment of a disease.

45. The use according to embodiment 44, wherein the disease is cancer, autoimmune disease, inflammatory disease or infectious disease.

46. A modified IgG1 antibody or antigen-binding fragment thereof comprising one or more residue modifications to the Fc region at residue positions selected from: Q342, P343, E345, N361, Q362, P374, D376.

47. A modified IgG1 antibody or antigen-binding fragment thereof comprising one or more modifications to the Fc region selected from: Q342R, P343A, E345T, N361K, 0362K, P374S, D376A.

48. A modified IgG1 antibody or antigen-binding fragment thereof comprising one or more residue modifications to the Fc region at residue positions selected from: N286, K288, K290, 0342, P343, E345, L351, T359, N361, Q362, G371, P374, S375, D376, A378.

49. A modified IgG1 antibody or antigen-binding fragment thereof comprising one or more modifications to the Fc region selected from: N286T, K288W, K290Q, Q342R, P343A, E345T, L3511, T359S, N361K, Q362K, G371N, P374S, S375E, D376A, A378S.

50. A modified IgG1 antibody or antigen-binding fragment thereof comprising one or more residue modifications to the Fc region at residue positions selected from: N286, K288, K290, A339, Q342, P343, R344, E345, L351, S354, D356, E357, L358, T359, N361, 0362, K370, G371, Y373, P374, S375, D376, A378.

51. A modified IgG1 antibody or antigen-binding fragment thereof comprising one or more modifications to the Fc region selected from: N286T, K288W, K2900, A339P, Q342R, P343A, R344Q, E345T, L3511, S354P, D356E, E3570, L358M, T359S, N361K, 0362K, K370T, G371N, Y373F, P374S, S375E, D376A, A378S.

52. A modified IgG1 antibody or antigen-binding fragment thereof comprising one or more residue modifications to the Fc region at residue positions selected from: N286, K288, K290, E294, Y300, V305, A339, Q342, P343, R344, E345, L351, S354, D356, E357, L358, T359, N361, Q362, K370, G371, Y373, P374, S375, D376, A378.

53. A modified IgG1 antibody or antigen-binding fragment thereof comprising one or more modifications to the Fc region selected from: N286T, K288W, K290Q, E294A, Y300F, V305A, A339P, Q342R, P343A, R3440, E345T, L3511, S354P, D356E, E357Q, L358M, T359S, N361K, Q362K, K370T, G371N, Y373F, P374S, S375E, D376A, A378S.

54. A modified IgG1 antibody or antigen binding fragment thereof comprising one or more of the sequences disclosed in FIG. 19.

55. A modified IgG1 antibody or antigen binding fragment thereof comprising a heavy chain and a light chain sequence as disclosed in FIG. 19.

REFERENCES

Abdelmoula, M., F. Spertini, T. Shibata, Y. Gyotoku, S. Luzuy, P. H. Lambert, and S. Izui. 1989. 'IgG3 is the major source of cryoglobulins in mice', J Immunol, 143: 526-32.

Ausubel, F. M., R. Brent, R. E. Kingston, D. D. Moore, J. G. Seidman, J. A. Smith, and K. Struhl. 1992. Short protocols in molecular biology: a compendium of methods from Current protocols in molecular biology (Brooklyn, NY: Green Pub. Associates: New York, NY: Wiley).

Azinovic, I., G. L. DeNardo, K. R. Lamborn, G. Mirick, D. Goldstein, B. M. Bradt, and S. J. DeNardo. 2006. 'Survival benefit associated with human anti-mouse antibody (HAMA) in patients with B-cell malignancies', Cancer/mmunol/mmunother, 55: 1451-8.

Burris, H. A., 3rd, L. S. Rosen, C. M. Rocha-Lima, J. Marshall, S. Jones, R. B. Cohen, L. A. Kunkel, D. Loo, J. Baughman, S. J. Stewart, and N. Lewis. 2010. 'Phase 1 experience with an anti-glycotope monoclonal antibody, RAV12, in recurrent adenocarcinoma', Clin Cancer Res, 16:1673-81.

Carter, P. J. 2006. 'Potent antibody therapeutics by design', Nat Rev Immunol, 6: 343-57.

Chua, J. X., M. Vankemmelbeke, R. S. McIntosh, P. A. Clarke, R. Moss, T. Parsons, I. Spendlove, A. M. Zaitoun, S. Madhusudan, and L. G. Durrant. 2015. 'Monoclonal Antibodies Targeting LecLex-Related Glycans with Potent Antitumor Activity', Clin Cancer Res, 21: 2963-74.

Cooper, L. J., J. C. Schimenti, D. D. Glass, and N. S. Greenspan. 1991. 'H chain C domains influence the strength of binding of IgG for streptococcal group A carbohydrate', J Immunol, 146: 2659-63.

D'Arcy, C. A., and M. Mannik. 2001. 'Serum sickness secondary to treatment with the murine-human chimeric antibody IDEC-C2B8 (rituximab)', Arthritis Rheum, 44: 1717-8.

Dalziel, M., M. Crispin, C. N. Scanlan, N. Zitzmann, and R. A. Dwek. 2014. 'Emerging principles for the therapeutic exploitation of glycosylation', Science, 343: 1235681.

de Jong, R. N., F. J. Beurskens, S. Verploegen, K. Strumane, M. D. van Kampen, M. Voorhorst, W. Horstman, P. J. Engelberts, S. C. Oostindie, G. Wang, A. J. Heck, J. Schuurman, and P. W. Parren. 2016. 'A Novel Platform for the Potentiation of Therapeutic Antibodies Based on Antigen-Dependent Formation of IgG Hexamers at the Cell Surface', PLoS Biol, 14: e1002344.

DeLano, W. L., M. H. Ultsch, A. M. de Vos, and J. A. Wells. 2000. 'Convergent solutions to binding at a protein-protein interface', Science, 287: 1279-83.

Diebolder, C. A., F. J. Beurskens, R. N. de Jong, R. I. Koning, K. Strumane, M. A. Lindorfer, M. Voorhorst, D. Ugurlar, S. Rosati, A. J. Heck, J. G. van de Winkel, I. A. Wilson, A. J. Koster, R. P. Taylor, E. O. Saphire, D. R. Burton, J. Schuurman, P. Gros, and P. W. Parren. 2014. 'Complement is activated by IgG hexamers assembled at the cell surface', Science, 343: 1260-3.

Durrant, L. G., S. J. Harding, N. H. Green, L. D. Buckberry, and T. Parsons. 2006. 'A new anticancer glycolipid monoclonal antibody, SC104, which directly induces tumor cell apoptosis', Cancer Res, 66: 5901-9.

Eppstein, D. A., Y. V. Marsh, M. van der Pas, P. L. Feigner, and A. B. Schreiber. 1985. 'Biological activity of liposome-encapsulated murine interferon gamma is mediated by a cell membrane receptor', Proc Natl Acad Sci USA, 82: 3688-92.

Faraj, S., M. Bahri, S. Fougeray, A. El Roz, J. Fleurence, J. Veziers, M. D. Leclair, E. Thebaud, F. Paris, and S. Birkle. 2017. 'Neuroblastoma chemotherapy can be augmented by immunotargeting O-acetyl-GD2 tumor-associated ganglioside', Oncoimmunology, 7: e1373232.

Galluzzi, L., A. Buque, O. Kepp, L. Zitvogel, and G. Kroemer. 2017. 'Immunogenic cell death in cancer and infectious disease', Nat Rev Immunol, 17: 97-111.

Greenspan, N. S., and L. J. Cooper. 1992. 'Intermolecular cooperativity: a clue to why mice have IgG3?', Immunol Today, 13:164-8.

——. 1993. 'Cooperative binding by mouse IgG3 antibodies: implications for functional affinity, effector function, and isotype restriction', Springer Semin Immunopathol, 15: 275-91.

Greenspan, N. S., D. A. Dacek, and L. J. Cooper. 1989. 'Cooperative binding of two antibodies to independent antigens by an Fc-dependent mechanism', FASEB J, 3: 2203-7.

Greenspan, N. S., W. J. Monafo, and J. M. Davie. 1987. 'Interaction of IgG3 anti-streptococcal group A carbohydrate (GAC) antibody with streptococcal group A vaccine: enhancing and inhibiting effects of anti-GAC, anti-isotypic, and anti-idiotypic antibodies', J Immunol, 138: 285-92.

Grey, H. M., J. W. Hirst, and M. Cohn. 1971. 'A new mouse immunoglobulin: IgG3', J Exp Med, 133: 289-304.

Hege, K. M., E. K. Bergsland, G. A. Fisher, J. J. Nemunaitis, R. S. Warren, J. G. McArthur, A. A. Lin, J. Schlom, C. H. June, and S. A. Sherwin. 2017. 'Safety, tumor trafficking and immunogenicity of chimeric antigen receptor (CAR)-T cells specific for TAG-72 in colorectal cancer', J Immunother Cancer, 5: 22.

Hernandez, A. M., N. Rodriguez, J. E. Gonzalez, E. Reyes, T. Rondon, T. Grinan, A. Macias, S. Alfonso, A. M. Vazquez, and R. Perez. 2011. 'Anti-NeuGcGM3 antibodies, actively elicited by idiotypic vaccination in nonsmall cell lung cancer patients, induce tumor cell death by an oncosis-like mechanism', J Immunol, 186: 3735-44.

Hovenden, M., M. A. Hubbard, D. P. Aucoin, P. Thorkildson, D. E. Reed, W. H. Welch, C. R. Lyons, J. A. Lovchik, and T. R. Kozel. 2013. 'IgG subclass and heavy chain domains contribute to binding and protection by mAbs to the poly gamma-D-glutamic acid capsular antigen of Bacillus anthracis', PLoS Pathog, 9: e1003306.

Hwang, K. J., K. F. Luk, and P. L. Beaumier. 1980. 'Hepatic uptake and degradation of unilamellar sphingomyelin/cholesterol liposomes: a kinetic study', Proc Nat Acad Sci USA, 77: 4030-4.

Jawa, V., L. P. Cousens, M. Awwad, E. Wakshull, H. Kropshofer, and A. S. De Groot. 2013. 'T-cell dependent immunogenicity of protein therapeutics: Preclinical assessment and mitigation', Clin Immunol, 149: 534-55.

Klaus, T., and J. Bereta. 2018. 'CH2 Domain of Mouse IgG3 Governs Antibody Oligomerization, Increases Functional Affinity to Multivalent Antigens and Enhances Hemagglutination', Front Immunol, 9:1096.

Labrada, M., D. Dorvignit, G. Hevia, N. Rodriguez-Zhurbenko, A. M. Hernandez, A. M. Vazquez, and L. E. Fernandez. 2018. 'GM3(Neu5Gc) ganglioside: an evolution fixed neoantigen for cancer immunotherapy', Semin Oncol, 45: 41-51.

Ladenstein, R., U. Potschger, D. Valteau-Couanet, R. Luksch, V. Castel, I. Yaniv, G. Laureys, P. Brock, J. M. Michon, C. Owens, T. Trahair, G. C. F. Chan, E. Ruud, H. Schroeder, M. Beck Popovic, G. Schreier, H. Loibner, P. Ambros, K. Holmes, M. R. Castellani, M. N. Gaze, A. Garaventa, A. D. J. Pearson, and H. N. Lode. 2018. 'Interleukin 2 with anti-GD2 antibody ch14.18/CHO (dinutuximab beta) in patients with high-risk neuroblastoma (HR-NBL1/SIOPEN): a multicentre, randomised, phase 3 trial', *Lancet Oncol*, 19: 1617-29.

Loo, D., N. Pryer, P. Young, T. Liang, S. Coberly, K. L. King, K. Kang, P. Roberts, M. Tsao, X. Xu, B. Potts, and J. P. Mather. 2007. 'The glycotope-specific RAV12 monoclonal antibody induces oncosis in vitro and has antitumor activity against gastrointestinal adenocarcinoma tumor xenografts in vivo', *Mol Cancer Ther*, 6: 856-65.

Metheringham, R. L., V. A. Pudney, B. Gunn, M. Towey, I. Spendlove, and L. G. Durrant. 2009. 'Antibodies designed as effective cancer vaccines', MAbs, 1: 71-85.

Miotti, S., D. R. Negri, O. Valota, M. Calabrese, R. L. Bolhuis, J. W. Gratama, M. I. Colnaghi, and S. Canevari. 1999. 'Level of anti-mouse-antibody response induced by bi-specific monoclonal antibody OC/TR in ovarian-carcinoma patients is associated with longer survival', *Int J Cancer*, 84: 62-8.

Noble, P., I. Spendlove, S. Harding, T. Parsons, and L. G. Durrant. 2013. 'Therapeutic targeting of Lewis(y) and Lewis(b) with a novel monoclonal antibody 692/29', *PLoS One*, 8: e54892.

Oganesyan, V., M. M. Damschroder, K. E. Cook, Q. Li, C. Gao, H. Wu, and W. F. Dall'Acqua. 2014. 'Structural insights into neonatal Fc receptor-based recycling mechanisms', *J Biol Chem*, 289: 7812-24.

Pinho, S. S., and C. A. Reis. 2015. 'Glycosylation in cancer: mechanisms and clinical implications', *Nat Rev Cancer*, 15: 540-55.

Pluckthun, A. 1991. 'Antibody engineering: advances from the use of *Escherichia coli* expression systems', Biotechnology (N Y), 9: 545-51.

Rabu, C., R. McIntosh, Z. Jurasova, and L. Durrant. 2012. 'Glycans as targets for therapeutic antitumor antibodies', *Future Oncol*, 8: 943-60.

Reff, M. E. 1993. 'High-level production of recombinant immunoglobulins in mammalian cells', CurrOpin *Biotechnol*, 4: 573-6.

Rodriguez, E., S. T. T. Schetters, and Y. van Kooyk. 2018. 'The tumour glyco-code as a novel immune checkpoint for immunotherapy', *Nat Rev Immunol*, 18: 204-11.

Roque-Navarro, L., K. Chakrabandhu, J. de Leon, S. Rodriguez, C. Toledo, A. Carr, C. M. de Acosta, A. O. Hueber, and R. Perez. 2008. 'Anti-ganglioside antibody-induced tumor cell death by loss of membrane integrity', *Mol Cancer Ther*, 7: 2033-41.

Sambrook, J., E. F. Fritsch, and T. Maniatis. 1989. *Molecular Cloning: a laboratory manual* (Cold Spring Harbor, N.Y.: Cold Spring Harbor Laboratory, 1989).

Saphire, E. O., P. W. Parren, R. Pantophlet, M. B. Zwick, G. M. Morris, P. M. Rudd, R. A. Dwek, R. L. Stanfield, D. R. Burton, and I. A. Wilson. 2001. 'Crystal structure of a neutralizing human IGG against HIV-1: a template for vaccine design', *Science*, 293: 1155-9.

Schroff, R. W., K. A. Foon, S. M. Beatty, R. K. Oldham, and A. C. Morgan, Jr. 1985. 'Human anti-murine immunoglobulin responses in patients receiving monoclonal antibody therapy', *Cancer Res*, 45: 879-85.

Trill, J. J., A. R. Shatzman, and S. Ganguly. 1995. 'Production of monoclonal antibodies in COS and CHO cells', *Curr Opin Biotechnol*, 6: 553-60.

Ugurlar, D., S. C. Howes, B. J. de Kreuk, R. I. Koning, R. N. de Jong, F. J. Beurskens, J. Schuurman, A. J. Koster, T. H. Sharp, Pwhi Parren, and P. Gros. 2018. 'Structures of C1-IgG1 provide insights into how danger pattern recognition activates complement', *Science*, 359: 794-97.

Vanden Berghe, T., N. Vanlangenakker, E. Parthoens, W. Deckers, M. Devos, N. Festjens, C. J. Guerin, U. T. Brunk, W. Declercq, and P. Vandenabeele. 2010. 'Necroptosis, necrosis and secondary necrosis converge on similar cellular disintegration features', Cell Death Differ, 17: 922-30.

Wang, X., M. Mathieu, and R. J. Brezski. 2018. 'IgG Fc engineering to modulate antibody effector functions', Protein Cell, 9: 63-73.

Welt, S., E. A. Carswell, C. W. Vogel, H. F. Oettgen, and L. J. Old. 1987. 'Immune and nonimmune effector functions of IgG3 mouse monoclonal antibody R24 detecting the disialoganglioside GD3 on the surface of melanoma cells', *Clin Immunol Immunopathol*, 45: 214-29.

Yatim, N., S. Cullen, and M. L. Albert. 2017. 'Dying cells actively regulate adaptive immune responses', *Nat Rev Immunol*, 17: 262-75.

Zheng, J. Y., H. L. Tan, P. T. Matsudaira, and A. Choo. 2017. 'Excess reactive oxygen species production mediates monoclonal antibody-induced human embryonic stem cell death via oncosis', *Cell Death Differ*, 24: 546-58.

The invention claimed is:

1. A modified IgG1 antibody or antigen-binding fragment thereof comprising residues of an Fc-region of an immunoglobulin and a binding region, wherein residues of the Fc-region comprise N286, K288, K290, Q342, P343, E345, L351, T359, N361, Q362, G371, P374, S375, D376, and A378, numbered according to the IMGT system for the numbering of antibody sequences, are modified to the corresponding residue from a mouse IgG3 antibody, and wherein the modified IgG1 antibody or antigen-binding fragment thereof has enhanced when compared to a corresponding IgG1 antibody or antigen-binding fragment thereof comprising wildtype Fc-region residues.

2. The modified IgG1 antibody or antigen-binding fragment thereof according to claim 1 wherein the avidity of the modified IgG1 antibody or antigen-binding fragment thereof is enhanced by at least 10% when compared to a corresponding IgG1 antibody or antigen-binding fragment thereof comprising wildtype Fc-region residues.

3. The modified IgG1 antibody or antigen-binding fragment thereof according to claim 1, wherein the modified IgG1 antibody or antigen-binding fragment thereof has enhanced direct cell-killing independent of the presence of complement or immune effector cells when compared to a corresponding IgG1 antibody or antigen-binding fragment thereof comprising wildtype Fc-region residues.

4. The modified IgG1 antibody or antigen-binding fragment thereof according to claim 3 wherein the direct cell-killing independent of the presence of complement or immune effector cells of the modified IgG1 antibody or antigen-binding fragment thereof is enhanced by at least 10% when compared to a corresponding IgG1 antibody or antigen-binding fragment thereof comprising wildtype Fc-region residues.

5. The modified IgG1 antibody or antigen-binding fragment thereof according to claim 1, wherein the modified residues of the Fc-region comprise: N286T, K288W, K290Q, Q342R, P343A, E345T, L351I, T359S, N361K, Q362K, G371N, P374S, S375E, D376A, and A378S.

6. The modified IgG1 antibody or antigen-binding fragment thereof according to claim 1, wherein the residues of the Fc-region modified to the corresponding residue from a mouse IgG3 antibody are comprise: N286, K288, K290, A339, Q342, P343, R344, E345, L351, S354, D356, E357, L358, T359, N361, Q362, K370, G371, Y373, P374, S375, D376, and A378.

7. The modified IgG1 antibody or antigen-binding fragment thereof according to claim 1, wherein the modified residues of the Fc-region comprise: N286T, K288W, K290Q, A339P, Q342R, P343A, R344Q, E345T, L351I, S354P, D356E, E357Q, L358M, T359S, N361K, Q362K, K370T, G371N, Y373F, P374S, S375E, D376A, and A378S.

8. The modified IgG1 antibody or antigen-binding fragment thereof according to claim 1, wherein the residues of the Fc-region modified to the corresponding residue from a mouse IgG3 antibody comprise: N286, K288, K290, E294, Y300, V305, A339, Q342, P343, R344, E345, L351, S354, D356, E357, L358, T359, N361, Q362, K370, G371, Y373, P374, S375, D376, and A378.

9. The modified IgG1 antibody or antigen-binding fragment thereof according to claim 1, wherein the modified residues of the Fc-region comprise: N286T, K288W, K290Q, E294A, Y300F, V305A, A339P, Q342R, P343A, R344Q, E345T, L351I, S354P, D356E, E357Q, L358M, T359S, N361K, Q362K, K370T, G371N, Y373F, P374S, S375E, D376A and A378S.

10. A method of increasing the direct cell killing ability independent of the presence of complement or immune effector cells of an IgG1 antibody or antigen-binding fragment thereof comprising one or more residues of an Fc-region of an immunoglobulin and a binding region, wherein the method comprises replacing one or more residues of the CH2 and/or the CH3 domains of said Fc-region with one or more corresponding residues from mouse IgG3 CH2 and/or CH3 domains, and wherein the residues replaced with the corresponding residue from a mouse IgG3 antibody comprise N286, K288, K290, Q342, P343, E345, L351, T359, N361, Q362, G371, P374, S375, D376, and A378, numbered according to the IMGT system for the numbering of antibody sequences.

11. The method according to claim 10:

(a) the modified residues comprise: N286T, K288W, K290Q, Q342R, P343A, E345T, L351I, T359S, N361K, Q362K, G371N, P374S, S375E, D376A and A378S;

(b) the residues replaced with the corresponding residue from a mouse IgG3 antibody comprise: N286, K288, K290, A339, Q342, P343, R344, E345, L351, S354, D356, E357, L358, T359, N361, Q362, K370, G371, Y373, P374, S375, D376 and A378, optionally wherein the modified residues comprise: N286T, K288W, K290Q, A339P, Q342R, P343A, R344Q, E345T, L351I, S354P, D356E, E357Q, L358M, T359S, N361K, Q362K, K370T, G371N, Y373F, P374S, S375E, D376A and A378S; or (c) N286, K288, K290, E294, Y300, V305, A339, Q342, P343, R344, E345, L351, S354, D356, E357, L358, T359, N361, Q362, K370, G371, Y373, P374, S375, D376 and A378, optionally wherein the modified residues comprise: N286T, K288W, K290Q, E294A, Y300F, V305A, A339P, Q342R, P343A, R344Q, E345T, L351I, S354P, D356E, E357Q, L358M, T359S, N361K, Q362K, K370T, G371N, Y373F, P374S, S375E, D376A and A378S.

12. A pharmaceutical composition comprising the modified IgG1 antibody or antigen-binding fragment thereof according to claim 1, and a pharmaceutically acceptable carrier.

13. The pharmaceutical composition according to claim 12, further comprising at least one other therapeutic agent, optionally wherein the additional agent is an immunomodulatory agent.

14. A kit comprising a modified IgG1 antibody or antigen-binding fragment thereof according to claim 1, wherein said modified IgG1 antibody or antigen-binding fragment thereof, or composition is in one or more containers such as vials.

15. The kit according to claim 14, wherein the modified IgG1 antibody or antigen-binding fragment thereof or composition is for simultaneous, separate or sequential use in therapy.

* * * * *

SEQUENCE LISTING

```
<160> NUMBER OF SEQ ID NOS: 47

<210> SEQ ID NO 1
<211> LENGTH: 35
<212> TYPE: PRT
<213> ORGANISM: Artificial sequence
<220> FEATURE:
<223> OTHER INFORMATION: Modified Fc motif
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (5)..(19)
<223> OTHER INFORMATION: Xaa can be any amino acid
<220> FEATURE:
```

```
<221> NAME/KEY: misc_feature
<222> LOCATION: (22)..(32)
<223> OTHER INFORMATION: Xaa can be any amino acid
<220> FEATURE:
<221> NAME/KEY: misc_feature
<222> LOCATION: (34)..(34)
<223> OTHER INFORMATION: Xaa can be any amino acid

<400> SEQUENCE: 1

Arg Ala Xaa Thr Xaa Xaa Xaa Xaa Xaa Xaa Xaa Xaa Xaa Xaa Xaa Xaa
1               5                   10                  15

Xaa Xaa Xaa Lys Lys Xaa Xaa Xaa Xaa Xaa Xaa Xaa Xaa Xaa Xaa
            20                  25                  30

Ser Xaa Ala
        35

<210> SEQ ID NO 2
<211> LENGTH: 93
<212> TYPE: PRT
<213> ORGANISM: Artificial sequence
<220> FEATURE:
<223> OTHER INFORMATION: Modified Fc motif
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (6)..(56)
<223> OTHER INFORMATION: Xaa can be any amino acid
<220> FEATURE:
<221> NAME/KEY: misc_feature
<222> LOCATION: (59)..(59)
<223> OTHER INFORMATION: Xaa can be any amino acid
<220> FEATURE:
<221> NAME/KEY: misc_feature
<222> LOCATION: (61)..(65)
<223> OTHER INFORMATION: Xaa can be any amino acid
<220> FEATURE:
<221> NAME/KEY: misc_feature
<222> LOCATION: (67)..(73)
<223> OTHER INFORMATION: Xaa can be any amino acid
<220> FEATURE:
<221> NAME/KEY: misc_feature
<222> LOCATION: (75)..(75)
<223> OTHER INFORMATION: Xaa can be any amino acid
<220> FEATURE:
<221> NAME/KEY: misc_feature
<222> LOCATION: (78)..(85)
<223> OTHER INFORMATION: Xaa can be any amino acid
<220> FEATURE:
<221> NAME/KEY: misc_feature
<222> LOCATION: (87)..(88)
<223> OTHER INFORMATION: Xaa can be any amino acid
<220> FEATURE:
<221> NAME/KEY: misc_feature
<222> LOCATION: (92)..(92)
<223> OTHER INFORMATION: Xaa can be any amino acid

<400> SEQUENCE: 2

Thr Xaa Trp Xaa Gln Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Arg Ala Xaa Thr Xaa Xaa Xaa Xaa
```

-continued

```
              50                55                60

Xaa Ile Xaa Xaa Xaa Xaa Xaa Xaa Xaa Ser Xaa Lys Lys Xaa Xaa Xaa
65                    70                75                80

Xaa Xaa Xaa Xaa Xaa Asn Xaa Xaa Ser Glu Ala Xaa Ser
              85                90

<210> SEQ ID NO 3
<211> LENGTH: 93
<212> TYPE: PRT
<213> ORGANISM: Artificial sequence
<220> FEATURE:
<223> OTHER INFORMATION: Modified Fc motif
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (6)..(19)
<223> OTHER INFORMATION: Xaa can be any amino acid
<220> FEATURE:
<221> NAME/KEY: misc_feature
<222> LOCATION: (21)..(53)
<223> OTHER INFORMATION: Xaa can be any amino acid
<220> FEATURE:
<221> NAME/KEY: misc_feature
<222> LOCATION: (55)..(56)
<223> OTHER INFORMATION: Xaa can be any amino acid
<220> FEATURE:
<221> NAME/KEY: misc_feature
<222> LOCATION: (61)..(65)
<223> OTHER INFORMATION: Xaa can be any amino acid
<220> FEATURE:
<221> NAME/KEY: misc_feature
<222> LOCATION: (67)..(68)
<223> OTHER INFORMATION: Xaa can be any amino acid
<220> FEATURE:
<221> NAME/KEY: misc_feature
<222> LOCATION: (70)..(70)
<223> OTHER INFORMATION: Xaa can be any amino acid
<220> FEATURE:
<221> NAME/KEY: misc_feature
<222> LOCATION: (75)..(75)
<223> OTHER INFORMATION: Xaa can be any amino acid
<220> FEATURE:
<221> NAME/KEY: misc_feature
<222> LOCATION: (78)..(84)
<223> OTHER INFORMATION: Xaa can be any amino acid
<220> FEATURE:
<221> NAME/KEY: misc_feature
<222> LOCATION: (86)..(87)
<223> OTHER INFORMATION: Xaa can be any amino acid
<220> FEATURE:
<221> NAME/KEY: misc_feature
<222> LOCATION: (92)..(92)
<223> OTHER INFORMATION: Xaa can be any amino acid

<400> SEQUENCE: 3

Thr Xaa Trp Xaa Gln Xaa Xaa Xaa Xaa Xaa Xaa Xaa Xaa Xaa Xaa Xaa
1               5                   10                  15

Xaa Xaa Xaa Ala Xaa Xaa Xaa Xaa Xaa Xaa Xaa Xaa Xaa Xaa Xaa Xaa
              20                25                30

Xaa Xaa Xaa Xaa Xaa Xaa Xaa Xaa Xaa Xaa Xaa Xaa Xaa Xaa Xaa Xaa
        35                40                45

Xaa Xaa Xaa Xaa Xaa Pro Xaa Xaa Arg Ala Gln Thr Xaa Xaa Xaa Xaa
    50                55                60

Xaa Ile Xaa Xaa Pro Xaa Glu Gln Met Ser Xaa Lys Lys Xaa Xaa Xaa
```

-continued

```
65              70              75              80

Xaa Xaa Xaa Xaa Thr Xaa Xaa Phe Ser Glu Ala Xaa Ser
                85              90

<210> SEQ ID NO 4
<211> LENGTH: 93
<212> TYPE: PRT
<213> ORGANISM: Artificial sequence
<220> FEATURE:
<223> OTHER INFORMATION: Modified Fc motif
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa can be any amino acid
<220> FEATURE:
<221> NAME/KEY: misc_feature
<222> LOCATION: (6)..(8)
<223> OTHER INFORMATION: Xaa can be any amino acid
<220> FEATURE:
<221> NAME/KEY: misc_feature
<222> LOCATION: (10)..(14)
<223> OTHER INFORMATION: Xaa can be any amino acid
<220> FEATURE:
<221> NAME/KEY: misc_feature
<222> LOCATION: (16)..(19)
<223> OTHER INFORMATION: Xaa can be any amino acid
<220> FEATURE:
<221> NAME/KEY: misc_feature
<222> LOCATION: (21)..(53)
<223> OTHER INFORMATION: Xaa can be any amino acid
<220> FEATURE:
<221> NAME/KEY: misc_feature
<222> LOCATION: (55)..(56)
<223> OTHER INFORMATION: Xaa can be any amino acid
<220> FEATURE:
<221> NAME/KEY: misc_feature
<222> LOCATION: (61)..(65)
<223> OTHER INFORMATION: Xaa can be any amino acid
<220> FEATURE:
<221> NAME/KEY: misc_feature
<222> LOCATION: (67)..(68)
<223> OTHER INFORMATION: Xaa can be any amino acid
<220> FEATURE:
<221> NAME/KEY: misc_feature
<222> LOCATION: (70)..(70)
<223> OTHER INFORMATION: Xaa can be any amino acid
<220> FEATURE:
<221> NAME/KEY: misc_feature
<222> LOCATION: (75)..(75)
<223> OTHER INFORMATION: Xaa can be any amino acid
<220> FEATURE:
<221> NAME/KEY: misc_feature
<222> LOCATION: (78)..(84)
<223> OTHER INFORMATION: Xaa can be any amino acid
<220> FEATURE:
<221> NAME/KEY: misc_feature
<222> LOCATION: (87)..(87)
<223> OTHER INFORMATION: Xaa can be any amino acid
<220> FEATURE:
<221> NAME/KEY: misc_feature
<222> LOCATION: (92)..(92)
<223> OTHER INFORMATION: Xaa can be any amino acid

<400> SEQUENCE: 4

Thr Xaa Trp Xaa Gln Xaa Xaa Xaa Ala Xaa Xaa Xaa Xaa Xaa Phe Xaa
1               5               10              15

Xaa Xaa Xaa Ala Xaa Xaa Xaa Xaa Xaa Xaa Xaa Xaa Xaa Xaa Xaa
            20              25              30

Xaa Xaa Xaa Xaa Xaa Xaa Xaa Xaa Xaa Xaa Xaa Xaa Xaa Xaa Xaa
        35              40              45
```

```
Xaa Xaa Xaa Xaa Xaa Pro Xaa Xaa Arg Ala Gln Thr Xaa Xaa Xaa Xaa
    50                  55                  60

Xaa Ile Xaa Xaa Pro Xaa Glu Gln Met Ser Xaa Lys Lys Xaa Xaa Xaa
65                  70                  75                  80

Xaa Xaa Xaa Xaa Thr Asn Xaa Phe Ser Glu Ala Xaa Ser
                85                  90

<210> SEQ ID NO 5
<211> LENGTH: 5
<212> TYPE: PRT
<213> ORGANISM: Artificial sequence
<220> FEATURE:
<223> OTHER INFORMATION: Modified Fc motif
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa can be any amino acid

<400> SEQUENCE: 5

Thr Xaa Trp Xaa Gln
1               5

<210> SEQ ID NO 6
<211> LENGTH: 10
<212> TYPE: PRT
<213> ORGANISM: Artificial sequence
<220> FEATURE:
<223> OTHER INFORMATION: Modified Fc motif
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (5)..(9)
<223> OTHER INFORMATION: Xaa can be any amino acid

<400> SEQUENCE: 6

Arg Ala Xaa Thr Xaa Xaa Xaa Xaa Xaa Ile
1               5                   10

<210> SEQ ID NO 7
<211> LENGTH: 20
<212> TYPE: PRT
<213> ORGANISM: Artificial sequence
<220> FEATURE:
<223> OTHER INFORMATION: Modified Fc motif
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (5)..(12)
<223> OTHER INFORMATION: Xaa can be any amino acid
<220> FEATURE:
<221> NAME/KEY: misc_feature
<222> LOCATION: (14)..(15)
<223> OTHER INFORMATION: Xaa can be any amino acid
<220> FEATURE:
<221> NAME/KEY: misc_feature
<222> LOCATION: (19)..(19)
<223> OTHER INFORMATION: Xaa can be any amino acid

<400> SEQUENCE: 7

Ser Xaa Lys Lys Xaa Xaa Xaa Xaa Xaa Xaa Xaa Xaa Asn Xaa Xaa Ser
```

-continued

```
1                5               10              15

Glu Ala Xaa Ser
            20

<210> SEQ ID NO 8
<211> LENGTH: 8
<212> TYPE: PRT
<213> ORGANISM: Artificial sequence
<220> FEATURE:
<223> OTHER INFORMATION: Modified Fc motif
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (7)..(7)
<223> OTHER INFORMATION: Xaa can be any amino acid

<400> SEQUENCE: 8

Asn Xaa Xaa Ser Glu Ala Xaa Ser
1               5

<210> SEQ ID NO 9
<211> LENGTH: 699
<212> TYPE: DNA
<213> ORGANISM: Artificial sequence
<220> FEATURE:
<223> OTHER INFORMATION: 88 light chain DNS sequence (variable region +
      kappa constant)

<400> SEQUENCE: 9
atgagtgtgc tcactcaggt cctggcgttg ctgctgctgt ggcttacagg tgccagatgt      60
gacatccaga tgactcagtc tccaacctcc ctatctgcat ctgtgggaga aactgtcacc     120
atcacatgtc gaacaagtga gaatattcac aattttttaa catggtatca gcagaaacag     180
ggaaatctct ctcaggtcct ggtctataat gcaaaaacct taccagatgg tgtgccatca     240
aggttcagtg gcagtggatc aggaacacaa tattctctca gatcaacag cctgcagcct      300 gaagattttg ggacttatta ctgtcaacat ttttggagta gtccgtggac gttcggtgga     360
ggcaccaagc tggaaatcaa acgtacggta gcgccatctg tcttcatctt cccgccatct     420
gatgagcagt tgaaatctgg aactgcctct gttgtgtgcc tgctgaataa cttctatccc     480
agagaggcca aagtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcaccca tcagggcctg     660
agctcgcccg tcacaaagag cttcaacagg ggagagtgt                            699

<210> SEQ ID NO 10
<211> LENGTH: 233
<212> TYPE: PRT
<213> ORGANISM: Artificial sequence
<220> FEATURE:
<223> OTHER INFORMATION: 88 light chain protein sequence (variable
      region + kappa constant)

<400> SEQUENCE: 10

Met Ser Val Leu Thr Gln Val Leu Ala Leu Leu Leu Leu Trp Leu Thr
1               5               10              15

Gly Ala Arg Cys Asp Ile Gln Met Thr Gln Ser Pro Thr Ser Leu Ser
            20              25              30

Ala Ser Val Gly Glu Thr Val Thr Ile Thr Cys Arg Thr Ser Glu Asn
```

-continued

```
              35                40                45
Ile His Asn Phe Leu Thr Trp Tyr Gln Gln Lys Gln Gly Lys Ser Pro
     50                55                60

Gln Val Leu Val Tyr Asn Ala Lys Thr Leu Pro Asp Gly Val Pro Ser
65                70                75                80

Arg Phe Ser Gly Ser Gly Ser Gly Thr Gln Tyr Ser Leu Lys Ile Asn
                 85                90                95

Ser Leu Gln Pro Glu Asp Phe Gly Thr Tyr Tyr Cys Gln His Phe Trp
             100               105               110

Ser Ser Pro Trp Thr Phe Gly Gly Gly Thr Lys Leu Glu Ile Lys Arg
             115               120               125

Thr Val Ala Pro Ser Val Phe Ile Phe Pro Pro Ser Asp Glu Gln Leu
     130               135               140

Lys Ser Gly Thr Ala Ser Val Val Cys Leu Leu Asn Asn Phe Tyr Pro
145               150               155               160

Arg Glu Ala Lys Val Gln Trp Lys Val Asp Asn Ala Leu Gln Ser Gly
             165               170               175

Asn Ser Gln Glu Ser Val Thr Glu Gln Asp Ser Lys Asp Ser Thr Tyr
             180               185               190

Ser Leu Ser Ser Thr Leu Thr Leu Ser Lys Ala Asp Tyr Glu Lys His
             195               200               205

Lys Val Tyr Ala Cys Glu Val Thr His Gln Gly Leu Ser Ser Pro Val
     210               215               220

Thr Lys Ser Phe Asn Arg Gly Glu Cys
225               230
```

```
<210> SEQ ID NO 11
<211> LENGTH: 1425
<212> TYPE: DNA
<213> ORGANISM: Artificial sequence
<220> FEATURE:
<223> OTHER INFORMATION: Heavy chain DNA sequence of i88v1 (variable +
      'improved' v1 constant region)

<400> SEQUENCE: 11
atgtacttgg gactgaactg tgtattcata gtttttctct taaatggtgt ccagagtgaa      60
gtgaaactcg aggagtctgg aggaggcttg gtgcaacctg gaggatccat gaaactctct     120
tgtgctgcct ctggattcac ttttagtgac gcctggatga actgggtccg ccagtctcca     180 gagaagggc ttgagtgggt tgctgaaatt agaagcaaag ttattaatcc tgcaatatac     240
tatgctgagt ctgtgaaaga gaggttcacc atattaagag atgattccaa aagtagtgtc     300
tacctgcaaa tgaacagctt aagagctgaa gacactggaa tttattactg ttccaggtct     360
actatgatta cgacaaggga cccgtcccgg tacttcgatg tctggggcgc agggaccacg     420
gtcaccgtct ccagcgcttc caccaagggc ccatcggtct tccccctggc accctcctcc     480
aagagcacct ctgggggcac agcggccctg ggctgcctgg tcaaggacta cttccccgaa     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660
ttgggcaccc agacctacat ctgcaacgtg aatcacaagc ccagcaacac caaggtggac     720
aagaaagttg agcccaaatc ttgtgacaaa actcacacat gcccaccgtg cccagcacct     780
gaactcctgg gggaccgtc agtcttcctc ttccccccaa aacccaagga caccctcatg     840
atctcccgga cccctgaggt cacatgcgtg gtggtggacg tgagccacga agaccctgag     900
```

-continued

```
gtcaagttca actggtacgt ggacggcgtg gaggtgcata cagcctggac acagccccgt      960
gaagagcagt acaacagtac ctaccgagtg gtcagtgtcc tcaccgtcct gcaccaggac     1020
tggctgaatg gcaaggagta caagtgcaag gtctccaaca aagccctccc agcccccatc     1080
gagaaaacca tctccaaacc caaaggaaga gcccagacac ctcaagtata caccataccc     1140
ccacctcgtg aacaaatgtc caagaagaag gttagtctga cctgcctggt caccaacttc     1200
ttctctgaag ccatcagtgt ggagtgggag agcaatgggc agccggagaa caactacaag     1260
accacgcctc ccgtgctgga ctccgacggc tccttcttcc tctacagcaa gctcaccgtg     1320
gacaagagca ggtggcagca ggggaacgtc ttctcatgct ccgtgatgca tgaggctctg     1380
cacaaccact acacgcagaa gagcctctcc ctgtctccgg gtaaa                     1425
```

```
<210> SEQ ID NO 12
<211> LENGTH: 475
<212> TYPE: PRT
<213> ORGANISM: Artificial sequence
<220> FEATURE:
<223> OTHER INFORMATION: Heavy chain protein sequence of i88v1
      (variable + 'improved' v1 constant region)

<400> SEQUENCE: 12

Met Tyr Leu Gly Leu Asn Cys Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asn Trp Val Arg Gln Ser Pro Glu Lys Gly Leu
    50                  55                  60

Glu Trp Val Ala Glu Ile Arg Ser Lys Val Ile Asn Pro Ala Ile Tyr
65                  70                  75                  80

Tyr Ala Glu Ser Val Lys Glu Arg Phe Thr Ile Leu Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Ser Arg Ser Thr Met Ile Thr Thr Arg Asp Pro
        115                 120                 125

Ser Arg Tyr Phe Asp Val Trp Gly Ala Gly Thr Thr Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270
```

```
Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Thr Ala Trp Thr Gln Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Pro Lys
            355                 360                 365

Gly Arg Ala Gln Thr Pro Gln Val Tyr Thr Ile Pro Pro Pro Arg Glu
    370                 375                 380

Gln Met Ser Lys Lys Lys Val Ser Leu Thr Cys Leu Val Thr Asn Phe
385                 390                 395                 400

Phe Ser Glu Ala Ile Ser Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
        450                 455                 460

Thr Gln Lys Ser Leu Ser Leu Ser Pro Gly Lys
465                 470                 475
```

<210> SEQ ID NO 13
<211> LENGTH: 1425
<212> TYPE: DNA
<213> ORGANISM: Artificial sequence
<220> FEATURE:
<223> OTHER INFORMATION: Heavy chain DNA sequence of i88v2 (variable +
      'improved' v2 constant region)

<400> SEQUENCE: 13

```
atgtacttgg gactgaactg tgtattcata gttttttctct taaatggtgt ccagagtgaa      60
gtgaaactcg aggagtctgg aggaggcttg gtgcaacctg gaggatccat gaaactctct     120
tgtgctgcct ctggattcac ttttagtgac gcctggatga actgggtccg ccagtctcca     180
gagaaggggc ttgagtgggt tgctgaaatt agaagcaaag ttattaatcc tgcaatatac     240
tatgctgagt ctgtgaaaga gaggttcacc atattaagag atgattccaa aagtagtgtc     300
tacctgcaaa tgaacagctt aagagctgaa gacactggaa tttattactg ttccaggtct     360
actatgatta cgacaaggga cccgtcccgg tacttcgatg tctggggcgc agggaccacg     420
gtcaccgtct ccagcgcttc caccaagggc ccatcggtct tccccctggc acctcctcc     480 aagagcacct ctgggggcac agcggccctg ggctgcctgg tcaaggacta cttccccgaa     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660
ttgggcaccc agacctacat ctgcaacgtg aatcacaagc ccagcaacac caaggtggac     720
aagaaagttg agcccaaatc ttgtgacaaa actcacacat gcccaccgtg cccagcacct     780
gaactcctgg ggggaccgtc agtcttcctc ttccccccaa aacccaagga caccctcatg     840
```

-continued

```
atctcccgga cccctgaggt cacatgcgtg gtggtggacg tgagccacga agaccctgag     900
gtcaagttca actggtacgt ggacggcgtg gaggtgcata cagcctggac acagccccgt     960
gaagagcagt acaacagtac ctaccgagtg gtcagtgtcc tcaccgtcct gcaccaggac    1020
tggctgaatg gcaaggagta caagtgcaag gtctccaaca aagccctccc agcccccatc    1080
gagaaaacca tctccaaagc caaaggaaga gcccgaacac ctcaagtata caccataccc    1140
ccatcccgtg atgagctgtc caagaagaag gttagtctga cctgcctggt caaaaacttc    1200
tattctgaag ccatcagtgt ggagtgggag agcaatgggc agccggagaa caactacaag    1260
accacgcctc ccgtgctgga ctccgacggc tccttcttcc tctacagcaa gctcaccgtg    1320
gacaagagca ggtggcagca ggggaacgtc ttctcatgct ccgtgatgca tgaggctctg    1380
cacaaccact acacgcagaa gagcctctcc ctgtctccgg gtaaa                     1425
```

<210> SEQ ID NO 14
<211> LENGTH: 475
<212> TYPE: PRT
<213> ORGANISM: Artificial sequence
<220> FEATURE:
<223> OTHER INFORMATION: Heavy chain protein sequence of i88v2
     (variable + 'improved' v2 constant region)

<400> SEQUENCE: 14

```
Met Tyr Leu Gly Leu Asn Cys Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asn Trp Val Arg Gln Ser Pro Glu Lys Gly Leu
    50                  55                  60

Glu Trp Val Ala Glu Ile Arg Ser Lys Val Ile Asn Pro Ala Ile Tyr
65                  70                  75                  80

Tyr Ala Glu Ser Val Lys Glu Arg Phe Thr Ile Leu Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Ser Arg Ser Thr Met Ile Thr Thr Arg Asp Pro
            115                 120                 125

Ser Arg Tyr Phe Asp Val Trp Gly Ala Gly Thr Thr Val Thr Val Ser
        130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
                180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
        210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
                245                 250                 255
```

```
Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
    290                 295                 300

Trp Tyr Val Asp Gly Val Glu Val His Thr Ala Trp Thr Gln Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Arg Ala Arg Thr Pro Gln Val Tyr Thr Ile Pro Pro Ser Arg Asp
    370                 375                 380

Glu Leu Ser Lys Lys Val Ser Leu Thr Cys Leu Val Lys Asn Phe
385                 390                 395                 400

Tyr Ser Glu Ala Ile Ser Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 15
<211> LENGTH: 1425
<212> TYPE: DNA
<213> ORGANISM: Artificial sequence
<220> FEATURE:
<223> OTHER INFORMATION: Heavy chain DNA sequence of i88v3 (variable +
      'improved' v3 constant region)

<400> SEQUENCE: 15
atgtacttgg gactgaactg tgtattcata gtttttctct taaatggtgt ccagagtgaa      60
gtgaaactcg aggagtctgg aggaggcttg gtgcaacctg gaggatccat gaaactctct     120
tgtgctgcct ctggattcac ttttagtgac gcctggatga actgggtccg ccagtctcca     180
gagaaggggc ttgagtgggt tgctgaaatt agaagcaaag ttattaatcc tgcaatatac     240
tatgctgagt ctgtgaaaga gaggttcacc atattaagag atgattccaa aagtagtgtc     300
tacctgcaaa tgaacagctt aagagctgaa gacactggaa tttattactg ttccaggtct     360
actatgatta cgacaaggga cccgtcccgg tacttcgatg tctggggcgc agggaccacg     420
gtcaccgtct ccagcgcttc caccaagggc ccatcggtct tccccctggc accctcctcc     480
aagagcacct ctgggggcac agcggccctg ggctgcctgg tcaaggacta cttccccgaa     540
ccggtgacgg tgtcgtggaa ctcaggcgcc ctgaccagcg gcgtgcacac cttcccggct     600
gtcctacagt cctcaggact ctactccctc agcagcgtgg tgaccgtgcc ctccagcagc     660
ttgggcaccc agacctacat ctgcaacgtg aatcacaagc ccagcaacac caaggtggac     720
aagaaagttg agcccaaatc ttgtgacaaa actcacacat gcccaccgtg cccagcacct     780
```

-continued

```
gaactcctgg gggaccgtc agtcttcctc ttcccccca aacccaagga caccctcatg          840
atctcccgga cccctgaggt cacatgcgtg gtggtggacg tgagccacga agaccctgag          900
gtcaagttca actggtacgt ggacggcgtg gaggtgcata atgccaagac aaagccccgt          960
gaagagcagt acaacagtac ctaccgagtg gtcagtgtcc tcaccgtcct gcaccaggac         1020
tggctgaatg gcaaggagta caagtgcaag gtctccaaca agccctccc agcccccatc         1080 gagaaaacca tctccaaagc caaggaaga gcccgaacac ctcaagtata caccctgccc         1140
ccatcccgtg atgagctgac caagaagaag gttagtctga cctgcctggt caaaggcttc         1200
tattctagcg ccatcgccgt ggagtgggag agcaatgggc agccggagaa caactacaag         1260
accacgcctc ccgtgctgga ctccgacggc tccttcttcc tctacagcaa gctcaccgtg         1320
gacaagagca ggtggcagca ggggaacgtc ttctcatgct ccgtgatgca tgaggctctg         1380
cacaaccact acacgcagaa gagcctctcc ctgtctccgg gtaaa                         1425
```

<210> SEQ ID NO 16
<211> LENGTH: 475
<212> TYPE: PRT
<213> ORGANISM: Artificial sequence
<220> FEATURE:
<223> OTHER INFORMATION: Heavy chain protein sequence of i88v3
      (variable + 'improved' v3 constant region)

<400> SEQUENCE: 16

```
Met Tyr Leu Gly Leu Asn Cys Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asn Trp Val Arg Gln Ser Pro Glu Lys Gly Leu
    50                  55                  60

Glu Trp Val Ala Glu Ile Arg Ser Lys Val Ile Asn Pro Ala Ile Tyr
65                  70                  75                  80

Tyr Ala Glu Ser Val Lys Glu Arg Phe Thr Ile Leu Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Ser Arg Ser Thr Met Ile Thr Thr Arg Asp Pro
        115                 120                 125

Ser Arg Tyr Phe Asp Val Trp Gly Ala Gly Thr Thr Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
                180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Lys Val Glu Pro Lys Ser Cys Asp Lys Thr His Thr Cys Pro Pro
```

-continued

```
                    245              250              255

Cys Pro Ala Pro Glu Leu Leu Gly Gly Pro Ser Val Phe Leu Phe Pro
            260              265              270

Pro Lys Pro Lys Asp Thr Leu Met Ile Ser Arg Thr Pro Glu Val Thr
        275              280              285

Cys Val Val Val Asp Val Ser His Glu Asp Pro Glu Val Lys Phe Asn
    290              295              300

Trp Tyr Val Asp Gly Val Glu Val His Asn Ala Lys Thr Lys Pro Arg
305              310              315              320

Glu Glu Gln Tyr Asn Ser Thr Tyr Arg Val Val Ser Val Leu Thr Val
                325              330              335

Leu His Gln Asp Trp Leu Asn Gly Lys Glu Tyr Lys Cys Lys Val Ser
            340              345              350

Asn Lys Ala Leu Pro Ala Pro Ile Glu Lys Thr Ile Ser Lys Ala Lys
        355              360              365

Gly Arg Ala Arg Thr Pro Gln Val Tyr Thr Leu Pro Pro Ser Arg Asp
    370              375              380

Glu Leu Thr Lys Lys Lys Val Ser Leu Thr Cys Leu Val Lys Gly Phe
385              390              395              400

Tyr Ser Ser Ala Ile Ala Val Glu Trp Glu Ser Asn Gly Gln Pro Glu
                405              410              415

Asn Asn Tyr Lys Thr Thr Pro Pro Val Leu Asp Ser Asp Gly Ser Phe
            420              425              430

Phe Leu Tyr Ser Lys Leu Thr Val Asp Lys Ser Arg Trp Gln Gln Gly
            435              440              445

Asn Val Phe Ser Cys Ser Val Met His Glu Ala Leu His Asn His Tyr
        450              455              460

Thr Gln Lys Ser Leu Ser Leu Ser Pro Gly Lys
465              470              475
```

<210> SEQ ID NO 17
<211> LENGTH: 717
<212> TYPE: DNA
<213> ORGANISM: Artificial sequence
<220> FEATURE:
<223> OTHER INFORMATION: 129 Light chain DNA sequence (variable region +
      Kappa constant)

<400> SEQUENCE: 17

```
atggaatcac agactcaggt cctcatgtcc ctgctgttct gggtatctac ctgtggggac      60
attgtgatga cacagtctcc atcctccctg actgtgacag caggagagaa ggtcactatg     120
agctgcaagt ccagtcagag tctgttaaac agtggaaatc aaaagaacta cttgacctgg     180
taccagcaga aaccagggca gcctcctaaa gtgttgatct actgggcatc cactagggaa     240
tctggggtcc ctgatcgctt cacaggcagt ggatctggaa cagatttcac tctcaccatc     300
agcagtgtgc aggctgaaga cctggcagtt tattactgtc agaatgatta tagttctcca     360
ttcacgttcg gctcggggac aaagttggaa ataaaacgta cggtagcggc cccatctgtc     420
ttcatcttcc cgccatctga tgagcagttg aaatctggaa ctgcctctgt tgtgtgcctg     480
ctgaataact ctatcccag agaggccaaa gtacagtgga aggtggataa cgccctccaa      540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgt        717
```

-continued

```
<210> SEQ ID NO 18
<211> LENGTH: 239
<212> TYPE: PRT
<213> ORGANISM: Artificial sequence
<220> FEATURE:
<223> OTHER INFORMATION: 129 Light chain protein sequence (variable
      region + Kappa constant)

<400> SEQUENCE: 18

Met Glu Ser Gln Thr Gln Val Leu Met Ser Leu Leu Phe Trp Val Ser
1               5                   10                  15

Thr Cys Gly Asp Ile Val Met Thr Gln Ser Pro Ser Ser Leu Thr Val
            20                  25                  30

Thr Ala Gly Glu Lys Val Thr Met Ser Cys Lys Ser Ser Gln Ser Leu
        35                  40                  45

Leu Asn Ser Gly Asn Gln Lys Asn Tyr Leu Thr Trp Tyr Gln Gln Lys
    50                  55                  60

Pro Gly Gln Pro Pro Lys Val Leu Ile Tyr Trp Ala Ser Thr Arg Glu
65                  70                  75                  80

Ser Gly Val Pro Asp Arg Phe Thr Gly Ser Gly Ser Gly Thr Asp Phe
                85                  90                  95

Thr Leu Thr Ile Ser Ser Val Gln Ala Glu Asp Leu Ala Val Tyr Tyr
            100                 105                 110

Cys Gln Asn Asp Tyr Ser Ser Pro Phe Thr Phe Gly Ser Gly Thr Lys
            115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 19
<211> LENGTH: 1401
<212> TYPE: DNA
<213> ORGANISM: Artificial sequence
<220> FEATURE:
<223> OTHER INFORMATION: Heavy chain DNA sequence of i129v1 (variable +
      'improved' v1 constant region)

<400> SEQUENCE: 19
atgctgttgg ggctgaagtg ggttttcttt gttgtttttt atcaaggtgt gcattgtgag      60
gtgcagcttg ttgagtctgg tggaggattg gtgcagccta aagggtcatt gaaactctca     120
tgtgcagcct ctggattcac cttcaatacc tacgccatga actgggtccg ccaggctcca     180
ggaaagggtt tggaatgggt tgctcgcata agaagtaaaa gtaataatta tgcaacatat     240
tatgccgatt cagtgaaaga caggttcacc atatccagag atgattcaca aagcatgctc     300
tatctgcaaa tgaacaactt gaaaaaggag gacacagcca tgtattactg tgtagggtac     360
```

-continued

```
ggtagtgggg gaaactactg gggtcaagga acctcagtca ccgtctccag cgcttccacc        420
aagggcccat cggtcttccc cctggcaccc tcctccaaga gcacctctgg gggcacagcg        480
gccctgggct gcctggtcaa ggactacttc cccgaaccgg tgacggtgtc gtggaactca        540
ggcgccctga ccagcggcgt gcacaccttc ccggctgtcc tacagtcctc aggactctac        600
tccctcagca gcgtggtgac cgtgccctcc agcagcttgg gcacccagac ctacatctgc        660
aacgtgaatc acaagcccag caacaccaag gtggacaaga agttgagcc caaatcttgt        720 gacaaaactc acacatgccc accgtgccca gcacctgaac tcctggggggg accgtcagtc        780 ttcctcttcc ccccaaaacc caaggacacc ctcatgatct cccggacccc tgaggtcaca        840
tgcgtggtgg tggacgtgag ccacgaagac cctgaggtca agttcaactg gtacgtggac        900
ggcgtggagg tgcatacagc ctggacacag ccccgtgaag agcagtacaa cagtacctac        960
cgagtggtca gtgtcctcac cgtcctgcac caggactggc tgaatggcaa ggagtacaag       1020
tgcaaggtct ccaacaaagc cctcccagcc cccatcgaga aaaccatctc caaacccaaa       1080
ggaagagccc agacacctca agtatacacc ataccccac ctcgtgaaca aatgtccaag       1140
aagaaggtta gtctgacctg cctggtcacc aacttcttct ctgaagccat cagtgtggag       1200
tgggagagca atgggcagcc ggagaacaac tacaagacca cgcctcccgt gctggactcc       1260
gacggctcct tcttcctcta cagcaagctc accgtggaca gagcaggtg gcagcagggg       1320 aacgtcttct catgctccgt gatgcatgag gctctgcaca accactacac gcagaagagc       1380
ctctccctgt ctccgggtaa a                                                 1401
```

<210> SEQ ID NO 20
<211> LENGTH: 467
<212> TYPE: PRT
<213> ORGANISM: Artificial sequence
<220> FEATURE:
<223> OTHER INFORMATION: Heavy chain Protein sequence of i129v1
      (variable + 'improved' v1 constant region)

<400> SEQUENCE: 20

```
Met Leu Leu Gly Leu Lys Trp Val Phe Phe Val Val Phe Tyr Gln Gly
1               5                   10                  15

Val His Cys Glu Val Gln Leu Val Glu Ser Gly Gly Gly Leu Val Gln
            20                  25                  30

Pro Lys Gly Ser Leu Lys Leu Ser Cys Ala Ala Ser Gly Phe Thr Phe
        35                  40                  45

Asn Thr Tyr Ala Met Asn Trp Val Arg Gln Ala Pro Gly Lys Gly Leu
    50                  55                  60

Glu Trp Val Ala Arg Ile Arg Ser Lys Ser Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Gln Ser Met Leu Tyr Leu Gln Met Asn Asn Leu Lys Lys Glu Asp Thr
            100                 105                 110

Ala Met Tyr Tyr Cys Val Gly Tyr Gly Ser Gly Gly Asn Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175
```

-continued

```
Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
            210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
            290                 295                 300

His Thr Ala Trp Thr Gln Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Pro Lys Gly Arg Ala Gln Thr Pro Gln Val
            355                 360                 365

Tyr Thr Ile Pro Pro Pro Arg Glu Gln Met Ser Lys Lys Lys Val Ser
            370                 375                 380

Leu Thr Cys Leu Val Thr Asn Phe Phe Ser Glu Ala Ile Ser Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys
465
```

```
<210> SEQ ID NO 21
<211> LENGTH: 1401
<212> TYPE: DNA
<213> ORGANISM: Artificial sequence
<220> FEATURE:
<223> OTHER INFORMATION: Heavy chain DNA sequence of i129v2 (variable +
      'improved' v2 constant region)

<400> SEQUENCE: 21
atgctgttgg ggctgaagtg ggttttcttt gttgtttttt atcaaggtgt gcattgtgag      60
gtgcagcttg ttgagtctgg tggaggattg gtgcagccta agggtcatt gaaactctca      120 tgtgcagcct ctggattcac cttcaatacc tacgccatga actgggtccg ccaggctcca      180
ggaaagggtt tggaatgggt tgctcgcata agaagtaaaa gtaataatta tgcaacatat      240
tatgccgatt cagtgaaaga caggttcacc atatccagag atgattcaca aagcatgctc      300
```

-continued

```
tatctgcaaa tgaacaactt gaaaaggag  gacacagcca tgtattactg tgtagggtac      360
ggtagtgggg gaaactactg gggtcaagga  acctcagtca ccgtctccag cgcttccacc      420
aagggcccat cggtcttccc cctggcaccc  tcctccaaga gcacctctgg gggcacagcg      480
gccctgggct gcctggtcaa ggactacttc  cccgaaccgg tgacggtgtc gtggaactca      540
ggcgccctga ccagcggcgt gcacaccttc  ccggctgtcc tacagtcctc aggactctac      600
tccctcagca gcgtggtgac cgtgccctcc  agcagcttgg gcacccagac ctacatctgc      660
aacgtgaatc acaagcccag caacaccaag  gtggacaaga agttgagcc caaatcttgt       720 gacaaaactc acacatgccc accgtgccca  gcacctgaac tcctggggggg accgtcagtc      780 ttcctcttcc ccccaaaacc caaggacacc  ctcatgatct cccggacccc tgaggtcaca      840
tgcgtggtgg tggacgtgag ccacgaagac  cctgaggtca gttcaactg  gtacgtggac      900 ggcgtggagg tgcatacagc ctggacacag  ccccgtgaag agcagtacaa cagtacctac      960
cgagtggtca gtgtcctcac cgtcctgcac  caggactggc tgaatggcaa ggagtacaag     1020
tgcaaggtct ccaacaaagc cctcccagcc  cccatcgaga aaaccatctc caaagccaaa     1080
ggaagagccc gaacacctca gtatacacc  atacccccat cccgtgatga gctgtccaag      1140
aagaaggtta gtctgacctg cctggtcaaa  aacttctatt ctgaagccat cagtgtggag     1200
tgggagagca atgggcagcc ggagaacaac  tacaagacca cgcctcccgt gctggactcc     1260
gacggctcct tcttcctcta cagcaagctc  accgtggaca gagcaggtg  gcagcagggg     1320 aacgtcttct catgctccgt gatgcatgag  gctctgcaca accactacac gcagaagagc     1380
ctctccctgt ctccgggtaa a                                               1401
```

```
<210> SEQ ID NO 22
<211> LENGTH: 467
<212> TYPE: PRT
<213> ORGANISM: Artificial sequence
<220> FEATURE:
<223> OTHER INFORMATION: Heavy chain Protein sequence of i129v2
      (variable + 'improved' v2 constant region)

<400> SEQUENCE: 22

Met Leu Leu Gly Leu Lys Trp Val Phe Phe Val Val Phe Tyr Gln Gly
1               5                   10                  15

Val His Cys Glu Val Gln Leu Val Glu Ser Gly Gly Gly Leu Val Gln
            20                  25                  30

Pro Lys Gly Ser Leu Lys Leu Ser Cys Ala Ala Ser Gly Phe Thr Phe
        35                  40                  45

Asn Thr Tyr Ala Met Asn Trp Val Arg Gln Ala Pro Gly Lys Gly Leu
    50                  55                  60

Glu Trp Val Ala Arg Ile Arg Ser Lys Ser Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Gln Ser Met Leu Tyr Leu Gln Met Asn Asn Leu Lys Lys Glu Asp Thr
            100                 105                 110

Ala Met Tyr Tyr Cys Val Gly Tyr Gly Ser Gly Gly Asn Tyr Trp Gly
        115                 120                 125

Gln Gly Thr Ser Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160
```

```
Ala Leu Gly Cys Leu Val Lys Asp Tyr Phe Pro Glu Pro Val Thr Val
            165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
            195                 200                 205

Pro Ser Ser Ser Leu Gly Thr Gln Thr Tyr Ile Cys Asn Val Asn His
            210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Lys Phe Asn Trp Tyr Val Asp Gly Val Glu Val
            290                 295                 300

His Thr Ala Trp Thr Gln Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Arg Ala Arg Thr Pro Gln Val
                355                 360                 365

Tyr Thr Ile Pro Pro Ser Arg Asp Glu Leu Ser Lys Lys Lys Val Ser
            370                 375                 380

Leu Thr Cys Leu Val Lys Asn Phe Tyr Ser Glu Ala Ile Ser Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
            450                 455                 460

Pro Gly Lys
465
```

```
<210> SEQ ID NO 23
<211> LENGTH: 1401
<212> TYPE: DNA
<213> ORGANISM: Artificial sequence
<220> FEATURE:
<223> OTHER INFORMATION: Heavy chain DNA sequence of i129v3 (variable +
      'improved' v3 constant region)

<400> SEQUENCE: 23
atgctgttgg ggctgaagtg ggttttcttt gttgtttttt atcaaggtgt gcattgtgag        60
gtgcagcttg ttgagtctgg tggaggattg gtgcagccta aagggtcatt gaaactctca       120
tgtgcagcct ctggattcac cttcaatacc tacgccatga actgggtccg ccaggctcca       180
ggaaagggtt tggaatgggt tgctcgcata agaagtaaaa gtaataatta tgcaacatat       240
```

```
tatgccgatt cagtgaaaga caggttcacc atatccagag atgattcaca aagcatgctc    300
tatctgcaaa tgaacaactt gaaaaaggag gacacagcca tgtattactg tgtagggtac    360
ggtagtgggg gaaactactg gggtcaagga acctcagtca ccgtctccag cgcttccacc    420
aagggcccat cggtcttccc cctggcaccc tcctccaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga agttgagcc caaatcttgt     720 gacaaaactc acacatgccc accgtgccca gcacctgaac tcctgggggg accgtcagtc    780
ttcctcttcc ccccaaaacc caaggacacc ctcatgatct cccggacccc tgaggtcaca    840
tgcgtggtgg tggacgtgag ccacgaagac cctgaggtca gttcaactg gtacgtggac      900 ggcgtggagg tgcataatgc caagacaaag ccccgtgaag agcagtacaa cagtacctac    960
cgagtggtca gtgtcctcac cgtcctgcac caggactggc tgaatggcaa ggagtacaag   1020
tgcaaggtct ccaacaaagc cctcccagcc cccatcgaga aaaccatctc caaagccaaa   1080
ggaagagccc gaacacctca gtatacacc ctgcccccat cccgtgatga gctgaccaag    1140
aagaaggtta gtctgacctg cctggtcaaa ggcttctatt ctagcgccat cgccgtggag   1200
tgggagagca atgggcagcc ggagaacaac tacaagacca cgcctcccgt gctggactcc   1260
gacggctcct tcttcctcta cagcaagctc accgtggaca gagcaggtg gcagcagggg    1320 aacgtcttct catgctccgt gatgcatgag gctctgcaca accactacac gcagaagagc   1380
ctctccctgt ctccgggtaa a                                            1401
```

<210> SEQ ID NO 24
<211> LENGTH: 467
<212> TYPE: PRT
<213> ORGANISM: Artificial sequence
<220> FEATURE:
<223> OTHER INFORMATION: Heavy chain Protein sequence of i129v3
     (variable + 'improved' v3 constant region)

<400> SEQUENCE: 24

```
Met Leu Leu Gly Leu Lys Trp Val Phe Phe Val Val Phe Tyr Gln Gly
1               5                   10                  15

Val His Cys Glu Val Gln Leu Val Glu Ser Gly Gly Gly Leu Val Gln
            20                  25                  30

Pro Lys Gly Ser Leu Lys Leu Ser Cys Ala Ala Ser Gly Phe Thr Phe
        35                  40                  45

Asn Thr Tyr Ala Met Asn Trp Val Arg Gln Ala Pro Gly Lys Gly Leu
    50                  55                  60

Glu Trp Val Ala Arg Ile Arg Ser Lys Ser Asn Asn Tyr Ala Thr Tyr
65                  70                  75                  80

Tyr Ala Asp Ser Val Lys Asp Arg Phe Thr Ile Ser Arg Asp Asp Ser
                85                  90                  95

Gln Ser Met Leu Tyr Leu Gln Met Asn Asn Leu Lys Lys Glu Asp Thr
            100                 105                 110

Ala Met Tyr Tyr Cys Val Gly Tyr Gly Ser Gly Gly Asn Tyr Trp Gly
            115                 120                 125

Gln Gly Thr Ser Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
```

-continued

```
145              150               155                160
Ala Leu Gly Cys Leu Val Lys Asp Tyr Phe Pro Glu Pro Val Thr Val
            165               170               175

Ser Trp Asn Ser Gly Ala Leu Thr Ser Gly Val His Thr Phe Pro Ala
            180               185               190

Val Leu Gln Ser Ser Gly Leu Tyr Ser Leu Ser Ser Val Val Thr Val
            195               200               205

Pro Ser Ser Ser Leu Gly Thr Gln Thr Tyr Ile Cys Asn Val Asn His
    210               215               220

Lys Pro Ser Asn Thr Lys Val Asp Lys Lys Val Glu Pro Lys Ser Cys
225               230               235               240

Asp Lys Thr His Thr Cys Pro Pro Cys Pro Ala Pro Glu Leu Leu Gly
            245               250               255

Gly Pro Ser Val Phe Leu Phe Pro Pro Lys Pro Lys Asp Thr Leu Met
            260               265               270

Ile Ser Arg Thr Pro Glu Val Thr Cys Val Val Val Asp Val Ser His
            275               280               285

Glu Asp Pro Glu Val Lys Phe Asn Trp Tyr Val Asp Gly Val Glu Val
    290               295               300

His Asn Ala Lys Thr Lys Pro Arg Glu Glu Gln Tyr Asn Ser Thr Tyr
305               310               315               320

Arg Val Val Ser Val Leu Thr Val Leu His Gln Asp Trp Leu Asn Gly
            325               330               335

Lys Glu Tyr Lys Cys Lys Val Ser Asn Lys Ala Leu Pro Ala Pro Ile
            340               345               350

Glu Lys Thr Ile Ser Lys Ala Lys Gly Arg Ala Arg Thr Pro Gln Val
            355               360               365

Tyr Thr Leu Pro Pro Ser Arg Asp Glu Leu Thr Lys Lys Lys Val Ser
    370               375               380

Leu Thr Cys Leu Val Lys Gly Phe Tyr Ser Ser Ala Ile Ala Val Glu
385               390               395               400

Trp Glu Ser Asn Gly Gln Pro Glu Asn Asn Tyr Lys Thr Thr Pro Pro
            405               410               415

Val Leu Asp Ser Asp Gly Ser Phe Phe Leu Tyr Ser Lys Leu Thr Val
            420               425               430

Asp Lys Ser Arg Trp Gln Gln Gly Asn Val Phe Ser Cys Ser Val Met
            435               440               445

His Glu Ala Leu His Asn His Tyr Thr Gln Lys Ser Leu Ser Leu Ser
    450               455               460

Pro Gly Lys
465

<210> SEQ ID NO 25
<211> LENGTH: 714
<212> TYPE: DNA
<213> ORGANISM: Artificial sequence
<220> FEATURE:
<223> OTHER INFORMATION: 27 Light chain DNA sequence (variable region +
      Kappa constant)

<400> SEQUENCE: 25
atgaagttgc ctgttaggct gttggtgctg atgttctgga ttcctgcttc catcagtgat        60
gttttgatga cccaaactcc actctccctg cctgtcagtc ttggagatca agcctccatc       120
tcttgcagat ctagtcagat cattgtacat actaatggaa acacctattt agaatggtac       180
```

-continued

```
ctgcagaaac caggccagtc tccaaacctc ctgatctaca aagtttccaa ccgattttct    240 gggggtcccag acaggttcag tggcagtgga tcagggacag atttcacact caagatcagc   300
agagtggagg ctgaggatct gggagtttat tactgctttc aaggttcaca tgttccattc    360
acgttcggct cggggacaaa gttggaaata aaacgtacgg tagcggcccc atctgtcttc    420
atcttcccgc atctgatga gcagttgaaa tctggaactg cctctgttgt gtgcctgctg     480
aataacttct atcccagaga ggccaaagta cagtggaagg tggataacgc cctccaatcg    540
ggtaactccc aggagagtgt cacagagcag gacagcaagg acagcaccta cagcctcagc    600
agcaccctga cgctgagcaa agcagactac gagaaacaca agtctacgc ctgcgaagtc     660 acccatcagg gcctgagctc gcccgtcaca aagagcttca acaggggaga gtgt          714
```

```
<210> SEQ ID NO 26
<211> LENGTH: 238
<212> TYPE: PRT
<213> ORGANISM: Artificial sequence
<220> FEATURE:
<223> OTHER INFORMATION: 27 Light chain protein sequence (variable
      region + Kappa constant)

<400> SEQUENCE: 26

Met Lys Leu Pro Val Arg Leu Leu Val Leu Met Phe Trp Ile Pro Ala
1               5                   10                  15

Ser Ile Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ile Ile
        35                  40                  45

Val His Thr Asn Gly Asn Thr Tyr Leu Glu Trp Tyr Leu Gln Lys Pro
    50                  55                  60

Gly Gln Ser Pro Asn Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Phe Thr Phe Gly Ser Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

```
<210> SEQ ID NO 27
<211> LENGTH: 1404
<212> TYPE: DNA
<213> ORGANISM: Artificial sequence
```

-continued

```
<220> FEATURE:
<223> OTHER INFORMATION: Heavy chain DNA sequence of i27v1 (variable +
     'improved' v1 constant region)

<400> SEQUENCE: 27
atgaacttct ggctcagctt gattttcctt gtccttgttt taaaaggtgt ccagtgtgaa      60
gtgaagctgg tggagtctgg gggaggctta gtgcagcctg gagggtccct gaaactctcc     120
tgtgcaacct ctggattcac tttcagtcac tattacatgt attgggttcg ccagactcca     180
gagaagaggc tggagtgggt cgcatacatt agtaatgatg gtgataacac ctattatcca     240
gacactataa ggggccgatt caccatctcc agagacaatg ccaggaacac cctgtacctg     300
caaatgagcc gtctgaagtc tgaggacaca gccatgtatt actgtgcaag agggaagtac     360 gacgggcct ggtttgctta ctggggccaa gggactctgg tcactgtctc tagcgcttcc     420
accaagggcc atcggtctt ccccctggca ccctcctcca gagcacctc tggggggcaca      480 gcggccctgg gctgcctggt caaggactac ttccccgaac cggtgacggt gtcgtggaac     540
tcaggcgccc tgaccagcgg cgtgcacacc ttccggctg tcctacagtc ctcaggactc      600
tactccctca gcagcgtggt gaccgtgccc tccagcagct tgggcaccca gacctacatc     660
tgcaacgtga atcacaagcc cagcaacacc aaggtggaca gaaagttga gcccaaatct      720 tgtgacaaaa ctcacacatg cccaccgtgc ccagcacctg aactcctggg gggaccgtca     780
gtcttcctct ccccccaaa acccaaggac accctcatga tctcccggac ccctgaggtc      840
acatgcgtgg tggtggacgt gagccacgaa gaccctgagg tcaagttcaa ctggtacgtg     900
gacggcgtgg aggtgcatac agcctggaca gcccccgtg aagagcagta caacagtacc      960
taccgagtgg tcagtgtcct caccgtcctg caccaggact ggctgaatgg caaggagtac    1020
aagtgcaagg tctccaacaa agccctccca gcccccatcg agaaaaccat ctccaaaccc    1080
aaaggaagag cccagacacc tcaagtatac accatacccc cacctcgtga caaatgtcc     1140 aagaagaagg ttagtctgac ctgcctggtc accaacttct tctctgaagc catcagtgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaa                                          1404

<210> SEQ ID NO 28
<211> LENGTH: 468
<212> TYPE: PRT
<213> ORGANISM: Artificial sequence
<220> FEATURE:
<223> OTHER INFORMATION: Heavy chain Protein sequence of i27v1
     (variable + 'improved' v1 constant region)

<400> SEQUENCE: 28

Met Asn Phe Trp Leu Ser Leu Ile Phe Leu Val Leu Val Leu Lys Gly
1               5                   10                  15

Val Gln Cys Glu Val Lys Leu Val Glu Ser Gly Gly Gly Leu Val Gln
            20                  25                  30

Pro Gly Gly Ser Leu Lys Leu Ser Cys Ala Thr Ser Gly Phe Thr Phe
        35                  40                  45

Ser His Tyr Tyr Met Tyr Trp Val Arg Gln Thr Pro Glu Lys Arg Leu
    50                  55                  60

Glu Trp Val Ala Tyr Ile Ser Asn Asp Gly Asp Asn Thr Tyr Tyr Pro
65                  70                  75                  80
```

Asp Thr Ile Arg Gly Arg Phe Thr Ile Ser Arg Asp Asn Ala Arg Asn
            85                  90                  95

Thr Leu Tyr Leu Gln Met Ser Arg Leu Lys Ser Glu Asp Thr Ala Met
            100                 105                 110

Tyr Tyr Cys Ala Arg Gly Lys Tyr Asp Gly Ala Trp Phe Ala Tyr Trp
            115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
            165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
            195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
            245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
    290                 295                 300

Val His Thr Ala Trp Thr Gln Pro Arg Glu Glu Gln Tyr Asn Ser Thr
305                 310                 315                 320

Tyr Arg Val Val Ser Val Leu Thr Val Leu His Gln Asp Trp Leu Asn
            325                 330                 335

Gly Lys Glu Tyr Lys Cys Lys Val Ser Asn Lys Ala Leu Pro Ala Pro
            340                 345                 350

Ile Glu Lys Thr Ile Ser Lys Pro Lys Gly Arg Ala Gln Thr Pro Gln
            355                 360                 365

Val Tyr Thr Ile Pro Pro Pro Arg Glu Gln Met Ser Lys Lys Lys Val
    370                 375                 380

Ser Leu Thr Cys Leu Val Thr Asn Phe Phe Ser Glu Ala Ile Ser Val
385                 390                 395                 400

Glu Trp Glu Ser Asn Gly Gln Pro Glu Asn Asn Tyr Lys Thr Thr Pro
            405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
    450                 455                 460

Ser Pro Gly Lys
465

<210> SEQ ID NO 29
<211> LENGTH: 214

```
<212> TYPE: PRT
<213> ORGANISM: Artificial sequence
<220> FEATURE:
<223> OTHER INFORMATION: Light chain protein sequence of iTrastuzumabv1
      and iTrastuzumabv2

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30
<211> LENGTH: 450
<212> TYPE: PRT
<213> ORGANISM: Artificial sequence
<220> FEATURE:
<223> OTHER INFORMATION: Heavy chain protein sequence of iTrastuzumabv1

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
```

-continued

```
              100                 105                 110
Gly Thr Leu Val Thr Val Ser Ser Ala Ser Thr Lys Gly Pro Ser Val
          115                 120                 125
Phe Pro Leu Ala Pro Ser Ser Lys Ser Thr Ser Gly Gly Thr Ala Ala
      130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
              165                 170                 175
Leu Gln Ser Ser Gly Leu Tyr Ser Leu Ser Ser Val Val Thr Val Pro
          180                 185                 190
Ser Ser Ser Leu Gly Thr Gln Thr Tyr Ile Cys Asn Val Asn His Lys
          195                 200                 205
Pro Ser Asn Thr Lys Val Asp Lys Lys Val Glu Pro Lys Ser Cys Asp
      210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
              245                 250                 255
Ser Arg Thr Pro Glu Val Thr Cys Val Val Val Asp Val Ser His Glu
          260                 265                 270
Asp Pro Glu Val Lys Phe Asn Trp Tyr Val Asp Gly Val Glu Val His
          275                 280                 285
Thr Ala Trp Thr Gln Pro Arg Glu Glu Gln Tyr Asn Ser Thr Tyr Arg
      290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
              325                 330                 335
Lys Thr Ile Ser Lys Pro Lys Gly Arg Ala Gln Thr Pro Gln Val Tyr
          340                 345                 350
Thr Ile Pro Pro Pro Arg Glu Gln Met Ser Lys Lys Lys Val Ser Leu
          355                 360                 365
Thr Cys Leu Val Thr Asn Phe Phe Ser Glu Ala Ile Ser Val Glu Trp
      370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
              405                 410                 415
Lys Ser Arg Trp Gln Gln Gly Asn Val Phe Ser Cys Ser Val Met His
              420                 425                 430
Glu Ala Leu His Asn His Tyr Thr Gln Lys Ser Leu Ser Leu Ser Pro
          435                 440                 445
Gly Lys
    450
```

<210> SEQ ID NO 31
<211> LENGTH: 450
<212> TYPE: PRT
<213> ORGANISM: Artificial sequence
<220> FEATURE:
<223> OTHER INFORMATION: Heavy chain protein sequence of iTrastuzumabv2

<400> SEQUENCE: 31

Glu Val Gln Leu Val Glu Ser Gly Gly Gly Leu Val Gln Pro Gly Gly

-continued

```
1              5             10            15
Ser Leu Arg Leu Ser Cys Ala Ala Ser Gly Phe Asn Ile Lys Asp Thr
            20            25            30

Tyr Ile His Trp Val Arg Gln Ala Pro Gly Lys Gly Leu Glu Trp Val
            35            40            45

Ala Arg Ile Tyr Pro Thr Asn Gly Tyr Thr Arg Tyr Ala Asp Ser Val
    50            55            60

Lys Gly Arg Phe Thr Ile Ser Ala Asp Thr Ser Lys Asn Thr Ala Tyr
65            70            75            80

Leu Gln Met Asn Ser Leu Arg Ala Glu Asp Thr Ala Val Tyr Tyr Cys
            85            90            95

Ser Arg Trp Gly Gly Asp Gly Phe Tyr Ala Met Asp Tyr Trp Gly Gln
            100           105           110

Gly Thr Leu Val Thr Val Ser Ser Ala Ser Thr Lys Gly Pro Ser Val
            115           120           125

Phe Pro Leu Ala Pro Ser Ser Lys Ser Thr Ser Gly Gly Thr Ala Ala
    130           135           140

Leu Gly Cys Leu Val Lys Asp Tyr Phe Pro Glu Pro Val Thr Val Ser
145           150           155           160

Trp Asn Ser Gly Ala Leu Thr Ser Gly Val His Thr Phe Pro Ala Val
            165           170           175

Leu Gln Ser Ser Gly Leu Tyr Ser Leu Ser Ser Val Val Thr Val Pro
            180           185           190

Ser Ser Ser Leu Gly Thr Gln Thr Tyr Ile Cys Asn Val Asn His Lys
            195           200           205

Pro Ser Asn Thr Lys Val Asp Lys Lys Val Glu Pro Lys Ser Cys Asp
    210           215           220

Lys Thr His Thr Cys Pro Pro Cys Pro Ala Pro Glu Leu Leu Gly Gly
225           230           235           240

Pro Ser Val Phe Leu Phe Pro Pro Lys Pro Lys Asp Thr Leu Met Ile
            245           250           255

Ser Arg Thr Pro Glu Val Thr Cys Val Val Val Asp Val Ser His Glu
            260           265           270

Asp Pro Glu Val Lys Phe Asn Trp Tyr Val Asp Gly Val Glu Val His
            275           280           285

Thr Ala Trp Thr Gln Pro Arg Glu Glu Gln Tyr Asn Ser Thr Tyr Arg
    290           295           300

Val Val Ser Val Leu Thr Val Leu His Gln Asp Trp Leu Asn Gly Lys
305           310           315           320

Glu Tyr Lys Cys Lys Val Ser Asn Lys Ala Leu Pro Ala Pro Ile Glu
            325           330           335

Lys Thr Ile Ser Lys Ala Lys Gly Arg Ala Arg Thr Pro Gln Val Tyr
            340           345           350

Thr Ile Pro Pro Ser Arg Asp Glu Leu Ser Lys Lys Val Ser Leu
            355           360           365

Thr Cys Leu Val Lys Asn Phe Tyr Ser Glu Ala Ile Ser Val Glu Trp
    370           375           380

Glu Ser Asn Gly Gln Pro Glu Asn Asn Tyr Lys Thr Thr Pro Pro Val
385           390           395           400

Leu Asp Ser Asp Gly Ser Phe Phe Leu Tyr Ser Lys Leu Thr Val Asp
            405           410           415

Lys Ser Arg Trp Gln Gln Gly Asn Val Phe Ser Cys Ser Val Met His
            420           425           430
```

-continued

```
Glu Ala Leu His Asn His Tyr Thr Gln Lys Ser Leu Ser Leu Ser Pro
        435                 440                 445

Gly Lys
    450

<210> SEQ ID NO 32
<211> LENGTH: 93
<212> TYPE: PRT
<213> ORGANISM: Homo sapiens
<220> FEATURE:
<221> NAME/KEY: misc_feature
<223> OTHER INFORMATION: Human IgG1 sequence 286-278

<400> SEQUENCE: 32

Asn Ala Lys Thr Lys Pro Arg Glu Glu Gln Tyr Asn Ser Thr Tyr Arg
1               5                   10                  15

Val Val Ser Val Leu Thr Val Leu His Gln Asp Trp Leu Asn Gly Lys
            20                  25                  30

Glu Tyr Lys Cys Lys Val Ser Asn Lys Ala Leu Pro Ala Pro Ile Glu
        35                  40                  45

Lys Thr Ile Ser Lys Ala Lys Gly Gln Pro Arg Glu Pro Gln Val Tyr
    50                  55                  60

Thr Leu Pro Pro Ser Arg Asp Glu Leu Thr Lys Asn Gln Val Ser Leu
65                  70                  75                  80

Thr Cys Leu Val Lys Gly Phe Tyr Pro Ser Asp Ile Ala
                85                  90

<210> SEQ ID NO 33
<211> LENGTH: 93
<212> TYPE: PRT
<213> ORGANISM: Mus musculus
<220> FEATURE:
<221> NAME/KEY: misc_feature
<223> OTHER INFORMATION: Mouse IgG3 sequence 286-378

<400> SEQUENCE: 33

Thr Ala Trp Thr Gln Pro Arg Glu Ala Gln Tyr Asn Ser Thr Phe Arg
1               5                   10                  15

Val Val Ser Ala Leu Pro Ile Gln His Gln Asp Trp Met Arg Gly Lys
            20                  25                  30

Glu Phe Lys Cys Lys Val Asn Asn Lys Ala Leu Pro Ala Pro Ile Glu
        35                  40                  45

Arg Thr Ile Ser Lys Pro Lys Gly Arg Ala Gln Thr Pro Gln Val Tyr
    50                  55                  60

Thr Ile Pro Pro Pro Arg Glu Gln Met Ser Lys Lys Lys Val Ser Leu
65                  70                  75                  80

Thr Cys Leu Val Thr Asn Phe Phe Ser Glu Ala Ile Ser
                85                  90

<210> SEQ ID NO 34
<211> LENGTH: 9
<212> TYPE: PRT
<213> ORGANISM: Artificial sequence
<220> FEATURE:
<223> OTHER INFORMATION: Subdomain 286-306

<400> SEQUENCE: 34

Phe Arg Val Val Ser Ala Leu Thr Val
1               5
```

```
<210> SEQ ID NO 35
<211> LENGTH: 9
<212> TYPE: PRT
<213> ORGANISM: Artificial sequence
<220> FEATURE:
<223> OTHER INFORMATION: Subdomain 286-306

<400> SEQUENCE: 35

Thr Phe Arg Val Val Ser Ala Leu Thr
1               5

<210> SEQ ID NO 36
<211> LENGTH: 9
<212> TYPE: PRT
<213> ORGANISM: Artificial sequence
<220> FEATURE:
<223> OTHER INFORMATION: Subdomain 286-306

<400> SEQUENCE: 36

Val Val Ser Ala Leu Thr Val Leu His
1               5

<210> SEQ ID NO 37
<211> LENGTH: 9
<212> TYPE: PRT
<213> ORGANISM: Artificial sequence
<220> FEATURE:
<223> OTHER INFORMATION: Subdomain 286-306

<400> SEQUENCE: 37

Leu Val Leu His Gln Asp Trp Leu Asn
1               5

<210> SEQ ID NO 38
<211> LENGTH: 9
<212> TYPE: PRT
<213> ORGANISM: Artificial sequence
<220> FEATURE:
<223> OTHER INFORMATION: Subdomain 286-306

<400> SEQUENCE: 38

Tyr Arg Val Val Ser Val Leu Thr Val
1               5

<210> SEQ ID NO 39
<211> LENGTH: 9
<212> TYPE: PRT
<213> ORGANISM: Artificial sequence
<220> FEATURE:
<223> OTHER INFORMATION: Subdomain 286-306

<400> SEQUENCE: 39

Ala Gln Tyr Asn Ser Thr Phe Arg Val
1               5

<210> SEQ ID NO 40
<211> LENGTH: 9
<212> TYPE: PRT
<213> ORGANISM: Artificial sequence
<220> FEATURE:
<223> OTHER INFORMATION: Subdomain 286-306

<400> SEQUENCE: 40

Glu Gln Tyr Asn Ser Thr Tyr Arg Val
1               5

<210> SEQ ID NO 41
```

```
<211> LENGTH: 9
<212> TYPE: PRT
<213> ORGANISM: Artificial sequence
<220> FEATURE:
<223> OTHER INFORMATION: Subdomain 339-378

<400> SEQUENCE: 41

Leu Thr Cys Leu Val Thr Asn Phe Phe
1               5

<210> SEQ ID NO 42
<211> LENGTH: 9
<212> TYPE: PRT
<213> ORGANISM: Artificial sequence
<220> FEATURE:
<223> OTHER INFORMATION: Subdomain 339-378

<400> SEQUENCE: 42

Leu Thr Cys Leu Val Thr Gly Phe Phe
1               5

<210> SEQ ID NO 43
<211> LENGTH: 9
<212> TYPE: PRT
<213> ORGANISM: Artificial sequence
<220> FEATURE:
<223> OTHER INFORMATION: Subdomain 339-378

<400> SEQUENCE: 43

Val Tyr Thr Ile Pro Pro Pro Arg Glu
1               5

<210> SEQ ID NO 44
<211> LENGTH: 9
<212> TYPE: PRT
<213> ORGANISM: Artificial sequence
<220> FEATURE:
<223> OTHER INFORMATION: Subdomain 339-378

<400> SEQUENCE: 44

Val Tyr Thr Leu Pro Pro Pro Arg Glu
1               5

<210> SEQ ID NO 45
<211> LENGTH: 128
<212> TYPE: PRT
<213> ORGANISM: Homo sapiens

<400> SEQUENCE: 45

Tyr Val Asp Gly Val Glu Val His Asn Ala Lys Thr Lys Pro Arg Glu
1               5                   10                  15

Glu Gln Tyr Asn Ser Thr Tyr Arg Val Val Ser Val Leu Thr Val Leu
                20                  25                  30

His Gln Asp Trp Leu Asn Gly Lys Glu Tyr Lys Cys Lys Val Ser Asn
            35                  40                  45

Lys Ala Leu Pro Ala Pro Ile Glu Lys Thr Ile Ser Lys Ala Lys Gly
        50                  55                  60

Gln Pro Arg Glu Pro Gln Val Tyr Thr Leu Pro Pro Ser Arg Asp Glu
65                  70                  75                  80

Leu Thr Lys Asn Gln Val Ser Leu Thr Cys Leu Val Lys Gly Phe Tyr
                85                  90                  95

Pro Ser Asp Ile Ala Val Glu Trp Glu Ser Asn Gly Gln Pro Glu Asn
            100                 105                 110
```

-continued

```
Asn Tyr Lys Thr Thr Pro Pro Val Leu Asp Ser Asp Gly Ser Phe Phe
        115             120             125

<210> SEQ ID NO 46
<211> LENGTH: 130
<212> TYPE: PRT
<213> ORGANISM: Mus musculus

<400> SEQUENCE: 46

Phe Val Asp Asn Lys Glu Val His Thr Ala Trp Thr Gln Pro Arg Glu
1               5               10              15

Ala Gln Tyr Asn Ser Thr Phe Arg Val Val Ser Ala Leu Pro Ile Gln
        20              25              30

His Gln Asp Trp Met Arg Gly Lys Glu Phe Lys Cys Lys Val Asn Asn
        35              40              45

Lys Ala Leu Pro Ala Pro Ile Glu Arg Thr Ile Ser Lys Pro Lys Gly
    50              55              60

Arg Ala Gln Thr Pro Gln Val Tyr Thr Ile Pro Pro Pro Arg Glu Gln
65              70              75              80

Met Ser Lys Lys Lys Val Ser Leu Thr Cys Leu Val Thr Asn Phe Phe
            85              90              95

Ser Glu Ala Ile Ser Val Glu Trp Glu Arg Asn Gly Glu Leu Glu Gln
        100             105             110

Asp Tyr Lys Asn Thr Pro Pro Ile Leu Asp Ser Asp Gly Thr Tyr Phe
        115             120             125

Leu Tyr
    130

<210> SEQ ID NO 47
<211> LENGTH: 93
<212> TYPE: PRT
<213> ORGANISM: Artificial sequence
<220> FEATURE:
<223> OTHER INFORMATION: SD286 306+339 378 construct with reversion of
      murine residues to human residues

<400> SEQUENCE: 47

Thr Ala Trp Thr Gln Pro Arg Glu Glu Gln Tyr Asn Ser Thr Tyr Arg
1               5               10              15

Val Val Ser Val Leu Thr Val Leu His Gln Asp Trp Leu Asn Gly Lys
        20              25              30

Glu Tyr Lys Cys Lys Val Ser Asn Lys Ala Leu Pro Ala Pro Ile Glu
        35              40              45

Lys Thr Ile Ser Lys Ala Lys Gly Gln Pro Arg Glu Pro Gln Val Tyr
    50              55              60

Thr Leu Pro Pro Pro Arg Glu Gln Met Ser Lys Lys Lys Val Ser Leu
65              70              75              80

Thr Cys Leu Val Thr Gly Phe Phe Ser Glu Ala Ile Ser
            85              90
```